(12) United States Patent
Rasochova et al.

(10) Patent No.: US 7,928,290 B2
(45) Date of Patent: Apr. 19, 2011

(54) VIRAL CAPSID FUSION PEPTIDE EXPRESSING PLANT CELLS

(75) Inventors: Lada Rasochova, San Diego, CA (US); Philip Phuoc Dao, San Diego, CA (US)

(73) Assignee: Dow AgroSciences LLC, Indianapolis, IN (US)

( * ) Notice: Subject to any disclaimer, the term of this patent is extended or adjusted under 35 U.S.C. 154(b) by 766 days.

(21) Appl. No.: 11/069,601

(22) Filed: Feb. 28, 2005

(65) **

VIRAL CAPSID FUSION PEPTIDE EXPRESSING PLANT CELLS

CROSS REFERENCE TO RELATED APPLICATIONS

This application claims priority to U.S. Provisional patent application Ser. No. 60/548,744, filed Feb. 27, 2004, entitled "High Efficiency Peptide Production in Plant Cells."

STATEMENT OF GOVERNMENT INTEREST

This application is under a United States Government contract with the National Institutes of Health, National Institute of Allergy and Infectious Disease (NIAID), Cooperative Agreement No. 1-U01-AI054641-01.

FIELD OF THE INVENTION

The present invention provides an improved process for the production of recombinant peptides. In particular, the present invention provides an improved process for the production of recombinant peptides in the form of viral capsid fusion proteins which can be assembled in vivo in plant cell suspension cultures. The invention also includes plasmids, sequences, and plant cells which allow for non-infectious viral capsid fusion peptide production.

BACKGROUND OF THE INVENTION

Bacterial, yeast, plant, insect, and mammalian cell expression systems are currently used to produce recombinant peptides, with varying degrees of success. One goal in creating expression systems for the production of heterologous peptides is to provide broad based, flexible, efficient, economic, and practical platforms and processes that can be utilized in commercial, therapeutic, and vaccine applications. For example, for the production of certain peptides, it would be ideal to have an expression system capable of producing, in an efficient and inexpensive manner, large quantities of final, desirable products in vivo in order to eliminate or reduce downstream reassembly costs.

Currently, bacteria are the most widely used expression system for the production of recombinant peptides because of their potential to produce abundant quantities of recombinant peptides. Bacteria generally do not glycosylate, acetylate, acylate, phosphorylate, or gamma-carboxylate eukaryotic proteins, and, therefore, are limited in their capacities to produce, in vivo, certain types of heterologous eukaryotic peptides that require post-translational modifications. Additional steps modifying the bacterially produced eukaryotic peptides are likely to increase the time and reduce the overall yield of peptide production, diluting many of the advantages of the bacterial host expression system. Therefore, alternative non-bacterial expression systems have been utilized to overcome the inherent limitations of bacterial expression systems.

One particular host expression systems analyzed for their ability to produce heterologous peptides has been whole plants and plant cell suspension cultures. The safe and inexpensive culture of plants provides an improved alternative host for the cost effective production of certain peptides. This alternative is particularly attractive where the protein is complex, requires glycosylation, needs to be free of human or animal infectious viruses, and bacterial toxins.

Whole plants offer the advantages of being relatively inexpensive to grow in vast quantities, with the potential for a great yield of the desired recombinant protein from the large biomass of the harvested transgenic or viral infected plants. As a result, whole plants have been developed as expression systems for commercial production of biopharmaceutical proteins intended for human or veterinary administration.

Significant time and resources have been spent on trying to improve the cost of production and yield of heterologous proteins in non-bacterial systems in order to take advantage of the inherent abilities of these systems. While progress has been made in both of these areas, additional processes and platforms for the production of heterologous peptides in non-bacterial expression systems would be beneficial.

Viruses and Virus Like Particles

One approach for improving peptide production in host cell expression systems is to make use of the properties of infectious recombinant viruses to produce recombinant peptides of interest. The use of infectious viruses in plant host systems is particularly well known. See, for example, Porta & Lomonossoff, (2002) "Viruses as vectors for the expression of foreign sequences in plants," Biotechnology and Genetic Engineering Reviews 19: 245-291.

Recent strategies have focused on the production of heterologous peptides in virus like particle (VLP) structures. In general, encapsidated viruses include a protein coat or "capsid" that is assembled to contain the viral nucleic acid. Many viruses have capsids that can be "self-assembled" from the individually expressed capsids, both within the cell the capsid is expressed in ("in vivo assembly"), and outside of the cell after isolation and purification ("in vitro assembly"). Ideally, capsids are modified to contain a target recombinant peptide, generating a recombinant viral capsid-peptide fusion. The fusion peptide can then be expressed in a cell, and, ideally, assembled in vivo to form recombinant viral or virus-like particles.

The production of heterologous proteins via virus capsid fusion proteins assembled into VLPs in plants has been met with varying success. See, for example, C Marusic et al., *J Virol.* 75(18):8434-39 (September 2001) (use of infectious helical potato virus X in whole *Nicotiana benthamiana* to express virus capsids terminally fused to an antigenic, six amino acid HIV peptide, with in vivo formation of the recombinant virus particles); F R Brennan et al., *Vaccine* 17(15-16): 1846-57 (9 Apr. 1999) (use of infectious cowpea mosaic virus or helical potato virus X capsids terminally fused to an antigenic, *Staphylococcus aureus* peptide, with in vivo formation of recombinant virus particles expression in whole cowpea plants (*Vigna uniquiculata*)); C Porta et al., Intervirology 39(1-2):79-84 (1996) (describing an infectious cowpea mosaic virus expressing a chimeric coat protein including an antigenic HIV sequence in whole plants).

U.S. Pat. No. 5,874,087 to Lomonossoff & Johnson describes production of infectious plant viruses, in plant cells or whole plants, wherein the viral capsids are engineered to contain a biologically active peptide, such as a hormone, growth factor, or antigenic peptide. A virus selected from the genera Comovirus, Tombusvirus, Sobemovirus, and Nepovirus is engineered to contain the exogenous peptide encoding sequence and the entire engineered genome of the virus is expressed to produce the recombinant virus. The specification stresses that multiplication of the modified virus is a central part of the invention.

U.S. Pat. No. 6,232,099 to Chapman et al. describes the use of infective, rod-shaped viruses to produce foreign proteins connected to viral capsid subunits in whole plants. Rod-shaped viruses, also classified as helical viruses, such as potato virus X (PVX) have recombinant peptides of interest inserted into the genome of the virus to create recombinant viral capsid-peptide fusions. The recombinant, infective virus is then used to infect a plant cell of a whole plant, wherein, the virus actively replicates in the plant cell and further infects other cells, ultimately infecting the entire host plant. Ultimately, the recombinant viral capsid-peptide fusion is purified from the plant.

Chapman et al. also teaches that a limited insertion size is tolerated by icosahedral viruses. Chapman et al. cite WO 92/18618, which limits the size of the recombinant peptide in an icosahedral virus for expression in a plant host cell to 26 amino acids in length, in supporting his assertion. Chapman et al. theorize that a larger peptide present in the internal insertion site in the capsid of icosahedral viruses may result in disruption of the geometry of the protein and/or its ability to successfully interact with other capsids leading to failure of the chimeric virus to assemble.

U.S. Pat. No. 6,042,832 to Koprowski et al. describes fusion capsid proteins comprising a plant virus capsid protein fused to an antigenic polypeptide. The resultant particles are produced in whole plants.

The utilization of infectious recombinant viruses to produce heterologous proteins in capsid fusion proteins is not, however, without its drawbacks. One particularly troubling aspect is the ability of these viruses to mutate in vivo, resulting in capsid proteins that are essentially wild type revertants without the fused heterologous protein of interest, or mutated, non-desirable recombination capsid fusion protein products. See, or example, Porta & Lomonossoff (1996) "Use of viral replicons for the expression of genes in plants," Molecular Biotechnology 5:209-221; Dolja et al. (1993) "Spontaneous mutagenesis of a plant potyvirus genome after insertion of a foreign gene," J. Virol. 67(10):5968-5975; Dawson et al. (2001) "Assessment of recombinants that arise from the use of a TMV-based transient expression vector," Virol. 284(2): 182-189 (describing the deletion of the foreign inserted gene in inoculated whole plants). The lack of stability of these viral vectors in whole plants potentially reduces the yield of overall protein product, and may lead to inconsistencies and irregularities in the capsid-fusion product. Such irregularities may be particularly troublesome wherein the integrity of the protein product is essential for a particular desired physio-chemical characteristic in the peptide.

As a result of the inherent instability of infectious recombinant viruses in plants, there is still a need in the field of commercial recombinant protein production for an efficient peptide production system that offers plant-system-type benefits.

In addition, the use of whole plants for the production of recombinant peptides also presents potential problems. For instance, long development times, batch to batch variations in product yield, containment issues, the difficulty of applying good manufacturing practice to the early stages of production, the possibility of contamination with agrochemicals and fertilizers, as well as the impact of pests, disease and variable cultivation conditions due to microclimate and soil differences all result in a potential inconsistent host system for the production of recombinant peptides.

Therefore, it is an object of the present invention to provide a stable and consistent plant cell expression system for the production of virus like particles containing capsid fusion proteins.

It is another object of the present invention to provide plant cells for use as host cells in a stable expression system for the production of virus like particles containing capsid fusion proteins.

It is still another object of the present invention to provide processes for the improved production of virus like particles containing capsid fusion proteins in plant cells, including plant cell suspension cultures.

It is yet another object of the present invention to provide novel constructs and nucleic acids for use in plant cell expression system for the production of virus like particles containing capsid fusion proteins.

SUMMARY OF THE INVENTION

The present invention provides a process for the production of recombinant peptides, wherein non-infectious plasmids encoding fusion peptides comprising a viral capsid and a recombinant peptide of interest are stably inserted into the genome of a host plant cell and expressed in a suspension plant cell culture. The viral capsid-heterologous peptide fusion products can be expressed in vivo as virus like particles. The present invention does not require the utilization of an infective viral agent; rather, non-infectious nucleic acid encoding a capsid-heterologous peptide fusion product is stably inserted into the genome of a plant cell, which can be cultured in a fermentation process to produce the peptide of interest. Such a process results in a less variable, and more stable host system for the expression of capsid fusion proteins containing heterologous peptides.

It has been discovered that infectious viruses containing capsid-heterologous peptide fusion proteins utilized to express heterologous peptides of interest in whole plants exhibit genetic instability in the whole plant that results in mutations in the recombinant capsid protein nucleic acid, and the expressed mutant capsid either cannot assemble into virus particles or contains a mutated target peptide. The present invention provides increased stability of the resultant heterologous peptide, with the additional benefits of precise control over growth conditions, batch to batch consistency, a high level of containment, and the ability to produce recombinant proteins in compliance with good manufacturing practices.

The capsid-fusion protein products can form virus like particles within the cell. The virus like particle may result in the improved efficiency of achieving a high purity of the recovered peptide. The virus like particles produced in the cell typically are not capable of infecting the plant cell. The viral capsid sequence can be derived from both trophic and non-trophic viruses, wherein trophism is determined by the specific plant cell utilized as the expression host. In one embodiment, the viral capsid protein is derived from a virus that exhibits a native or natural trophism towards the plant cell utilized to express the fusion product. In one embodiment, the viral capsid protein is derived from a virus that does not exhibit a native or natural trophism towards the plant cell utilized to express the fusion product. In one embodiment, the cell does not include artificially introduced viral proteins other than the desired capsid protein sequences utilized to produce the fusion product. In another embodiment, the cell includes artificially introduced viral proteins or nucleic acids other than the desired capsid protein sequences utilized to produce the fusion product, wherein the additional viral proteins or nucleic acids do not confer infectivity to the nucleic acid sequences. In one embodiment, the viral capsid is derived from a virus with a tropism to a different family of organisms than the plant cell expression host. In another embodiment, the viral capsid is derived from a virus with a tropism to a different genus of organisms than the plant cell expression host. In another embodiment, the viral capsid is derived from a virus with a tropism to a different species of organisms than the cell utilized to express the fusion product. In one embodiment of the present invention, the capsid is derived from a rod shaped plant virus. In a particular embodiment, the capsid is a rod shaped viral capsid derived from the group selected from Tobacco Mosaic Virus and Potato Virus X (PVX). In one embodiment of the present invention, the capsid protein is derived from an icosahedral virus. In a particular embodiment, the capsid is derived from a plant icosahedral virus. In a more particular embodiment, the icosahedral capsid is derived from the group selected from Cowpea Mosaic Virus, Cowpea Chlorotic Mottle Virus, and Alfalfa Mosaic Virus.

The present invention also provides plant cells that include a non-infectious nucleic acid construct containing an expression cassette encoding for a fusion protein of a virus capsid and a recombinant peptide. The fusion peptide of the virus capsid and recombinant peptide is operably linked to a promoter and terminator that functions in plant cells. In one specific embodiment, the nucleic acid is genomically integrated in the plant cell, wherein the integration results in the stable inheritance and expression of the nucleic acid encoding the capsid fusion protein from generation to generation. In one specific embodiment of the present invention, the capsid protein is derived from an icosahedral virus. In one embodiment the cell produces virus like particles or soluble cage structures. In one embodiment, the plant cell is a Monocot or a Dicot. In a particular embodiment, the plant cell is *Nicotiana tabacum*. In an alternative embodiment, the plant cell is *Oryza sativa*. In one embodiment of the present invention, the recombinant peptide fused to the viral capsid protein is a therapeutic peptide useful for human or animal treatments. In one particular embodiment, the recombinant peptide is an antigenic peptide. In a particular embodiment, the antigenic peptide is a glycosylated antigenic peptide. In one embodiment, the plant cells or extracts containing capsid-recombinant peptide virus like particles containing an antigenic peptide can be administered as a vaccine to a human or animal. In an alternative embodiment, the purified capsid-recombinant peptide virus like particles containing an antigenic peptide can be administered as a vaccine to a human or animal. In one embodiment, the heterologous peptide is an antimicrobial peptide. In another particular embodiment, the recombinant peptide is a peptide that is toxic to the plant host cell when in free monomeric form. In one embodiment, the recombinant peptide fused to the capsid is at least 7, at least 8, at least, 9, at least 10, at least 12, at least 15, at least 20, at least 25, at least 30, at least 35, at least 40, at least 45, at least 50, at least 55, at least 60, at least 65, at least 75, at least 85, at least 95, at least 99, or at least 100 amino acids in length.

In one embodiment of the present invention, the recombinant peptide fused to the capsid contains at least one monomer of a desired target peptide. In an alternative embodiment, the recombinant peptide contains more than one monomer of a desired target peptide. In certain embodiments, the peptide is composed of at least two, at least 5, at least 10, at least 15 or at least 20 separate monomers that are operably linked as a concatameric peptide to the capsid. In another embodiment, the individual monomers in the concatameric peptide are linked by cleavable linker regions. In still another embodiment, the recombinant peptide is inserted into at least one surface loop of the viral capsid. In one embodiment, the recombinant peptide is inserted into at least one surface loop of an icosahedral viral capsid. In one embodiment, at least one monomer is inserted into more than one surface loops of a viral capsid protein. In still another embodiment, the recombinant peptide is inserted into at least one outer surface loop of the viral capsid. In an alternative embodiment, the recombinant peptide is inserted into at least one inner surface loop of the viral capsid.

More than one loop of the virus like particle can be modified. In one particular embodiment, the recombinant peptide is expressed on at least two surface loops of the virus-like particle. In another embodiment, at least two different peptides are inserted into at least two surface loops of the viral capsid, cage or virus-like particle. In another embodiment, at least three recombinant peptides are inserted into at least three surface loops of the virus-like particle. The recombinant peptides in the surface loops can have the same amino acid sequence. In separate embodiments, the amino acid sequence of the recombinant peptides in the surface loops differ.

In still another embodiment, the cell includes at least one additional nucleic acid encoding either a wild-type capsid or different capsid-recombinant peptide fusion peptide, wherein the multiple capsids can be assembled in vivo to produce chimeric virus like particles.

In one aspect of the present invention, plant cells are provided that include a fusion protein of a viral capsid and a recombinant peptide. In one specific embodiment of the present invention, the plant cell is a monocot. In an alternative embodiment, the plant cell is a dicot. In one embodiment, the capsid-recombinant peptide fusion protein assembles in vivo to form a virus like particle.

In one embodiment of the present invention, the plant cells containing the nucleic acid construct encoding the capsid protein-recombinant peptide fusion peptide is obtained by nuclear transformation. In one embodiment, the plant cell is obtained by plastid transformation. In still another embodiment, the plant cell is obtained by chloroplast transformation.

The present invention further provides for non-infectious nucleic acid constructs containing an expression cassette encoding for a fusion protein of a viral capsid and a recombinant peptide. In one embodiment of the present invention, the expression cassette encoding for a fusion protein of a viral capsid and a recombinant peptide is operably linked to a promoter and terminator. In one embodiment of the present invention, the capsid is derived from a plant virus. In one embodiment of the present invention, the capsid is derived from an icosahedral plant virus. In a particular embodiment, the capsid is an icosahedral viral capsid derived from the group selected from Cowpea Mosaic Virus, Cowpea Chlorotic Mottle Virus, and Alfalfa Mosaic Virus.

In one embodiment of the present invention, the recombinant peptide contains at least one monomer of a desired target peptide. In an alternative embodiment, the recombinant peptide contains more than one monomer of a desired target peptide. In still another embodiment, the recombinant peptide is inserted into at least one surface loop of the icosahedral virus capsid.

In another embodiment, the nucleic acid construct includes additional nucleic acid sequences including at least one promoter that functions in plant cell. In another embodiment, the nucleic acid construct includes additional nucleic acid sequences including at least one promoter that functions in plant cells, and at least one terminator that functions in plant cells. In one embodiment, a nucleic acid sequence encoding a selection marker operably linked to a promoter and a terminator sequence is included in the nucleic acid construct. In an alternative embodiment, a selection marker operably linked to a promoter and a termination sequence is provided on a separate nucleic acid construct. In another embodiment, the nucleic acid construct includes additional nucleic acid sequences derived from the 3' untranslated region (3' UTR) of the viral RNA. In still another embodiment, the nucleic acid construct includes at least one encapsidation signal derived from the viral RNA. In still another embodiment, the non-infectious nucleic acid construct includes additional nucleic acid sequences derived from the viral RNA, wherein the additional sequences do not confer infectivity to the viral nucleic acids.

In one aspect, the present invention provides a process for producing a recombinant peptide including:
   a) providing a plant cell;
   b) providing a non-infectious nucleic acid encoding a fusion peptide, wherein the fusion is of at least one heterologous peptide and at least one viral capsid protein;
   c) transforming the plant cell, wherein the nucleic acid is subsequently integrated into the genome of the plant cell;
   d) expressing the nucleic acid in the plant cell, wherein the plant cells are grown in a suspension plant cell culture in a fermentation process;
   e) wherein the expression in the plant cell provides for in vivo assembly of the fusion peptide into virus like particles; and
   f) isolating the virus like particles.

In one embodiment, the process further includes: e) cleaving the fusion product to separate the recombinant peptide from the viral capsid protein. In still another embodiment, the process further provides: f) following step (e), isolating the recombinant peptide. See, for example, FIG. 1. In one embodiment of the present invention, the plant cell is selected from the group consisting of *Oryza sativa* and *Nicotiana tabacum*.

The nucleic acid encoding a recombinant peptide and a viral capsid protein is operably linked to a promoter sequence and a terminator sequence.

In one embodiment, the process includes co-expressing another nucleic acid encoding a wild-type capsid or a different capsid-recombinant peptide fusion peptide, wherein the capsids are assembled in vivo to produce chimeric virus like particles.

In another aspect of the present invention, an expression system for the production of recombinant peptides is provided including:
   a) a plant cell capable of being propagated in a plant cell medium;
   b) a non-infectious nucleic acid encoding a fusion peptide; wherein the fusion peptide comprises at least one recombinant peptide, and at least one viral capsid, and wherein the nucleic acid is capable of genomic integration and expression in the plant cell; and
   c) a growth medium.

The nucleic acid encoding the fusion peptide can be operably linked to a promoter sequence and a terminator sequence. When expressed the fusion peptide can assemble into virus like particles within the cell. In one embodiment, the promoter is a plant promoter.

DETAILED DESCRIPTION

Figure 1:
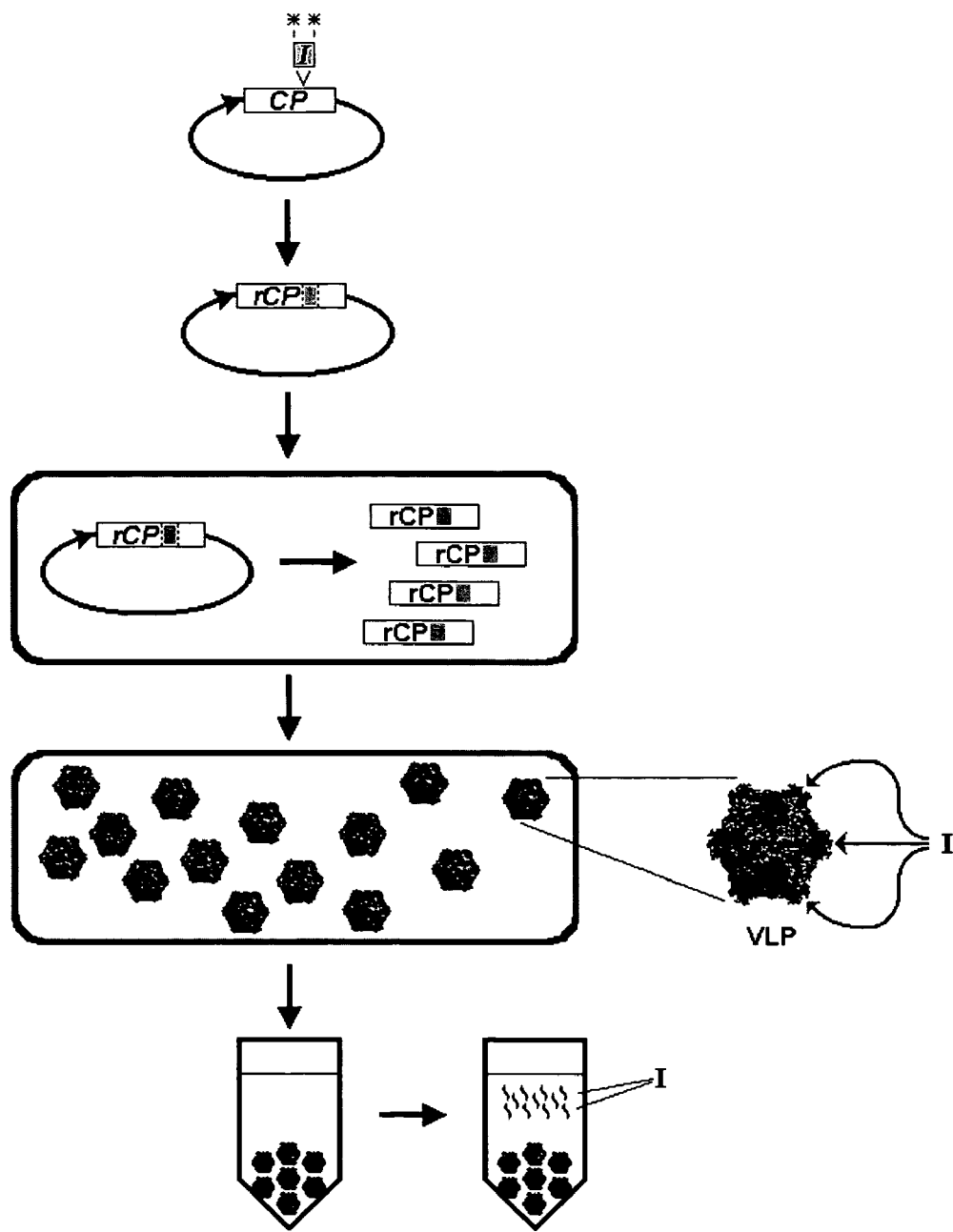
FIG. 1 illustrates a scheme for production of peptide monomers in Virus-Like Particles (VLP) in plant cells. A sequence encoding a desired target peptide ("I") is inserted into a sequence encoding a viral coat protein ("CP") constructing a gene encoding recombinant viral coat protein ("rCP"), which, as part of a vector, is transformed into the plant cell and expressed to form recombinant coat proteins ("rCP"). Optional cleavage sites ("*") are also shown. A plant cell is transfected or transformed with a plant expression plasmid for with the rCP gene. rCP can assemble into VLPs in plant cells. The peptide insert is displayed on VLP surfaces. Chimeric VLPs can be purified from the plant cells, and the desired target peptides can optionally be cleaved off the purified VLPs and purified.

The present invention provides a process for the production of recombinant peptides, wherein non-infectious plasmids encoding fusion peptides comprising a viral capsid and a recombinant peptide of interest are stably inserted into the genome of a host plant cell and expressed in a suspension plant cell culture. The viral capsid-heterologous peptide fusion products can be expressed in vivo as virus like particles. The present invention further provides plant cells and nucleic acid constructs for use in the process. Specifically, the invention provides plant cells, capable of propagation in suspension plant cell cultures, with a nucleic acid construct containing an expression cassette encoding a fusion peptide of a viral capsid and a recombinant peptide. The fusion peptide can be operably linked to a promoter sequence and a termination sequence. In one embodiment, the expression in the plant cell of the fusion peptide produces virus like particles or soluble cage structures. The invention also provides nucleic acid constructs capable of integrating into the genome of the plant cell and encoding the fusion peptide of a viral capsid and a recombinant peptide, which can in one embodiment, be a therapeutic peptide useful for human and animal treatments.

The invention also provides a process for producing a recombinant peptide in a suspension plant cell culture by providing: a nucleic acid capable of genomic integration in a plant cell containing an expression cassette encoding a fusion peptide of a recombinant peptide and a viral capsid operably linked to a promoter sequence and a termination sequence; expressing the nucleic acid in the plant cell in a suspension plant cell culture, wherein the expression in the plant cell provides for in vivo assembly of the fusion peptide into virus like particles; and isolating the virus like particles.

The term "infectious" as used herein means the ability of a virus particle to transfer its nucleic acid to a host or introduction of a viral nucleic acid into a host, wherein the viral nucleic acid is replicated, viral proteins are translated, and new viral particles capable of further transfer of nucleic acid to a host are assembled. The term "non-infectious" as used herein means the inability of a virus-derived nucleic acid to replicate in a host after introduction into a host, wherein the viral proteins are translated, and new virus like particles assembled that are not capable of initiating viral infection process in a host. The term "peptide" as used herein is not limited to any particular molecular weight, and can also include proteins or polypeptides.

I. Recombinant Plant Cells The present invention provides plant cells that include a non-infectious nucleic acid construct capable of genomic integration and encoding a fusion peptide of a viral capsid and a recombinant peptide operably linked to a promoter sequence and a termination sequence. The cells can be utilized in a process for producing recombinant peptides.

The plant cells can be derived by transforming the native plant cell with a nucleic acid construct containing an expression cassette encoding a fusion peptide of a viral capsid and a recombinant peptide operably linked to a promoter sequence and a termination sequence, wherein the nucleic acid construct is stably integrated into the host cell's genome. Stable transformation depends on the integration of the foreign DNA into the genome. The foreign DNA can be integrated into the nuclear or plastid genome of the plant. The nucleic acid construct can be randomly inserted into the genome of the plant, or can be directed to a particular region of the genome through homologous recombination. The plant cell can be obtained by any means known in the art, including nuclear transformation, plastid transformation, and chloroplast transformation. See, for example, U.S. Pat. No. 6,218,145; EP 012345149; WO 0121782; U.S. Pat. No. 6,515,206; WO 99/10513; U.S. Pat. No. 5,693,507; WO 02055651; WO 0170939; U.S. Pat. No. 6,472,586; WO 02057466; U.S. Pat. No. 5,057,422; WO 0120974 Staub, J. M. and Maliga, P, (1992) "Long regions of homologous DNA are incorporated into the tobacco plastid genome by transformation," Plant Cell 4: 39-45.

Viral Capsids

In one embodiment, the invention provides plant cells for use in a process for producing peptides by expression of the peptide fused to a viral capsid from a non-infectious plasmid stably integrated into the host genome. The expression can result in the formation of at least one virus like particle (VLP) in the cell.

Viruses can be classified into those with helical symmetry or icosahedral symmetry. Generally recognized capsid morphologies include: icosahedral (including icosahedral proper, isometric, quasi-isometric, and geminate or "twinned"), polyhedral (including spherical, ovoid, and lemon-shaped), bacilliform (including rhabdo- or bullet-shaped, and fusiform or cigar-shaped), and helical (including rod, cylindrical, and filamentous); any of which may be tailed and/or may contain surface projections, such as spikes or knobs.

Morphology

In one embodiment of the invention, the amino acid sequence of the capsid is selected from the capsids of viruses classified as having any morphology. In one embodiment, the capsid is derived from a rod shaped virus. In a particular embodiment, the capsid is derived from a rod shaped plant virus. In a more particular embodiment, the capsid is a rod shaped viral capsid derived from the group selected from Tobacco Mosaic Virus (TMV) and Potato Virus X (PVX). TMV consists of a single plus-sense genomic RNA (6.5 kb) encapsidated with a unique coat protein (17.5 kDa) which results in rod-shaped particles (300 nm). Potato Virus X are filamentous, non enveloped; usually flexuous viruses with a clear modal length of 515 nm and 13 nm wide (Brandes, 1964). The capsid structure forms a basic helix with a pitch of 3.4 nm (Varma et al., 1968).

In one embodiment, the capsid has an icosahedral morphology. In one embodiment, the capsid amino acid sequence will be selected from the capsids of entities that are icosahedral proper. In another embodiment, the capsid amino acid sequence will be selected from the capsids of icosahedral viruses. In one particular embodiment, the capsid amino acid sequence will be selected from the capsids of icosahedral plant viruses. However, in another embodiment, the viral capsid will be derived from an icosahedral virus not infectious to plants. For example, in one embodiment, the virus is a virus infectious to mammals.

Generally, viral capsids of icosahedral viruses are composed of numerous protein sub-units arranged in icosahedral (cubic) symmetry. Native icosahedral capsids can be built up, for example, with 3 subunits forming each triangular face of a capsid, resulting in 60 subunits forming a complete capsid. Representative of this small viral structure is e.g. bacteriophage ØX174. Many icosahedral virus capsids contain more than 60 subunits. Many capsids of icosahedral viruses contain an antiparallel, eight-stranded beta-barrel folding motif. The motif has a wedge-shaped block with four beta strands (designated BIDG) on one side and four (designated CHEF) on the other. There are also two conserved alpha-helices (designated A and B), one is between betaC and betaD, the other between betaE and betaF.

Enveloped viruses can exit an infected cell without its total destruction by extrusion (budding) of the particle through the membrane, during which the particle becomes coated in a lipid envelope derived from the cell membrane (See, e.g.: A J Cann (ed.) (2001) *Principles of Molecular Virology* (Academic Press); A Granoff and R G Webster (eds.) (1999) *Encyclopedia of Virology* (Academic Press); D L D Caspar (1980) *Biophys. J.* 32:103; D L D Caspar and A Klug (1962) *Cold Spring Harbor Symp. Quant. Biol.* 27:1; J Grimes et al. (1988) *Nature* 395:470; J E Johnson (1996) *Proc. Nat'l Acad. Sci. USA* 93:27; and J Johnson and J Speir (1997) *J. Mol. Biol.* 269:665).

Viruses

Viral taxonomies recognize the following taxa of encapsidated-particle entities:

Group I Viruses, i.e. the dsDNA viruses;
Group II Viruses, i.e. the ssDNA viruses;
Group III Viruses, i.e. the dsRNA viruses;
Group IV Viruses, i.e. the ssRNA (+)-stranded viruses with no DNA stage;
Group V Viruses, i.e. the ssRNA (−)-stranded viruses;
Group VI Viruses, i.e. the RNA retroid viruses, which are ssRNA reverse transcribing viruses;
Group VII Viruses, i.e. the DNA retroid viruses, which are dsDNA reverse transcribing viruses;
Deltaviruses;
Viroids; and
Satellite phages and Satellite viruses, excluding Satellite nucleic acids and Prions.

Members of these taxa are well known to one of ordinary skill in the art and are reviewed in: H. V. Van Regenmortel et al. (eds.), Virus Taxonomy: Seventh Report of the International Committee on Taxonomy of Viruses (2000) (Academic Press/Elsevier, Burlington Mass., USA); the Virus Taxonomy web-page of the University of Leicester (UK) Microbiology & Immunology Department; and the on-line "Virus" and "Viroid" sections of the Taxonomy Browser of the National Center for Biotechnology Information (NCBI) of the National Library of Medicine of the National Institutes of Health of the US Department of Health & Human Services (Washington, D.C., USA).

The amino acid sequence of the capsid may be selected from the capsids of any members of any of these taxa. Amino acid sequences for capsids of the members of these taxa may be obtained from sources, including, but not limited to, e.g.: the on-line "Nucleotide" (Genbank), "Protein," and "Structure" sections of the PubMed search facility offered by the NCBI.

In one embodiment, the capsid amino acid sequence will be selected from taxa members that are specific for at least one of the following hosts: bacteria, fingi including yeasts, plants, protists including algae, invertebrate animals, vertebrate animals, and humans. In one embodiment, the capsid amino acid sequence will be selected from members of any one of the following taxa: Group I, Group II, Group III, Group IV, Group V, Group VII, Viroids, and Satellite Viruses. In one embodiment, the capsid amino acid sequence will be selected from members of any one of these seven taxa that are specific for at least one of the six above-described host types. In a more specific embodiment, the capsid amino acid sequence will be selected from members of any one of Group II, Group III, Group IV, Group VII, and Satellite Viruses; or from any one of Group II, Group IV, Group VII, and Satellite Viruses. In another embodiment, the viral capsid is selected from Group IV or Group VII.

The viral capsid sequence can be derived from a virus not tropic to the cell. In one embodiment, the cell does not include viral proteins from the particular selected virus other than the desired icosahedral capsids. In one embodiment, the viral capsid is derived from a virus with a tropism to a different family of organisms than the cell. In another embodiment, the viral capsid is derived from a virus with a tropism to a different genus of organisms than the cell. In another embodiment, the viral capsid is derived from a virus with a tropism to a different species of organisms than the cell.

In a specific embodiment, the viral capsid is selected from a virus of Group IV.

In one embodiment, the viral capsid is selected from rod-shaped plant viruses. In a more particular embodiment, the viral capsid is selected from the group consisting of Tobacco Mosaic Virus and Potato Virus X.

In one embodiment, the viral capsid is selected form an icosahedral virus. The icosahedral virus can be selected from a member of any of the Papillomaviridae, Totiviridae, Dicistroviridae, Hepadnaviridae, Togaviridiae, Polyomaviridiae, Nodaviridae, Tectiviridae, Leviviridae, Microviridae, Sipoviridae, Nodaviridae, Picornoviridae, Parvoviridae, Calciviridae, Tetraviridae, and Satellite viruses.

In a particular embodiment, the sequence will be selected from members of any one of the taxa that are specific for at least one plant host. In one embodiment the icosahedral plant virus species will be a plant-infectious virus species that is or is a member of any of the Bunyaviridae, Reoviridae, Rhabdoviridae, Luteoviridae, Nanoviridae, Partitiviridae, Sequiviridae, Tymoviridae, Ourmiavirus, Tobacco Necrosis Virus Satellite, Caulimoviridae, Geminiviridae, Comoviridae, Sobemovirus, Tombusviridae, or Bromoviridae taxa. In one embodiment, the icosahedral plant virus species is a plant-infectious virus species that is or is a member of any of the Luteoviridae, Nanoviridae, Partitiviridae, Sequiviridae, Tymoviridae, Ourmiavirus, Tobacco Necrosis Virus Satellite, Caulimoviridae, Geminiviridae, Comoviridae, Sobemovirus, Tombusviridae, or Bromoviridae taxa. In specific embodiments, the icosahedral plant virus species is a plant infectious virus species that is or is a member of any of the Caulimoviridae, Geminiviridae, Comoviridae, Sobemovirus, Tombusviridae, or Bromoviridae. In more particular embodiments, the icosahedral plant virus species will be a plant-infectious virus species that is or is a member of any of the Comoviridae, Sobemovirus, Tombusviridae, or Bromoviridae. In more particular embodiments, the icosahedral plant virus species will be a plant-infectious virus species that is a member of the Comoviridae or Bromoviridae family. In a particular embodiment the viral capsid is derived from a Cowpea Mosaic Virus or a Cowpea Chlorotic Mottle Virus. In another embodiment, the viral capsid is derived from a species of the Bromoviridae taxa. In a specific embodiment, the capsid is derived from an Ilarvirus or an Alfamovirus. In a more specific embodiment, the capsid is derived from a Tobacco streak virus, or an Alfalfa mosaic virus (AMV) (including AMV 1 or AMV 2).

VLP

The viral capsid of the invention is non-infective in the host cells described. In one embodiment, a virus like particle (VLP) or cage structure is formed in the host cell during or after expression of the viral capsid. In one embodiment, the VLP or cage structure also includes the peptide of interest, and in a particular embodiment, the peptide of interest is expressed on the surface of the VLP. The expression system typically does not contain additional viral proteins that allow infectivity of the virus. In a typical embodiment, the expression system includes a host cell and a vector which codes for one or more viral capsids and an operably linked peptide of interest. The vector typically does not include additional viral proteins. The invention is derived from the discovery that viral capsids form to a greater extent in certain host cells and allow for more efficient recovery of recombinant peptide.

In one embodiment, the VLP or cage structure is a multimeric assembly of capsids, including from three to about 1,000 capsids. In one embodiment, the VLP or cage structure includes at least 30, at least 50, at least 60, at least 90 or at least 120 capsids. In another embodiment, each VLP or cage structure includes at least 150 capsids, at least 160, at least 170, or at least 180 capsids.

In one embodiment, the VLP is expressed as an icosahedral structure. In another embodiment, the VLP is expressed in the same geometry as the native virus that the capsid sequence is derived of. In a separate embodiment, however, the VLP does not have the identical geometry of the native virus. In certain embodiments, for example, the structure is produced in a particle formed of multiple capsids but not forming a native-type VLP. For example, a cage structure of as few as 3 viral capsids can be formed. In separate embodiments, cage structures of about 6, 9, 12, 15, 18, 21, 24, 27, 30, 33, 36, 39, 42, 45, 48, 51, 54, 57, or 60 capsids can be formed.

In one embodiment, at least one of the capsids includes at least one peptide of interest. In one embodiment, the peptide is expressed within at least one internal loop, or in at least one external surface loop of the VLP.

More than one loop of the viral capsid can be modified. In one particular embodiment, the recombinant peptide is expressed on at least two surface loops of the virus-like particle. In another embodiment, at least two different peptides are inserted into at least two surface loops of the viral capsid, cage or virus-like particle. In another embodiment, at least three recombinant peptides are inserted into at least three surface loops of the virus-like particle. The recombinant peptides in the surface loops can have the same amino acid sequence. In separate embodiments, the amino acid sequence of the recombinant peptides in the surface loops differs.

In certain embodiments, the host cell can be modified to improve assembly of the VLP. The host cell can, for example, be modified to include chaperone proteins that promote the formation of VLPs from expressed viral capsids. In another embodiment, the host cell is modified to include a repressor protein to more efficiently regulate the expression of the capsid to promote regulated formation of the VLPs.

The nucleic acid sequence encoding the viral capsid or proteins can also be additionally modified to alter the formation of VLPs (see e.g. Brumfield, et al. (2004) *J. Gen. Virol.* 85: 1049-1053). For example, these modifications are designed to alter the interior, exterior or the interface between adjacent subunits in the assembled protein cage. To accomplish this, mutagenic primers can be used to: (i) alter the interior surface charge of the viral nucleic acid binding region by replacing basic residues (e.g. K, R) in the N terminus with acidic glutamic acids (Douglas et al., 2002b); (ii) delete interior residues from the N terminus (in CCMV, usually residues 4-37); (iii) insert a cDNA encoding an 11 amino acid peptide cell-targeting sequence (Graf et al., 1987) into a surface exposed loop; and (iv) modify interactions between viral subunits by altering the metal binding sites (in CCMV, residues 81/148 mutant).

Recombinant Peptides Size

In one embodiment, the peptides operably linked to a viral capsid sequence contain at least two amino acids. In another embodiment, the peptides are at least three, at least four, at least five, or at least six amino acids in length. In a separate embodiment, the peptides are at least seven amino acids long. The peptides can also be at least eight, at least nine, at least ten, at least 11, 12, 13, 14, 15, 16, 17, 18, 19, 20, 30, 45, 50, 60, 65, 75, 85, 95, 96, 99 or more amino acids long. In one embodiment, the peptides encoded are at least 25 kD.

In one embodiment, the peptide will contain from 2 to about 300 amino acids, or about 5 to about 250 amino acids, or about 5 to about 200 amino acids, or about 5 to about 150 amino acids, or about 5 to about 100 amino acids. In another embodiment, the peptide contains or about 10 to about 140 amino acids, or about 10 to about 120 amino acids, or about 10 to about 100 amino acids.

In one embodiment, the peptides or proteins operably linked to a viral capsid sequence will contain about 500 amino acids. In one embodiment, the peptide will contain less than 500 amino acids. In another embodiment, the peptide will contain up to about 300 amino acids, or up to about 250, or up to about 200, or up to about 180, or up to about 160, or up to about 150, or up to about 140, or up to about 120, or up to about 110, or up to about 100, or up to about 90, or up to about 80, or up to about 70, or up to about 60, or up to about 50, or up to about 40 or up to about 30 amino acids.

In one embodiment, the recombinant peptide fused to the capsid is at least 7, at least 8, at least, 9, at least 10, at least 12, at least 15, at least 20, at least 25, at least 30, at least 35, at least 40, at least 45, at least 50, at least 55, at least 60, at least 65, at least 75, at least 85, at least 95, at least 99, or at least 100 amino acids.

In one embodiment of the present invention, the recombinant peptide contains at least one monomer of a desired target peptide. In an alternative embodiment, the recombinant peptide contains more than one monomer of a desired target peptide. In certain embodiments, the peptide is composed of at least two, at least 5, at least 10, at least 15 or at least 20 separate monomers that are operably linked as a concatameric peptide to the capsid. In another embodiment, the individual monomers in the concatameric peptide are linked by cleavable linker regions. In still another embodiment, the recombinant peptide is inserted into at least one surface loop of the icosahedral virus-like particle. In one embodiment, at least one monomer is inserted in a surface loop of the virus-like particle.

Classification

The peptides of interest that are fused to the viral capsids can be a heterologous protein that is not derived from the virus and, optionally, that is not derived from the same species as the cell.

The peptides of interest that are fused to the viral capsids can be functional peptides; structural peptides; antigenic peptides, toxic peptides, antimicrobial peptides, fragments thereof; precursors thereof, combinations of any of the foregoing; and/or concatamers of any of the foregoing. In one embodiment of the present invention, the recombinant peptide is a therapeutic peptide useful for human and animal treatments, including antigenic peptides used in a vaccine strategy. In a particular embodiment, the antigenic peptide is glycosylated in vivo.

Functional peptides include, but are not limited to, e.g.: bio-active peptides (i.e. peptides that exert, elicit, or otherwise result in the initiation, enhancement, prolongation, attenuation, termination, or prevention of a biological function or activity in or of a biological entity, e.g., an organism, cell, culture, tissue, organ, or organelle); catalytic peptides; microstructure- and nanostructure-active peptides (i.e. peptides that form part of engineered micro- or nanostructures in which, or in conjunction with which, they perform an activity, e.g., motion, energy transduction); and stimulant peptides (e.g., peptide flavorings, colorants, odorants, pheromones, attractants, deterrents, and repellants).

Bio-active peptides include, but are not limited to, e.g.: immunoactive peptides (e.g., antigenic peptides, allergenic peptides, peptide immunoregulators, peptide immunomodulators); signaling and signal transduction peptides (e.g., peptide hormones, cytokines, and neurotransmitters; receptors; agonist and antagonist peptides; peptide targeting and secretion signal peptides); and bio-inhibitory peptides (e.g., toxic, biocidal, or biostatic peptides, such as peptide toxins and antimicrobial peptides).

Structural peptides include, but are not limited to, e.g.: peptide aptamers; folding peptides (e.g., peptides promoting or inducing formation or retention of a physical conformation in another molecule); adhesion-promoting peptides (e.g., adhesive peptides, cell-adhesion-promoting peptides); interfacial peptides (e.g., peptide surfactants and emulsifiers); microstructure and nanostructure-architectural peptides (i.e. structural peptides that form part of engineered micro- or nano-structures); and pre-activation peptides (e.g., leader peptides of pre-, pro-, and pre-pro-proteins and -peptides; inteins).

Catalytic Peptides include, e.g., apo B RNA-editing cytidine deaminase peptides; catalytic peptides of glutaminyl-tRNA synthetases; catalytic peptides of aspartate transcarbamoylases; plant Type 1 ribosome-inactivating peptides; viral catalytic peptides such as, e.g., the foot-and-mouth disease virus [FMDV-2A] catalytic peptide; matrix metalloproteinase peptides; and catalytic metallo-oligopeptides.

The peptide can also be a peptide epitope, hapten, or a related peptide (e.g., antigenic viral peptide; virus related peptide, e.g., HIV-related peptide, hepatitis-related peptide; antibody idiotypic domain; cell surface peptide; antigenic human, animal, protist, plant, fungal, bacterial, and/or archaeal peptide; allergenic peptide and allergen desensitizing peptide).

The peptide can also be a peptide immunoregulators or immunomodulators (e.g., interferons, interleukins, peptide immunodepressants and immunopotentiators); an antibody peptides (e.g., single chain antibodies; single chain antibody fragments and constructs, e.g., single chain Fv molecules; antibody light chain molecules, antibody heavy chain molecules, domain-deleted antibody light or heavy chain molecules; single chain antibody domains and molecules, e.g., a CH1, CH1-3, CH3, CH1-4, CH4, VHCH1, CL, CDR1, or FR1-CDR1-FR2 domain; paratopic peptides; microantibodies); another binding peptide (e.g., peptide aptamers, intracellular and cell surface receptor proteins, receptor fragments; anti-tumor necrosis factor peptides).

The peptide can also be an enzyme substrate peptide or an enzyme inhibitor peptide (e.g., caspase substrates and inhibitors, protein kinase substrates and inhibitors, fluorescence-resonance-energy transfer-peptide enzyme substrates).

The peptide can also be a cell surface receptor peptide ligand, agonist, and antagonist (e.g., caeruleins, dynorphins, orexins, pituitary adenylate cyclase activating peptides, tumor necrosis factor peptides; synthetic peptide ligands, agonists, and antagonists); a peptide hormone (e.g., endocrine, paracrine, and autocrine hormones, including, e.g.: amylins, angiotensins, bradykinins, calcitonins, cardioexcitatory neuropeptides, casomorphins, cholecystokinins, corticotropins and corticotropin-related peptides, differentiation factors, endorphins, endothelins, enkephalins, erythropoietins, exendins, follicle-stimulating hormones, galanins, gastrins, glucagons and glucagon-like peptides, gonadotropins, growth hormones and growth factors, insulins, kallidins, kinins, leptins, lipotropic hormones, luteinizing hormones, melanocyte stimulating hormones, melatonins, natriuretic peptides, neurokinins, neuromedins, nociceptins, osteocalcins, oxytocins (i.e. ocytocins), parathyroid hormones, pleiotrophins, prolactins, relaxins, secretins, serotonins, sleep-inducing peptides, somatomedins, thymopoietins, thyroid stimulating hormones, thyrotropins, urotensins, vasoactive intestinal peptides, vasopressins); a peptide cytokine, chemokine, virokine, and viroceptor hormone releasing and release-inhibiting peptide (e.g., corticotropin-releasing hormones, cortistatins, follicle-stimulating-hormone-releasing factors, gastric inhibitory peptides, gastrin releasing peptides, gonadotropin-releasing hormones, growth hormone releasing hormones, luteinizing hormone-releasing hormones, melanotropin-releasing hormones, melanotropin-release inhibiting factors; nocistatins, pancreastatins, prolactin releasing peptides, prolactin release-inhibiting factors; somatostatins; thyrotropin releasing hormones); a peptide neurotransmitter or channel blocker (e.g., bombesins, neuropeptide Y, neurotensins, substance P) a peptide toxin, toxin precursor peptide, or toxin peptide portion. In certain embodiments, a peptide toxin contains no D-amino acids. Toxin precursor peptides can be those that contain no D-amino acids and/or that have not been converted by post-translational modification into a native toxin structure, such as, e.g., by action of a D configuration inducing agent (e.g., a peptide isomerase(s) or epimeras(e) or racemase(s) or transaminase(s)) that is capable of introducing a D-configuration in an amino acid(s), and/or by action of a cyclizing agent (e.g., a peptide thioesterase, or a peptide ligase such as a trans-splicing protein or intein) that is capable of form a cyclic peptide structure.

Toxin peptide portions can be the linear or pre-cyclized oligo- and poly-peptide portions of peptide-containing toxins. Examples of peptide toxins include, e.g., agatoxins, amatoxins, charybdotoxins, chlorotoxins, conotoxins, dendrotoxins, insectotoxins, margatoxins, mast cell degranulating peptides, saporins, sarafotoxins; and bacterial exotoxins such as, e.g., anthrax toxins, botulism toxins, diphtheria toxins, and tetanus toxins.

The peptide can also be a metabolism- and digestion-related peptide (e.g., cholecystokinin-pancreozymin peptides, peptide yy, pancreatic peptides, motilins); a cell adhesion modulating or mediating peptide, extracellular matrix peptide (e.g., adhesins, selectins, laminins); a neuroprotectant or myelination-promoting peptide; an aggregation inhibitory peptide (e.g., cell or platelet aggregation inhibitor peptides, amyloid formation or deposition inhibitor peptides); a joining peptide (e.g., cardiovascular joining neuropeptides, iga joining peptides); or a miscellaneous peptide (e.g., agouti-related peptides, amyloid peptides, bone-related peptides, cell-permeable peptides, conantokins, contryphans, contulakins, myelin basic protein, and others).

The peptide can also be post-translationally modified in vivo. In particular embodiments, the peptide may be, singularly or in combination, glycosylated, acetylated, acylated, phosphorylated, or gamma-carboxylated.

In certain embodiments, the peptide of interest is exogenous to the selected viral capsid. Peptides may be either native or synthetic in sequence (and their coding sequences may be either native or synthetic nucleotide sequences). Thus, e.g., native, modified native, and entirely artificial sequences of amino acids are encompassed. The sequences of the nucleic acid molecules encoding these amino acid sequences likewise may be native, modified native, or entirely artificial nucleic acid sequences, and may be the result of, e.g., one or more rational or random mutation and/or recombination and/or synthesis and/or selection process employed (i.e. applied by human agency) to obtain the nucleic acid molecules.

The coding sequence can be a native coding sequence for the target peptide, if available, but will more typically be a coding sequence that has been selected, improved, or optimized for use in the selected expression host cell: for example, by synthesizing the gene to reflect the codon use preference of a host species. In one embodiment of the invention, the host species is *Nicotiana tabacum*, and the codon preference of *Nicotiana tabacum* is taken into account when designing both the signal sequence and the peptide sequence. In an alternative embodiment of the invention, the host species is *Oryza sativa*, and the codon preference of *Oryza sativa* is taken into account when designing both the signal sequence and the peptide sequence Antigenic Peptides (Peptide Epitopes)

In one embodiment, an antigenic peptide is produced through expression with a viral capsid. The antigenic peptide can be selected from those that are antigenic peptides of human or animal pathogenic agents, including infectious agents, parasites, cancer cells, and other pathogenic agents. Such pathogenic agents also include the virulence factors and pathogenesis factors, e.g., exotoxins, endotoxins, et al., of those agents. The pathogenic agents may exhibit any level of virulence, i.e. they may be, e.g., virulent, avirulent, pseudo-virulent, semi-virulent, and so forth. In one embodiment, the antigenic peptide will contain an epitopic amino acid sequence from the pathogenic agent(s). In one embodiment, the epitopic amino acid sequence will include that of at least a portion of a surface peptide of at least one such agent. In one embodiment, the capsid-recombinant peptide virus like particles can be used as a vaccine in a human or animal application.

More than one antigenic peptide may be selected, in which case the resulting virus-like particles can present multiple different antigenic peptides. In a particularly embodiment of a multiple antigenic peptide format, the various antigenic peptides will all be selected from a plurality of epitopes from the same pathogenic agent. In a particular embodiment of a multi-antigenic-peptide format, the various antigenic peptides selected will all be selected from a plurality of closely related pathogenic agents, for example, different strains, subspecies, biovars, pathovars, serovars, or genovars of the same species or different species of the same genus.

In one embodiment, the pathogenic agent(s) will belong to at least one of the following groups: Bacteria and *Mycoplasma* agents including, but not limited to, pathogenic:

*Bacillus* spp., e.g., *Bacillus anthracis*; *Bartonella* spp., e.g., *B. quintana*; *Brucella* spp.; *Burkholderia* spp., e.g., *B. pseudomallei*; *Campylobacter* spp.; *Clostridium* spp., e.g., *C. tetani*, *C. botulinum*; *Coxiella* spp., e.g., *C. burnetii*; *Edwardsiella* spp., e.g., *E. tarda*; *Enterobacter* spp., e.g., *E. cloacae*; *Enterococcus* spp., e.g., *E. faecalis*, *E. faecium*; *Escherichia* spp., e.g., *E. coli*; *Francisella* spp., e.g., *F. tularensis*; *Haemophilus* spp., e.g., *H. influenzae*; *Klebsiella* spp., e.g., *K. pneumoniae*; *Legionella* spp.; *Listeria* spp., e.g., *L. monocytogenes*; Meningococci and Gonococci, e.g., *Neisseria* spp.; *Moraxella* spp.; *Mycobacterium* spp., e.g., *M. leprae*, *M. tuberculosis*; Pneumococci, e.g., *Diplococcus pneumoniae*; *Pseudomonas* spp., e.g., *P. aeruginosa*; *Rickettsia* spp., e.g., *R. prowazekii*, *R. rickettsii*, *R. typhi*; *Salmonella* spp., e.g., *S. typhi*; *Staphylococcus* spp., e.g., *S. aureus*; *Streptococcus* spp., including Group A Streptococci and hemolytic Streptococci, e.g., *S. pneumoniae*, *S. pyogenes*; *Streptomyces* spp.; *Shigella* spp.; *Vibrio* spp., e.g., *V. cholerae*; and *Yersinia* spp., e.g., *Y. pestis*, *Y. enterocolitica*. Fungus and Yeast agents including, but not limited to, pathogenic: *Alternaria* spp.; *Aspergillus* spp.; *Blastomyces* spp., e.g., *B. dermatiditis*; *Candida* spp., e.g., *C. albicans*; *Cladosporium* spp.; *Coccidiodes* spp., e.g., *C. immitis*; *Cryptococcus* spp., e.g., *C. neoformans*; *Histoplasma* spp., e.g., *H. capsulatum*; and *Sporothrix* spp., e.g., *S. schenckii*.

In one embodiment, the pathogenic agent(s) will be from a protist agent including, but not limited to, pathogenic: Amoebae, including *Acanthamoeba* spp., *Amoeba* spp., *Naegleria* spp., *Entamoeba* spp., e.g., *E. histolytica*; *Cryptosporidium* spp., e.g., *C. parvum*; *Cyclospora* spp.; *Encephalitozoon* spp., e.g., *E. intestinalis*; *Enterocytozoon* spp.; *Giardia* spp., e.g., *G. lamblia*; *Isospora* spp.; *Microsporidium* spp.; *Plasmodium* spp., e.g., *P. falciparum*, *P. malariae*, *P. ovate*, *P. vivax*; *Toxoplasma* spp., e.g., *T. gondii*; and *Trypanosoma* spp., e.g., *T. brucei*.

In one embodiment, the pathogenic agent(s) will be from a parasitic agent (e.g., helminthic parasites) including, but not limited to, pathogenic: *Ascaris* spp., e.g. *A. lumbricoides*; *Dracunculus* spp., e.g., *D. medinensis*; *Onchocerca* spp., e.g., *O. volvulus*; *Schistosoma* spp.; *Trichinella* spp., e.g., *T. spiralis*; and *Trichuris* spp., e.g., *T. trichiura*.

In another embodiment, the pathogenic agent(s) will be from a viral agent including, but not limited to, pathogenic: Adenoviruses; Arenaviruses, e.g., Lassa Fever viruses; Astroviruses; Bunyaviruses, e.g., Hantaviruses, Rift Valley Fever viruses; Coronaviruses, Deltaviruses; Cytomegaloviruses, Epstein-Barr viruses, Herpes viruses, Varicella viruses; Filoviruses, e.g., Ebola viruses, Marburg viruses; Flaviruses, e.g., Dengue viruses, West Nile Fever viruses, Yellow Fever viruses; Hepatitis viruses; Influenzaviruses; Lentiviruses, T-Cell Lymphotropic viruses, other leukemia viruses; Norwalk viruses; Papillomaviruses, other tumor viruses; Paramyxoviruses, e.g., Measles viruses, Mumps viruses, Parainfluenzaviruses, Pneumoviruses, Sendai viruses; Parvoviruses; Picornaviruses, e.g., Cardioviruses, Coxsackie viruses, Echoviruses, Poliomyelitis viruses, Rhinoviruses, Other Enteroviruses; Poxviruses, e.g., Variola viruses, Vaccinia viruses, Parapoxviruses; Reoviruses, e.g., Coltiviruses, Orbiviruses, Rotaviruses; Rhabdoviruses, e.g., Lyssaviruses, Vesicular Stomatitis viruses; and Togaviruses, e.g., Rubella viruses, Sindbis viruses, Western Encephalitis viruses.

In one particular embodiment, the antigenic peptide is selected from the group consisting of a Canine parvovirus peptide, *Bacillus anthracis* protective antigen (PA) antigenic peptide, and an Eastern Equine Encephalitis virus antigenic peptide. In a particular embodiment, the antigenic peptide is the *Bacillus antracis*-derived peptide with the amino acid sequence selected from PA1 (SEQ. ID. NO. 1), PA2 (SEQ. ID. NO. 2), PA3 (SEQ. ID. NO. 3), or PA4 (SEQ. ID. NO. 4).

Host-Cell Toxic Peptide

In another particular embodiment, the recombinant peptide is a peptide that is toxic to the host cell when in free monomeric form. In certain embodiments, the peptide of interest expressed in conjunction with a viral capsid will be a host cell toxic peptide. A host cell toxic peptide indicates a bio-inhibitory peptide that is biostatic, biocidal, or toxic to the host cell in which it is expressed, or to other cells in the cell culture or organism of which the host cell is a member, or to cells of the organism or species providing the host cells. In one embodiment, the host-cell-toxic peptide will be a bioinhibitory peptide that is biostatic, biocidal, or toxic to the host cell in which it is expressed. Some examples of host-cell-toxic peptides include, but are not limited to: peptide toxins, anti-microbial peptides, and other antibiotic peptides.

Antimicrobial Peptides

In another particular embodiment, the recombinant peptide is a peptide that is an antimicrobial peptide. Anti-Microbial Peptides include, e.g., anti-bacterial peptides such as, e.g., magainins, betadefensins, some alpha-defensins; cathelicidins; histatins; anti-fungal peptides; antiprotozoal peptides; synthetic AMPs; peptide antibiotics or the linear or pre-cyclized oligo- or poly-peptide portions thereof; other antibiotic peptides (e.g., anthelmintic peptides, hemolytic peptides, tumoricidal peptides); and anti-viral peptides (e.g., some alpha-defensins; virucidal peptides; peptides that inhibit viral infection). In one embodiment, the antimicrobial peptide is selected from the group consisting of D2A21 antimicrobial peptides.

Cells for Use in Expressing the VLP

The cell used as a host for the expression of the viral capsid or viral capsid fusion peptide (also referred to as "host cell") of the invention will be one in which the expression of viral capsid does not allow replication or infection of the cell. In one embodiment, the viral capsid will be derived from a virus that does not infect the specific species of cell that the host cell is derived from. For example, in one embodiment, the viral capsid is derived from an icosahedral plant virus and is expressed in a host cell of a plant species that is not the native trophic host of the virus. In another embodiment, the viral species infects mammals and the expression system includes a plant host cell. In an alternative embodiment, the virus is a trophic virus of the particular plant species utilized as a host cell for expressing the capsid-recombinant peptide fusion.

The plant host cell may be any plant cell from the *Tracheophyta, Euphyllophyta, Spermatophyta*, or *Angiospermophyta*. In a particular embodiment, the plant cell is a Monocot, including, but not limited to, members of, e.g.: *Arecaceae*, e.g., *Cocos* spp., *Elaeis* spp.; *Dioscoreaceae*, e.g., *Dioscorea* spp.; *Gramineae* (*Poaceae*), e.g., *Avena* spp., *Hordeum* spp., *Oryza* spp., *Panicum* spp., *Triticum* spp., *Zea* spp.; and *Musaceae*, e.g., *Musa* spp.

In an alternative embodiment, the plant cell is a member of the Dicots, including, but not limited to, e.g.: *Amaranthaceae*, e.g., *Amaranthus* spp., *Beta* spp., *Chenopodium* spp.; *Apiaceae* (*Umbelliferae*), e.g., *Daucus* spp., *Pastinaca* spp.; *Brassicaceae* (*Cruciferae*), e.g., *Arabidopsis* spp., *Brassica* spp.; *Compositae*, e.g., *Helianthus* spp.; *Convolvulaceae*, e.g., *Ipomoea* spp.; *Cucurbitaceae*, e.g., *Citrullus* spp., *Cucumis* spp., *Cucurbita* spp.; *Euphorbiaceae; Leguminosae* (*Fabaceae*), e.g, *Glycine* spp., *Lens* spp., *Medicago* spp., *Phaseolus* spp., *Pisum* spp., *Trifolium* spp., *Vicia* spp., *Vigna* spp.; *Linaceae*, e.g., *Linum* spp.; and *Solanaceae*, e.g, *Capsicum* spp., *Lycopersicon* spp., *Nicotiana* spp., *Solanum* spp.

In a particular embodiment, the host cell is selected from the group consisting of *Aradiposis thialiana, Taxus cuspidate, Catharanthus roseus, Nicotiana tabacum, Oryza sativa, Lycopersicum esculentum*, and *Glycine max*.

II. Nucleic Acid Constructs

The present invention further provides non-infectious nucleic acid constructs capable of stably integrating into the host cell's genome and encoding a fusion peptide of a capsid and a recombinant peptide. The fusion peptide can be operably linked to a promoter sequence and a termination sequence. In one embodiment, a nucleic acid construct for use in transforming plant host cells including a) a nucleic acid sequence encoding a recombinant peptide, and b) a nucleic acid sequence encoding a viral capsid is provided, wherein the nucleic acid of a) and the nucleic acid of b) are operably linked to form a fusion protein is stably inserted into the genome of the plant host cell, wherein it is expressed in the plant cell.

In certain embodiments, the vector can include sequence for multiple capsids, or for multiple peptides of interest. In one embodiment, the vector can include at least two different capsid-peptide coding sequences. In one embodiment, the coding sequences are linked to the same promoter. In certain embodiments, the coding sequences are separated by an internal ribosomal binding site. In other embodiments, the coding sequences are linked by a linker sequence that allows the formation of virus like particles in the cell. In another embodiment, the coding sequences are linked to different promoters. These promoters may be constitutive or driven by the same or different induction conditions. In another embodiment, multiple vectors capable of insertion into the genome and encoding different capsid-peptide combinations are provided. The multiple vectors can include promoters that are constitutive or driven by the same induction conditions, or by different induction conditions. In one embodiment, the viral capsid is derived from an icosahedral viral capsid.

The coding sequence for a peptide of interest can be inserted into the coding sequence for a viral capsid or capsid in a predetermined site. The peptide can also be inserted at a non-predetermined site and cells screened for production of VLPs. In one embodiment, the peptide is inserted into the capsid coding sequence so as to be expressed as a loop during formation of a VLP. In one embodiment, one peptide coding sequence is included in the vector, however in other embodiments, multiple sequences are included. The multiple sequences can be in the form of concatamers, for example concatamers linked by cleavable linker sequences.

Peptides may be inserted at more than one insertion site in a capsid. Thus, peptides may be inserted in more than one surface loop motif of a capsid; peptides may also be inserted at multiple sites within a given loop motif. The individual functional and/or structural peptide(s) of the insert(s), and/or the entire peptide insert(s), may be separated by cleavage sites, i.e. sites at which an agent that cleaves or hydrolyzes protein can act to separate the peptide(s) from the remainder of the capsid structure or assemblage.

Peptides may be inserted within external-facing loop(s) and/or within internal-facing loop(s), i.e. within loops of the capsid that face respectively away from or toward the center of the capsid. Any amino acid or peptide bond in a surface loop of a capsid can serve as an insertion for the peptide. Typically, the insertion site will be selected at about the center of the loop, i.e. at about the position located most distal from the center of the tertiary structure of the folded capsid peptide. The peptide coding sequence may be operably inserted within the position of the capsid coding sequence corresponding to this approximate center of the selected loop(s). This includes the retention of the reading frame for that portion of the peptide sequence of the capsid that is synthesized downstream from the peptide insertion site.

In another embodiment, the peptide can be inserted at the amino terminus of the capsid. The peptide can be linked to the capsid through one or more linker sequences, including the cleavable linkers described above. In yet another embodiment, the peptide can be inserted at the carboxy terminus of the capsid. The peptide can also be linked to the carboxy terminus through one or more linkers, which can be cleavable by chemical or enzymatic hydrolysis. In one embodiment, peptide sequences are linked at both the amino and carboxy termini, or at one terminus and at at least one internal location, such as a location that is expressed on the surface of the capsid in its three dimensional conformation.

In one embodiment, the peptide can be inserted into the capsid from a Cowpea Chlorotic Mosaic Virus. In one particular embodiment, the peptide can be inserted at amino acid 129 of the CCMV coat protein. In one embodiment, the peptide sequence can be inserted at amino acid 63, 102, 114, 129, or 160 of the CCMV coat protein. In another embodiment, the peptide sequence can be inserted at amino acids 60, 61, 62 or 63 of the CCMV coat protein. In still another embodiment, the peptide can be inserted at both amino acids 129 and amino acids 60-63 of the CCMV protein.

In a particular embodiment, the present invention provides a nucleic acid construct including a) a nucleic acid encoding an antigenic peptide, and b) a nucleic acid encoding a viral capsid, wherein the nucleic acid of a) and the nucleic acid of b) are operably linked to form a fusion protein when expressed in a cell. Other capsids and recombinant peptides useful in constructing the nucleic acid construct are disclosed above.

Promoters

In one embodiment, the nucleic acid construct includes a promoter sequence operably attached to the nucleic acid sequence encoding the capsid-recombinant peptide fusion peptide. An operable attachment or linkage refers to any configuration in which the transcriptional and any translational regulatory elements are covalently attached to the described sequence so that by action of the host cell, the regulatory elements can direct the expression of the sequence of interest. In alternative embodiment, the nucleic acid construct encoding the capsid fusion product can be inserted in frame with a host cell native promoter utilizing a gene trapping strategy.

In a fermentation process, once fermentation begins, it is ideal to have a high level of production in order to maximize efficiency of the expression system. The promoter initiates transcription and is generally positioned 1-100 nucleotides upstream of the transcription start site. Ideally, a promoter will be strong enough to allow for a large amount of recombinant peptide accumulation.

The promoters used in accordance with the present invention may be constitutive promoters or regulated promoters. Common examples of useful regulated promoters used in the art include: ethanol-inducible promoters; iron deficiency-inducible promoters; wound-inducible promoters; and hormone-inducible, e.g., auxin-inducible, promoters. Common examples of useful constitutive promoters include the ubiquitin promoter, the actin promoter, the tubulin promoter, and the Cassava Vein Mosaic Virus promoter. Other types of promoters useful in the present invention include tissue-specific promoters such as corn sucrose synthetase 1 (Yang et al., 1990), corn alcohol dehydrogenase 1 (Vogel et al., 1989), corn light harvesting complex (Simpson, 1986), corn heat shock protein (Odell et al., 1985), pea small subunit RuBP carboxylase (Poulsen et al., 1986; Cashmore et al., 1983), Ti plasmid mannopine synthase (Langridge et al., 1989), Ti plasmid nopaline synthase (Langridge et al., 1989), petunia chalcone isomerase (Van Tunen et al., 1988), bean glycine rich protein 1 (Keller et al., 1989), CaMV 35s transcript (Odell et al., 1985) and Potato patatin (Wenzler et al., 1989). Preferred promoters are the cauliflower mosaic virus (CaMV $^{35}$S) promoter, the rice alpha-amylase RAmy3D promoter, and the S-E9 small subunit RuBP carboxylase promoter. In addition, a variety of plant gene promoters that are regulated in response to environmental, hormonal, chemical, and/or developmental signals can be used for expression of an operably linked gene in plant cells, including promoters regulated by (1) heat (Callis et al., Plant Physiol. 88:965, 1988), (2) light (e.g., pea rbcS-3A promoter, Kuhlemeier et al., Plant Cell 1:471, 1989; maize rbcS promoter, Schaffner and Sheen, Plant Cell 3:997, 1991; or chlorophyll a/b-binding protein promoter, Simpson et al., EMBO J. 4:2723, 1985), (3) hormones, such as abscisic acid (Marcotte et al., Plant Cell 1:969, 1989), (4) wounding (e.g., wunI, Siebertz et al., Plant Cell 1:961, 1989); or (5) chemicals such as methyl jasmonate, salicylic acid, or Safener. It may also be advantageous to employ (6) organ-specific promoters (e.g., Roshal et al., EMBO J. 6:1155, 1987; Schernthaner et al., EMBO J. 7:1249, 1988; Bustos et al., Plant Cell 1:839, 1989). Additional promoters useful in the present invention include those described in WO 97/48819; the phaseolin promoters described in U.S. Pat. No. 5,591,605; rice actin promoters described in U.S. Pat. No. 5,641,876; the per 5 promoter described in WO 98/56921; the gamma zein promoters described in WO 00/12681; and other promoters as described in U.S. Pat. No. 6,825,006, U.S. Pat. No. 6,660,911, and plant promoters described the plant promoter sequence database PlantProm, described in Shahmuradov et al. (2003), "PlantProm: a database of plant promoter sequences," Nucleic Acid Res. 31(1): 114-117, and available at http://mendel.cs.rhul.ac.uk/mendel.php?topic=plantprom. Additional promoters may also include cauliflower mosaic virus (CaMV) 35S promoter or its enhanced version, the hybrid (ocs)$_3$mas promoter, and ubiquitin promoters from maize or *A. thaliana.*

A promoter having the nucleotide sequence of a promoter native to the selected plant host cell can also be used to control expression of the transgene encoding the target peptide. Tandem promoters may also be used in which more than one promoter is covalently attached to another, whether the same or different in sequence.

A promoter having the nucleotide sequence derived from a virus can also be used to direct expression of the transgene encoding the target peptide.

Regulated promoters can utilize promoter regulatory proteins in order to control transcription of the gene of which the promoter is a part. Where a regulated promoter is used herein, a corresponding promoter regulatory protein will also be part of an expression system according to the present invention. Many regulated-promoter/promoter-regulatory-protein pairs are known in the art.

Other Elements

Other regulatory elements can be included in a nucleic acid construct. Such elements include, but are not limited to, for example, transcriptional enhancer sequences, translational enhancer sequences, other promoters, activators, translational start and stop signals, transcription terminators, cistronic regulators, polycistronic regulators, tag sequences, such as nucleotide sequence "tags" and "tag" peptide coding sequences, which facilitates identification, separation, purification, or isolation of an expressed peptide, including His-tag, Flag-tag, T7-tag, S-tag, HSV-tag, B-tag, Strep-tag, polyarginine, polycysteine, polyphenylalanine, polyaspartic acid, (Ala-Trp-Trp-Pro)n, thioredoxin, beta-galactosidase, chloramphenicol acetyltransferase, cyclomaltodextrin gluconotransferase, CTP:CMP-3-deoxy-D-manno-octulosonate cytidyltransferase, trpE or trpLE, avidin, streptavidin, T7 gene 10, T4 gp55, Staphylococcal protein A, streptococcal protein G, GST, DHFR, CBP, MBP, galactose binding domain, Calmodulin binding domain, GFP, KSI, c-myc, ompT, ompA, pelB, NusA, ubiquitin, and hemosylin A.

In one embodiment, the nucleic acid construct further comprises a tag sequence adjacent to the coding sequence for the recombinant peptide of interest, or linked to a coding sequence for a viral capsid. In one embodiment, this tag sequence allows for purification of the protein. The tag sequence can be an affinity tag, such as a hexa-histidine affinity tag. In another embodiment, the affinity tag can be a glutathione-S-transferase molecule. The tag can also be a fluorescent molecule, such as YFP or GFP, or analogs of such fluorescent proteins. The tag can also be a portion of an antibody molecule, or a known antigen or ligand for a known binding partner useful for purification.

The present invention can include, in addition to the capsid-recombinant peptide coding sequence, the following regulatory elements operably linked thereto: a promoter, a transcription terminator, translational start and stop signals.

Further examples of translation and transcription elements, and other elements useful in the present invention are described in: J D Watson et al. (eds.), Recombinant DNA, pp. 273-92 (1992) (Scientific American Books, W. H. Freeman and Co., New York, N.Y., USA); and I Mitsuhara et al., "Efficient promoter cassettes for enhanced expression of foreign genes in dicotyledonous and monocotyledonous plants," *Plant Cell Physiol.* 37(1):49-59 (1996).

In one particular embodiment, the nucleic acid construct includes additional nucleic acid sequences derived from the 3' untranslated region (3' UTR) of the viral genomic nucleic acid sequence utilized to derive the viral capsid protein. In one particular embodiment, the 3'UTR contains sequences that play a role in regulation of translation or capsid formation in the wild type virus. In one embodiment, the 3'UTR sequences are upstream pseudoknot domains (UPD). See, for example, Leathers et al. (1993) "A phylogenetically conserved sequence within viral 3' untranslated RNA pseudoknots regulates translation," Mol. Cell Biol. 13(9): 5331-5347. In a particular embodiment, the 3'UTR are derived from the 3'UTR of the viral capsid encoding region of the viral genome. In a more particular embodiment, the 3'UTR is derived from the cowpea chlorotic mosaic virus RNA3 3' untranslated region. In one embodiment, the 3'UTR sequence includes an encapsidation signal.

In an alternative embodiment, the nucleic acid construct includes at least one encapsidation signal derived from a viral nucleic acid sequence. The encapsidation signal can be derived from 5'UTR, 3'UTR, or internal sequence of the viral genomic sequence. In one embodiment, the nucleic acid construct is encapsidated in the VLP.

In one embodiment, the non-infectious nucleic acid construct also includes other sequences derived from the viral or non-viral nucleic acid sequence other than the viral capsid protein sequence.

Vectors

Useful expression vectors for use in plant cells in stably integrating into the host cell genome and expressing capsid-recombinant peptide fusion peptides are constructed by inserting a structural DNA sequence encoding a desired target peptide fused with a capsid peptide together with suitable translation initiation and termination signals in operable reading phase with a functional promoter. The vector may also comprise one or more phenotypic selectable or screenable markers to allow for selection of host cells. Alternatively, the selectable or screenable markers can be provided on a separate plasmid.

A wide variety of vectors and/or carriers are known in the art as useful for transforming a target plant host cell with recombinant capsid-encoding nucleic acid for expression, and any of these may be used for expressing the genes according to the present invention. See, e.g., I J Goderis I J et al., "A set of modular plant transformation vectors allowing flexible insertion of up to six expression units," *Plant Mol. Biol.* 50(1):17-27 (2002); A H Christensen & P H Quail, "Ubiquitin promoter-based vectors for high-level expression of selectable and/or screenable marker genes in monocotyledonous plants," *Transgenic Res.* 5(3):213-18 (1996); J D Jones et al., "Effective vectors for transformation, expression of heterologous genes, and assaying transposon excision in transgenic plants," *Transgenic Res.* 1(6):285-97 (1992); A P Gleave A P, "A versatile binary vector system with a T-DNA organisational structure conducive to efficient integration of cloned DNA into the plant genome," *Plant Mol. Biol.* 20(6):1203-07 (1992).

Thus, plasmids, transposons, genomic DNA, genomic RNA, plant artificial chromosomes, and other nucleic acid vectors may be used. Examples of some vectors that may be used include, but are not limited to, pRT101, pRT101-MCS, pRT104, pRT104.24LS, pRT104.N-myc, pRT104.C-myc, pRT104.N-3HA, pRT104-N3HAdAsp, pRT104.N-6HA, pRT104-N6HAdAsp, pRT104.C-3HA, pRT104-GST, pRT104 NES(A2), pRT103-3HA, pRTd35S-Luci(-), pRTd35S-Luci-NES, pRTd35S-GFP, pRTd35S-GFP.SacI, pRTdS GFP.BglII, pRTd35S-Ds-Red, pRTd35S-profillin, pBIGal4 DBD, pRT-3HAxHsfA2 DBD, pRT-3HAxGal4 DBD, pUC, pIL-TAB, pET, pME, pBBR, and pROKII. When particle bombardment is used to introduce the vector into the cell, any DNA plasmid or DNA molecule may be utilized in the present invention.

In a particular embodiment, the vector is pIL-Tab. In a more particular embodiment, the vector is pIL-Tab encoding for the coat protein from Cowpea Chlorotic Mosaic Virus (CCMV). In a particular embodiment, the vector is pIL-Tab, and the heterologous peptide is selected from the group consisting of PA1, PA2, PA3 or PA4. In a still further embodiment, the vector is selected from the group consisting of pDOW2160 (Seq. ID. No. 5), pDOW 2161 (Seq. ID. No. 6), pDOW2162 (Seq. ID. No. 7), pDOW2163 (Seq. ID. No. 8), pDOW 2169 (Seq. ID. No. 9), pDOW2170 (Seq. ID. No. 10), pDOW2171 (Seq. ID. No. 11), and pDOW2172 (Seq. ID. No. 12).

Alternatively, or in addition, carriers may be used, such as liposomes, dendrimers, cationic polymers, and cationic polymer-lipid complexes, all of which have been employed in widely published methods for delivery of nucleic acids to cells or protoplasts. Alternatively, naked DNA or naked RNA may be delivered to the plant host.

The vector, carrier, or naked nucleic acid may be directly transformed into a plant cell or protoplast by any method known effective therefore in the art. For example, any of the following methods may be used to transform the plant target host with the recombinant capsid-encoding nucleic acid: *Agrobacterium* spp.; microparticle bombardment as described by V. Vasil et al., Bio/Technology 9, 743 (1991); electroporation of protoplasts as described, for example, for lettuce by M C Chupeau et al., Bio/Technology 7, 503 (1989); surface abrasion using, e.g., silicon carbide whiskers, glass, or carborundum; liposome fusion with protoplasts as described, for example, by A. Deshayes et al., EMBO J. 4, p. 2731-2737 (1985); cell-cell (protoplast-protoplast) fusion; and endogenous plant virus infection, i.e. transformation of the plant target host with an engineered virus vector, the engineered virus vector being of a type of virus for which the selected plant target host is its native host and wherein the virus has been engineered to contain a recombinant capsid-protein-encoding nucleic acid (wherein the capsid-protein-nucleic acid from which the recombinant is made is selected from a virus for which the plant target host is not its native host); polyethylene glycol mediated transformations as described by, for example, I. Potrykus et al., Mol. Gen. Genetics, 197, 183-188; and microinjection as described by, for example, R. Griesbach, Biotechnology 3, p. 348-350 and C K Shewmaker Mol. Gen. Genetics, 202 p. 179-185 (1986).

III. Expression of Capsid Fusion Products in Plant Cells

The present invention also provides a process for producing a recombinant peptide. The process includes:
  a) providing a plant cell;
  b) providing a non-infectious nucleic acid containing an expression cassette encoding a fusion peptide; wherein the fusion is of a recombinant peptide and an icosahedral capsid;
  c) expressing the nucleic acid in the plant cell, wherein the expression in the cell provides for in vivo assembly of the fusion peptide into virus like particles; and
  d) isolating the virus like particles.

The fusion peptide is operably linked to a promoter sequence and a terminator sequence. In one embodiment, the process further comprises: e) cleaving the recombinant peptide from the viral capsid protein. In still another embodiment, the process further comprises: f) isolating the recombinant peptide from step e. See, for example, FIG. 1.

Peptides may be expressed as single-copy peptide inserts within a capsid peptide (i.e. expressed as individual inserts from recombinant capsid peptide coding sequences that are mono-cistronic for the peptide) or may be expressed as di-, tri-, or multi-copy peptide inserts (i.e. expressed as concatemeric inserts from recombinant capsid peptide coding sequences that are poly-cistronic for the peptide; the concatemeric insert(s) may contain multiple copies of the same exogenous peptide of interest or may contain copies of different exogenous peptides of interest). Concatemers may be homo- or hetero-concatemers.

In one embodiment, the isolated virus like particle can be administered to a human or animal in a vaccine strategy.

In another embodiment, the nucleic acid construct can be co-expressed with another nucleic acid encoding a wild type capsid. In a particular embodiment, the co-expressed capsid/capsid-recombinant peptide fusion particles assemble in vivo to form a chimeric virus like particle. The chimeric VLP is a virus like particle including capsids or capsid-peptide fusions encoded by at least two different nucleic acid constructs.

In still another embodiment, the nucleic acid construct can be co-expressed with another nucleic acid encoding a different capsid-recombinant peptide fusion particle. In a particular embodiment, the co-expressed capsid fusion particles will assemble in vivo to form a chimeric virus like particle.

In still another embodiment, a second nucleic acid, which is designed to express a different peptide, such as a chaperone protein, can be expressed concomitantly with the nucleic acid encoding the fusion peptide.

The plant cells, capsids, and recombinant peptides useful for the present invention are discussed above.

In one embodiment, the expressed viral capsid-heterologous peptide fusion product is expressed in soluble form in the cell.

In one embodiment, the expressed viral capsid-recombinant heterologous fusion product is assembled into VLPs in the cell.

In a separate embodiment, a portion of the expressed viral capsid-heterologous peptide fusion product of interest is formed in an insoluble aggregate in the cell. In one embodiment, the peptide of interest can be renatured from the insoluble aggregate.

Cleavage of Peptide of Interest

In one embodiment, the process further provides: e) cleaving the fusion product to separate the recombinant peptide from the capsid.

A cleavable linkage sequence can be included between the viral protein and the recombinant peptide. Examples of agents that can cleave such sequences include, but are not limited to chemical reagents such as acids (HCl, formic acid), CNBr, hydroxylamine (for asparagine-glycine), 2-Nitro-5-thiocyanobenzoate, O-Iodosobenzoate, and enzymatic agents, such as endopeptidases, endoproteases, trypsin, clostripain, and Staphylococcal protease.

Cleavable linkage sequences are well known in the art. In the present invention, any cleavable linkage sequence recognized by cleavage agents, including dipeptide cleavage sequences such as Asp-Pro, can be utilized.

Expression

The process of the invention optimally leads to the increased production of desired capsid-fusion products in a plant host cell in the desired sequence and conformation. The increased production alternatively can be an increased level of desired peptide per gram of protein produced, per gram of host protein, or as a percentage of total recombinant peptide produced. The increased production can also be an increased level of recoverable peptide, such as soluble protein, produced per gram of recombinant or per gram of host cell protein. The increased production can also be any combination of increased total level and increased active or soluble level of protein.

The improved expression of recombinant protein can be through expression of the protein as a capsid fusion protein and subsequently inserted in VLPs. In certain embodiments, at least 60, at least 70, at least 80, at least 90, at least 100, at least 110, at least 120, at least 130, at least 140, at least 150, at least 160, at least 170, or at least 180 copies of a peptide of interest are expressed in each VLP. The VLPs can be produced and recovered from the cytoplasm, periplasm or extracellular medium of the host cell.

In another embodiment, the peptide can be insoluble in the cell. In certain embodiments, the soluble or insoluble peptide is produced in a particle formed of multiple capsids but not forming a native-type VLP. For example, a cage structure of as few as 3 viral capsids can be formed. In certain embodiments, the capsid structure includes more than one copy of a peptide of interest and in certain embodiments, includes at least ten, at least 20, or at least 30 copies. In certain embodiments, the peptide is formed in the vacuole of the plant cell.

The peptide or viral capsid sequence can also include one or more targeting sequences or sequences to assist purification. These can be an affinity tag. These can also be targeting sequences directing the assembly of capsids into a VLP.

Cell Growth

Transformation of the plant host cells with the vector(s) may be performed using any transformation methodology known in the art, and the plant host cells may be transformed as intact cells or as protoplasts. Exemplary transformation methodologies have been described above.

As used herein, the term "fermentation" includes both embodiments in which literal fermentation is employed and embodiments in which other, non-fermentative culture modes are employed. Fermentation may be performed at any scale. Any method generally known in the art may be utilized in fermentation. See, for example, Hellwig et al. (2004) "Plant cell cultures for the production of recombinant proteins," Nature Biotech 22(11): 1415-1422; Sajc et al. (2000) "Bioreactors for plant engineering: an outlook for further research," Biochem Engin. J. 4:89-99. In one embodiment, the fermentation medium may be selected from among any viable plant cell culture media. Optionally, additives to the medium can include, for example, PVP, BSA, NaCl, BrefeldinA, reducing manganese, pluronic antifoam, polyethylene glycol, gelatin, protease inhibitors, redox co-factors, and dimethylsulfoxide.

The expression system according to the present invention can be cultured in any fermentation format. For example, batch, fed-batch, semi-continuous, and continuous fermentation modes may be employed herein.

The expression systems according to the present invention are useful for transgene expression at any scale (i.e. volume) of fermentation. Thus, e.g., microliter-scale, centiliter scale, and deciliter scale fermentation volumes may be used; and 1 Liter scale and larger fermentation volumes can be used. In one embodiment, the fermentation volume will be at or above 1 Liter. In another embodiment, the fermentation volume will be at or above 5 Liters, 10 Liters, 15 Liters, 20 Liters, 25 Liters, 50 Liters, 75 Liters, 100 Liters, 200 Liters, 500 Liters, 1,000 Liters, 2,000 Liters, 5,000 Liters, 10,000 Liters or 50,000 Liters.

In the present invention, growth, culturing, and/or fermentation of the transformed host cells is performed within a temperature range permitting survival of the host cells, preferably a temperature within the range of about 4° C. to about 55° C., inclusive.

Cell Density (Packed Wet Cells)

Plant cell expressions systems according to the present invention can provide a cell density or comparable packed wet cell density of about from about 20 g/L (2% packed cell volume) to more than 550 g/L (55% packed cell volume). In one embodiment, the packed cell volume is between 2% to about 60%. In another embodiment, the packed cell volume is 2%, 5%, 10%, 15%, 20%, 25%, 35%, 40%, 50%, 55%, 60%, 70%, or 85%.

Isolation of VLP or Peptide of Interest

In certain embodiments, the invention provides a process for improving the recovery of peptides of interest by protection of the peptide during expression through linkage and co-expression with a viral capsid. In certain embodiments, the viral capsid fusion forms a VLP, which can be readily separated from the cell lysate.

The proteins of this invention may be isolated and purified to substantial purity by standard techniques well known in the art, including, but not limited to, PEG precipitation, ammonium sulfate or ethanol precipitation, acid extraction, anion or cation exchange chromatography, phosphocellulose chromatography, hydrophobic interaction chromatography, affinity chromatography, nickel chromatography, hydroxylapatite chromatography, reverse phase chromatography, lectin chromatography, preparative electrophoresis, detergent solubilization, selective precipitation with such substances as column chromatography, immunopurification methods, and others. For example, proteins having established molecular adhesion properties can be reversibly fused to a ligand. With the appropriate ligand, the protein can be selectively adsorbed to a purification column and then freed from the column in a relatively pure form. The fused protein can then be removed by enzymatic or other activity. In addition, protein can be purified using immunoaffinity columns or Ni-NTA columns. General techniques are further described in, for example, R. Scopes, Protein Purification: Principles and Practice, Springer-Verlag: N.Y. (1982); Deutscher, Guide to Protein Purification, Academic Press (1990); U.S. Pat. No. 4,511,503; S. Roe, Protein Purification Techniques: A Practical Approach (Practical Approach Series), Oxford Press (2001); D. Bollag, et al., Protein Methods, Wiley-Lisa, Inc. (1996); A K Patra et al., Protein Expr Purif, 18(2): p/182-92 (2000); and R. Mukhija, et al., Gene 165(2): p. 303-6 (1995). See also, for example, Ausubel, et al. (1987 and periodic supplements); Deutscher (1990) "Guide to Protein Purification," Methods in Enzymology vol. 182, and other volumes in this series; Coligan, et al. (1996 and periodic Supplements) Current Protocols in Protein Science Wiley/Greene, NY; and manufacturer's literature on use of protein purification products, e.g., Pharmacia, Piscataway, N.J., or Bio-Rad, Richmond, Calif. Combination with recombinant techniques allow fusion to appropriate segments, e.g., to a FLAG sequence or an equivalent which can be fused via a protease-removable sequence. See also, for example, Hochuli (1989) Chemische Industrie 12:69-70; Hochuli (1990) "Purification of Recombinant Proteins with Metal Chelate Absorbent" in Setlow (ed.) Genetic Engineering, Principle and Methods 12:87-98, Plenum Press, NY; and Crowe, et al. (1992) QIAexpress: The High Level Expression & Protein Purification System QUIAGEN, Inc., Chatsworth, Calif.

Similarly, the virus-like particles or cage-like structures can be isolated and purified to substantial purity by standard techniques well known in the art. Techniques for isolation of VLPs include, in addition to those described above, precipitation techniques such as polyethylene glycol or salt precipitation. Separation techniques include anion or cation exchange chromatography, size exclusion chromatograph, phosphocellulose chromatography, hydrophobic interaction chromatography, affinity chromatography, nickel chromatography, hydroxylapatite chromatography, reverse phase chromatography, lectin chromatography, preparative electrophoresis, immunopurification methods, centrifugation, ultracentrifugation, density gradient centrifugation (for example, on a sucrose or on a cesium chloride (CsCl) gradient), ultrafiltration through a size exclusion filter, and any other protein isolation methods known in the art.

The invention can also improve recovery of active recombinant peptides. Levels of active protein can be measured, for example, by measuring the interaction between an identified and a parent peptide, peptide variant, segment-substituted peptide and/or residue-substituted peptide by any convenient in vitro or in vivo assay. Thus, in vitro assays can be used to determine any detectable interaction between an identified protein and a peptide of interest, e.g. between enzyme and substrate, between hormone and hormone receptor, between antibody and antigen, etc. Such detection can include the measurement of calorimetric changes, changes in radioactivity, changes in solubility, changes in molecular weight as measured by gel electrophoresis and/or gel exclusion processes, etc. In vivo assays include, but are not limited to, assays to detect physiological effects, e.g. weight gain, change in electrolyte balance, change in blood clotting time, changes in clot dissolution and the induction of antigenic response. Generally, any in vivo assay can be used so long as a variable parameter exists so as to detect a change in the interaction between the identified and the peptide of interest. See, for example, U.S. Pat. No. 5,834,250.

Detection of the expressed protein is achieved by methods known in the art and includes, for example, radioimmunoassays, Western blotting techniques or immunoprecipitation.

An initial salt fractionation can separate many of the unwanted host cell proteins (or proteins derived from the cell culture media) from the recombinant protein of interest. One such example can be ammonium sulfate. Ammonium sulfate precipitates proteins by effectively reducing the amount of water in the protein mixture. Proteins then precipitate on the basis of their solubility. The more hydrophobic a protein is, the more likely it is to precipitate at lower ammonium sulfate concentrations. A typical protocol includes adding saturated ammonium sulfate to a protein solution so that the resultant ammonium sulfate concentration is between 20-30%. This concentration will precipitate the most hydrophobic of proteins. The precipitate is then discarded (unless the protein of interest is hydrophobic) and ammonium sulfate is added to the supernatant to a concentration known to precipitate the protein of interest. The precipitate is then solubilized in buffer and the excess salt removed if necessary, either through dialysis or diafiltration. Other methods that rely on solubility of proteins, such as cold ethanol precipitation, are well known to those of skill in the art and can be used to fractionate complex protein mixtures.

The molecular weight of a recombinant protein can be used to isolated it from proteins of greater and lesser size using ultrafiltration through membranes of different pore size (for example, AMICON™ or MILLIPORE™ filtration membranes). As a first step, the protein mixture can be ultrafiltered through a membrane with a pore size that has a lower molecular weight cut-off than the molecular weight of the protein of interest. The retentate of the ultrafiltration can then be ultrafiltered against a membrane with a molecular cut off greater than the molecular weight of the protein of interest. The recombinant protein will pass through the membrane into the filtrate. The filtrate can then be chromatographed.

Recombinant proteins can also be separated from other proteins on the basis of its size, net surface charge, hydrophobicity, and affinity for ligands. In addition, antibodies raised against proteins can be conjugated to column matrices and the proteins immunopurified. All of these methods are well known in the art. It will be apparent to one of skill that chromatographic techniques can be performed at any scale and using equipment from many different manufacturers (e.g., Pharmacia Biotech).

Renaturation and Refolding

Insoluble protein can be renatured or refolded to generate secondary and tertiary protein structure conformation. Protein refolding steps can be used, as necessary, in completing configuration of the recombinant product. Refolding and renaturation can be accomplished using an agent that is known in the art to promote dissociation/association of proteins. For example, the protein can be incubated with dithiothreitol followed by incubation with oxidized glutathione disodium salt followed by incubation with a buffer containing a refolding agent such as urea.

Recombinant protein can also be renatured, for example, by dialyzing it against phosphate-buffered saline (PBS) or 50 mM Na-acetate, pH 6 buffer plus 200 mM NaCl. Alternatively, the protein can be refolded while immobilized on a column, such as the Ni NTA column by using a linear 6M-1M urea gradient in 500 mM NaCl, 20% glycerol, and 20 mM Tris/HCl pH 7.4, containing protease inhibitors. The renaturation can be performed over a period of 1.5 hours or more. After renaturation the proteins can be eluted by the addition of 250 mM immidazole. Immidazole can be removed by a final dialyzing step against PBS or 50 mM sodium acetate pH 6 buffer plus 200 mM NaCl. The purified protein can be stored at room temperature, 4° C. or frozen at −20° C. to −80° C.

Other methods include, for example, those that may be described in M H Lee et al., Protein Expr. Purif., 25(1): p. 166-73 (2002), W. K. Cho et al., J. Biotechnology, 77(2-3): p. 169-78 (2000), Ausubel, et al. (1987 and periodic supplements), Deutscher (1990) "Guide to Protein Purification," Methods in Enzymology vol. 182, and other volumes in this series, Coligan, et al. (1996 and periodic Supplements) Current Protocols in Protein Science Wiley/Greene, NY, S. Roe, Protein Purification Techniques: A Practical Approach (Practical Approach Series), Oxford Press (2001); D. Bollag, et al., Protein Methods, Wiley-Lisa, Inc. (1996)

Active Peptide Analysis

Active proteins can have a specific activity of at least 20%, 30%, or 40%, and preferably at least 50%, 60%, or 70%, and most preferably at least 80%, 90%, or 95% that of the native peptide that the sequence is derived from. Further, the substrate specificity ($k_{cat}/K_m$) is optionally substantially similar to the native peptide. Typically, $k_{cat}/K_m$ will be at least 30%, 40%, or 50%, that of the native peptide; and more preferably at least 60%, 70%, 80%, or 90%. Methods of assaying and quantifying measures of protein and peptide activity and substrate specificity ($k_{cat}/K_m$), are well known to those of skill in the art.

The activity of a recombinant peptide produced in accordance with the present invention by can be measured by any protein specific conventional or standard in vitro or in vivo assay known in the art. The activity of the plant cell host produced recombinant peptide can be compared with the activity of the corresponding native protein to determine whether the recombinant protein exhibits substantially similar or equivalent activity to the activity generally observed in the native peptide under the same or similar physiological conditions.

The activity of the recombinant protein can be compared with a previously established native peptide standard activity. Alternatively, the activity of the recombinant peptide can be determined in a simultaneous, or substantially simultaneous, comparative assay with the native peptide. For example, an in vitro assays can be used to determine any detectable interaction between a recombinant peptide and a target, e.g. between an expressed enzyme and substrate, between expressed hormone and hormone receptor, between expressed antibody and antigen, etc. Such detection can include the measurement of colorimetric changes, proliferation changes, cell death, cell repelling, changes in radioactivity, changes in solubility, changes in molecular weight as measured by gel electrophoresis and/or gel exclusion methods, phosphorylation abilities, antibody specificity assays such as ELISA assays, etc. In addition, in vivo assays include, but are not limited to, assays to detect physiological effects of the plant host cell produced peptide in comparison to physiological effects of the native peptide, e.g. antigenic response. Generally, any in vitro or in vivo assay can be used to determine the active nature of the recombinant peptide that allows for a comparative analysis to the native peptide so long as such activity is assayable. Alternatively, the peptides produced in the present invention can be assayed for the ability to stimulate or inhibit interaction between the peptide and a molecule that normally interacts with the peptide, e.g. a substrate or a component of the signal pathway that the native protein normally interacts. Such assays can typically include the steps of combining the protein with a substrate molecule under conditions that allow the peptide to interact with the target molecule, and detect the biochemical consequence of the interaction with the protein and the target molecule.

Assays that can be utilized to determine peptide activity are described, for example, in Ralph, P. J., et al. (1984) J. Immunol. 132:1858 or Saiki et al. (1981) J. Immunol. 127:1044, Steward, W. E. II (1980) The Interferon Systems. Springer-Verlag, Vienna and New York, Broxmeyer, H. E., et al. (1982) Blood 60:595, "Molecular Cloning: A Laboratory Manual", 2d ed., Cold Spring Harbor Laboratory Press, Sambrook, J., E. F. Fritsch and T. Maniatis eds., 1989, and "Methods in Enzymology: Guide to Molecular Cloning Techniques", Academic Press, Berger, S. L. and A. R. Kimmel eds., 1987, AK Patra et al., Protein Expr Purif, 18(2): p/182-92 (2000), Kodama et al., J. Biochem. 99: 1465-1472 (1986); Stewart et al., Proc. Nat'l Acad. Sci. USA 90: 5209-5213 (1993); (Lombillo et al., J. Cell Biol. 128:107-115 (1995); (Vale et al., Cell 42:39-50 (1985).

EXAMPLES

Viral Source of Coat Protein-Encoding Nucleic Acid

In the following examples, the cowpea chlorotic mottle virus (CCMV) has been used as the source of the coat protein for expression of the desired recombinant peptides. CCMV is a member of the bromovirus group of the Bromoviridae. Bromoviruses are 25-28 nm diameter icosahedral viruses with a four-component, positive sense, single-stranded RNA genome. RNA1 and RNA2 code for replicase enzymes. RNA3 codes for a protein involved in viral movement within plant hosts. RNA4 (a subgenomic RNA derived from RNA 3), i.e. sgRNA4, codes for the 20 kDa coat protein (CP) (SEQ ID NO:13) (Table 1). Each CCMV particle contains 180 copies of the CCMV CP. An exemplary DNA sequence encoding the CCMV CP is shown in SEQ ID NO:14 (Table 2).

TABLE 1

Wild type CCMV coat protein encoded by sgRNA4 (Seq. ID No. 13)

| | | | | | | | | | | | | | | | | | |
|---|---|---|---|---|---|---|---|---|---|---|---|---|---|---|---|---|---|
| Met | Ser | Thr | Val | Gly | Thr | Gly | Lys | Leu | Thr | Arg | Ala | Gln | Arg | Arg | Ala | Ala | Ala | Arg | Lys |
| Asn | Lys | Arg | Asn | Thr | Arg | Val | Val | Gln | Pro | Val | Ile | Val | Glu | Pro | Ile | Ala | Ser | Gly | Gln |
| Gly | Lys | Ala | Ile | Lys | Ala | Trp | Thr | Gly | Tyr | Ser | Val | Ser | Lys | Trp | Thr | Ala | Ser | Cys | Ala |
| Ala | Ala | Glu | Ala | Lys | Val | Thr | Ser | Ala | Ile | Thr | Ile | Ser | Leu | Pro | Asn | Glu | Leu | Ser | Ser |
| Glu | Arg | Asn | Lys | Gln | Leu | Lys | Val | Gly | Arg | Val | Leu | Leu | Trp | Leu | Gly | Leu | Leu | Pro | |

TABLE 1-continued

Wild type CCMV coat protein encoded by sgRNA4 (Seq. ID No. 13)

Ser Val Ser Gly Thr Val Lys Ser Cys Val Thr Glu Thr Gln Thr Thr Ala Ala Ala Ser

Phe Gln Val Ala Leu Ala Val Ala Asp Asn Ser Lys Asp Val Val Ala Ala Met Tyr Pro

Glu Ala Phe Lys Gly Ile Thr Leu Glu Gln Leu Thr Ala Asp Leu Thr Ile Tyr Leu Tyr

Ser Ser Ala Ala Leu Thr Glu Gly Asp Val Ile Val His Leu Glu Val Glu His Val Arg

Pro Thr Phe Asp Asp Ser Phe Thr Pro Val Tyr

TABLE 2

Exemplary DNA Sequence Encoding the CCMV CP (Seq. ID. No. 14)

atg tct aca gtc gga aca ggg aag tta act cgt gca caa cga agg gct gcg gcc cgt aag aac aag cgg aac act cgt gtg gtc caa cct gtt att gta gaa ccc atc gct tca ggc caa ggc aag gct att aaa gca tgg acc ggt tac agc gta tcg aag tgg acc gcc tct tgc gcg gcc gcc gaa gct aaa gta acc tcg gct ata act atc tct ctc cct aat gag cta tcg tcc gaa agg aac aag cag ctc aag gta ggt aga gtt tta tta tgg ctt ggg ttg ctt ccc agt gtt agt ggc aca gtg aaa tcc tgt gtt aca gag acg cag act act gct gct gcc tcc ttt cag gtg gca tta gct gtg gcc gac aac tcg aaa gat gtt gtc gct gct atg tac ccc gag gcg ttt aag ggt ata acc ctt gaa caa ctc acc gcg gat tta acg atc tac ttg tac agc agt gcg gct ctc act gag ggc gac gtc atc gtg cat ttg gag gtt gag cat gtc aga cct acg ttt gac gac tct ttc act ccg gtg tat tag The crystal structure of CCMV has been solved. This structure provides a clearer picture of the coat protein interactions that appear to be critical to particle stability and dynamics and has been helpful in guiding rational design of insertion sites. Previous studies have demonstrated that CCMV coat proteins can be genetically modified to carry heterologous peptides without interfering with their ability to form particles. A number of suitable insertion sites have been identified. A total of up to 180 copies of a heterologous peptide unit (whether as individual peptide units or in concatameric units) can be inserted into the CCMV particle at a single insertion site in the CCMV CP. Insertion sites identified within CCMV CP to date can accommodate peptides of various lengths.

Materials and Methods

Unless otherwise noted, standard techniques, vectors, control sequence elements, and other expression system elements known in the field of molecular biology are used for nucleic acid manipulation, transformation, and expression. Such standard techniques, vectors, and elements can be found, for example, in: Ausubel et al. (eds.), *Current Protocols in Molecular Biology* (1995) (John Wiley & Sons); Sambrook, Fritsch, & Maniatis (eds.), *Molecular Cloning* (1989) (Cold Spring Harbor Laboratory Press, NY); Berger & Kimmel, *Methods in Enzymology* 152: Guide to Molecular Cloning Techniques (1987) (Academic Press); and Bukhari et al. (eds.), DNA Insertion Elements, Plasmids and Episomes (1977) (Cold Spring Harbor Laboratory Press, NY).

Unless noted otherwise, PCR reactions were performed using a PTC225 thermocycler (MJ Research, South San Francisco, Calif., USA) according to the following protocol:

TABLE 3

PCR protocol

| Reaction Mix (100 μL total volume) | | Thermocycling Steps | | |
|---|---|---|---|---|
| 10 μL | 10× PT HIFI buffer* | Step 1 | 1 Cycle | 2 min. 94° C. |
| 4 μL | 50 mM MgSO₄* | Step 2 | 35 Cycles | 30 sec. 94° C. |
| 2 μL | 10 mM dNTPs* | | | 30 sec. 55° C. |
| 0.25 ng | Each Primer | | | 1 min. 68° C. |
| 1-5 ng | Template DNA | Step 3 | 1 Cycle | 10 min. 70° C. |
| 1 μL | PT HIFI Taq DNA Polymerase* | Step 4 | 1 Cycle | Maintain 4° C. |
| Remainder | Distilled De-ionized H₂O (ddH₂O) | | | |

*(from Invitrogen Corp, Carlsbad, CA, USA, hereinafter "Invitrogen")

Example 1

Production of Antigenic Peptides in CCMV Virus Particles in Whole Cowpea Plants Inoculated with CCMV RNA1, RNA2, and Chimeric RNA3

Expression of *Bacillus anthracis* antigenic peptides was performed in whole plants, using cowpea chlorotic mottle virus (CCMV) with capsid proteins (CP) engineered to contain one of four different antigenic peptides.

DNA having the nucleotide sequence of CCMV RNA 1 and DNA having the nucleotide sequence of CCMV RNA 2 were each separately subcloned in the cloning vector pUC19 downstream from, and under the control of, a T7 promoter and upstream from a unique Xba I site. This produced plasmids pDOW2122 (CCMV RNA1) and pDOW2123 (CCMV RNA2).

DNA having the nucleotide sequence of CCMV RNA 3, engineered to contain five BamH I restriction enzyme cleavage sites, was further engineered for production of the recombinant capsid protein-encoding nucleic acid. Four DNA molecules, each encoding a different one of four exogenous peptides (four different antigenic peptides from *Bacillus anthracis* Protective Antigen PA) were each synthesized by SOE (splicing-by-overlap-extension) of synthetic oligonucleotides. The resulting nucleic acids contained BamHI recognition site termini. Each PA DNA fragment was restricted with BamHI restriction enzyme and independently inserted into the coat protein at one of the five different engineered restriction enzyme cleavage sites in the CCMV coat protein coding sequence: BamHI at codon 63, BamHI at codon 102, BamHI at codon 114, BamHI at codon 129, and BamHI at codon 160.

The four different peptides were PA1 (SEQ ID NO: 1 encoded by SEQ ID NO: 15), PA2 (SEQ ID NO: 2, encoded by SEQ ID NO: 16), PA3 (SEQ ID NO: 3, encoded by SEQ ID NO:17), and PA4 (SEQ ID NO:4, encoded by SEQ ID NO: 18).

RNA3-CP63BamHI-PA1), pDOW2139 (pUC-CCMV-RNA3-CP102BamHI-PA1), pDOW2143 (pUC-CCMV-RNA3-CP114BamHI-PA1), pDOW2147 (pUC-CCMV-RNA3-CP129BamHI-PA1), and pDOW2151 (pUC-CCMV-RNA3-CP160BamHI-PA1) are examples of chimeric RNA3 having a PA1 insert at position 63, 102, 114, 129, and 160. Wild-type CCMV coat protein-encoding RNA 3 and engineered CCMV coat protein-encoding RNA 3 containing BamHI restriction site but no inserts were used as controls. Each modified RNA3 construct was separately sub-cloned in the cloning vector pUC19 downstream from and under the control of a T7 promoter, and upstream from a unique Xba I site.

Each of the three classes of plasmids was cloned in *E. coli*. Plasmids were isolated, linearized by Xba I restriction enzyme digestion, and then one microgram of each was transcribed into RNA in vitro using a MMESSAGE MMACHINE™ T7 NA transcription kit (Ambion, Inc., Austin, Tex., USA). This produced 24 different RNA varieties: one for RNA1, one for RNA2, 20 for chimeric RNA3, and two for RNA3 controls.

Cocktail mixes of RNA1, RNA2, RNA3 or chimeric RNA3s containing a PA insert were used to infect cowpea plants. Cowpea plants were sprouted from Cowpea California Blackeye #5 seeds (Ferry-Morse Seed Co. KY). Sprouts were transplanted singly into 6 inch pots with MIRACLE-GRO™ potting mix (Miracle-Gro Lawn Products OH). Cowpea plants were infected at 2-leaf stage (approximately 7 days post germination). A dusting of Carborundum powder 400grit (Fisher Scientific cat.409-21-2) was applied onto one leaf of

TABLE 4

*Bacillus anthracis* antigenic nucleic acid and amino acid sequences.

PA1
Nucleic Acid Sequence 5'-agt aat tct cgt aag aaa cgt tct acc tct gct ggc cct acc
(SEQ ID NO: 15)       gtg cct gat cgt gat aat gat ggc att cct gat-3'

Amino Acid Sequence   Ser Asn Ser Arg Lys Lys Arg Ser Thr Ser Ala Gly Pro
(SEQ ID NO: 1)        Thr Val Pro Asp Arg Asp Asn Asp Gly Ile Pro Asp PA2
Nucleic Acid Sequence 5'-agt cct gaa gct cgt cat cct ctc gtg gct gcg tat cct att
(SEQ ID NO: 16)       gtg cat gtt gat atg gaa aat att atc ctc tct-3'

Amino Acid Sequence   Ser Pro Glu Ala Arg His Pro Leu Val Ala Ala Tyr Pro
(SEQ ID NO: 2)        Ile Val His Val Asp Met Glu Asn Ile Ile Leu Ser PA3
Nucleic Acid Sequence 5'-cgt att att ttc aat ggc aaa gat ctc aat ctc gtg gaa cgt
(SEQ ID NO: 17)       cgt att gct gct gtg aat cct tct gat cct ctc-3'

Amino Acid Sequence   Arg Ile Ile Phe Asn Gly Lys Asp Leu Asn Leu Val Glu
(SEQ ID NO: 3)        Arg Arg Ile Ala Ala Val Asn Pro Ser Asp Pro Leu PA4
Nucleic Acid Sequence 5'-cgt caa gat ggc aaa acc ttc att gat ttc aaa aag tat aat
(SEQ ID NO: 18)       gat aaa ctc cct ctc tat att tct aat cct aat-3'

Amino Acid Sequence   Arg Gln Asp Gly Lys Thr Phe Ile Asp Phe Lys Lys
(SEQ ID NO: 4)        Tyr Asn Asp Lys Leu Pro Leu Tyr Ile Ser Asn Pro Asn Each of these was inserted into each of the five plasmids: pDOW2125 (pUC-CCMV RNA3-CP63BamHI), pDOW2126 (pUC-CCMV-RNA3-102BamHI), pDOW2127 (pUC-CCMV-RNA3-CP114BamHI), pDOW2128 (pUC-CCMV-RNA3-CP129BamHI), and pDOW2129 (pUC-CCMV-RNA3-CP160BamHI) which had been digested with BamHI restriction enzyme and then dephoshorylated.

This produced a total of 20 different versions of DNA for "chimeric RNA 3." Plasmids pDOW2135 (pUC-CCMVeach plant. RNA cocktail mixes were applied onto the carborundum layer. Leaves were abraded by gentle rubbing with a gloved finger. Infections were established 7-14 days post inoculation.

Unexpectedly, in this whole plant system, even though the native host plant was used, the chimeric coat proteins reverted to the wild type or in some cases, the desired exogenous antigen peptide was partially deleted. This was verified by sequencing the virus progeny. The RNA was extracted and reverse-transcribed into DNA using THERMOSCRIPT™ RT-PCR reverse transcription system (Invitrogen cat.11146-024) and CCMVRNA4.R gene specific primer (SEQ ID NO:19) (5'-CTC GAG CTA ATA CAC CGG AGT GAA AG-3'). cDNAs were further amplified by PCR using primers CCMVRNA4.F (SEQ ID NO:20) (5'-CTG CAG ATG TCT ACA GTC GGA ACA GG-3') and CCMVRNA4.R. The reactions were purified and sequenced with CCMV-CP-F1 primer, (SEQ ID NO: 21) (5'-AAC CCA TCG CTT CAG GCC AA-3'). Sequences were analyzed using a DNA sequencing program (SEQUENCHER™ software version 4.0.5, Gene Codes Corporation). For example, upon sequencing of RNA3 progeny derived from pDOW2128 containing the PA1 insert, the coat protein contained a small, unrecognized nucleotide insert (5'-CGTATTTCTGATCCTCTC-3') that was translated as RISDPL instead of the PA1 insert amino acid sequence. The inserted nucleotide sequence kept the rest of the coat protein in frame. It has been determined that the engineered CCMV RNA3 is unstable upon expression in the whole plant, easily undergoes recombinations, and that the whole plant system is not useful for production of epitopes on chimeric CCMV virus particles.

Example 2

Production of Antigenic Peptides in CCMV Virus Particles in Tobacco Suspension Culture Inoculated with CCMV RNA1, RNA2, and Chimeric RNA3

Expression of the same CCMV-peptide-encoding constructs was performed in plant cell suspension culture. *Nicotiana tabacum* NT1 cells were transfected by electroporation with RNA transcripts of CCMV RNA 3 coding for the chimeric CCMV coat proteins and CCMV RNA 1 and 2 coding for the replicase genes. Wild-type CCMV coat protein-encoding RNA 3 and engineered CCMV coat protein-encoding RNA 3 containing the appropriate BamHI restriction site but no inserts were used as controls.

24 different RNA varieties were obtained by in vitro RNA transcription as described in the Example 1: one for RNA1, one for RNA2, 20 for chimeric RNA3, and two for RNA3 controls. In 22 different groups, two micrograms of each of three resulting RNAs (RNA1, RNA2, and one of the RNA3s) were transformed into tobacco cells by electroporation.

The Following Protocol was Used for Plant Cell Transfection:
1) Media Preparation:
NTI Media (1 Liter):
4.33 g Murashige & Skoog basal salt (Phyto Technology Laboratories KS cat.M524), 100 mg Myo-Inositol (Sigma cat.I-3011), 1 ml of 1 mg/ml solution of Thiamine HCl (Sigma cat. T-3902), 180 mg Potassium Phosphate Monobasic $KH_2PO_4$ (Sigma cat. P-8416), 30 g Sucrose (Sigma cat.S-5390), and 200 µl 2,4-D solution of 10 mg/ml (Sigma cat. D-7299) were mixed in a small amount of water. Purified water was added to the solution to bring volume up to 1 liter. The pH was adjusted to 5.8, and the solution was autoclaved.

Mannitol Wash Solution 0.4M:
36.43 Mannitol (Sigma cat. M-1902) was added to small amount of purified water. Purified water was added to bring volume up to 500 ml and the pH was adjusted to 5.5. The solution was autoclaved in order to sterilize.

Enzyme Solution:
0.4M mannitol, and 0.02M MES were mixed in a small amount of water. Purified water was added to bring volume up to 500 ml and the pH was adjusted to 5.5. The solution was autoclaved in order to sterilize, and the solution was stored at 4° C. Prior to use, 1% cellulase (CELLULYSIN™, Calbiochem cat.219466) and 0.3% pectinase (MACERASE™, Calbiochem cat.441201) was added to solution, and the solution was shaken until the cellulase and pectinase were dissolved.

Electroporation Buffer:
0.8% NaCl, 0.02% KCl, 0.02% $KH_2PO_4$, and 0.11% $Na_2HPO_4$ were added to a small amount of purified water. Purified water was added to bring the solution up to 100 mls, and the pH was adjusted to 6.5. The buffer was autoclaved and stored at 4° C.

2) Tobacco Cell Partial Digestion Protocol:
Tobacco cell line NT 1 was partially digested prior to electroporation as following. A robust cell line was maintained by sub-culturing weekly, cells were grown in NTI media at 24° C. or 28° C. with gentle shaking, and three days before digestion, 5 ml of cell suspension was sub-cultured into 50 ml of NTI media and incubated at 28° C. Cells were spun down in 50 ml tubes for 5 minutes at 800 rpm. The enzyme solution was prepared, and cells were washed in the mannitol wash solution (approx. 40 ml). Cells were spun for 5 minutes at 800 rpm, and 3 volumes of enzyme solution were added to the cells. Cells were resuspended by inversion; transferred into 10 cm petri dishes by pouring, and the dish was shaken very slowly at room temperature while wrapped in aluminum foil for 60-120 minutes. The cells were then transferred back into 50 ml plastic tubes; and spun for 5 minutes at 800 rpm. Cells were washed with 40 ml mannitol wash solution and spun again, washed with electroporation buffer, and spun. Three volumes of electroporation buffer (total volume is usually 20 ml) were added to the cells; and the cells were stored at 4° C. wrapped in aluminum foil.

3) Electroporation of Partially Digested Cells Protocol:
1 ml of digested cells were aliquoted into electroporation cuvettes (4 mm gap). 2 µg each RNA transcript—CCMV RNA1, RNA2, and Chimeric RNA3—were added to the cuvettes and placed on ice for 5 minutes. 10 ml of NTI plating media were added (NTI+0.4M mannitol) to each Petri dish. The cells were electroporated at 500 µF, 250V, and the cuvettes were placed back on ice. The cells were then transferred into Petri dishes, and incubate at room temperature in darkness with no shaking. The cells were then collected for analysis at 48 hours post transfection.

Results
Expression of chimeric coat protein was analyzed by Western blot using anti-CCMV coat protein polyclonal antibody. Also, RNA was extracted from each of the cultures and the chimeric CCMV RNA4 was reverse transcribed into cDNA, which was then amplified by PCR. The PCR products were sequenced as described in Example 1. All samples were positive on the western blot except for the negative control that was transfected with only RNA1 and 2.

Compared to control CCMV capsid proteins, the chimeric coat proteins had greater size and slower mobility on the gel indicating that the chimeric coat proteins contained PA inserts. This was verified by sequencing of the viral RNA progeny. Results demonstrated that 19 out of 20 chimeric constructs expressed the chimeric CCMV coat protein properly without mutation in the desired antigen peptide. The results indicate that chimeric CCMV RNA3s expressed in suspension cells are stable.

Figure 2:
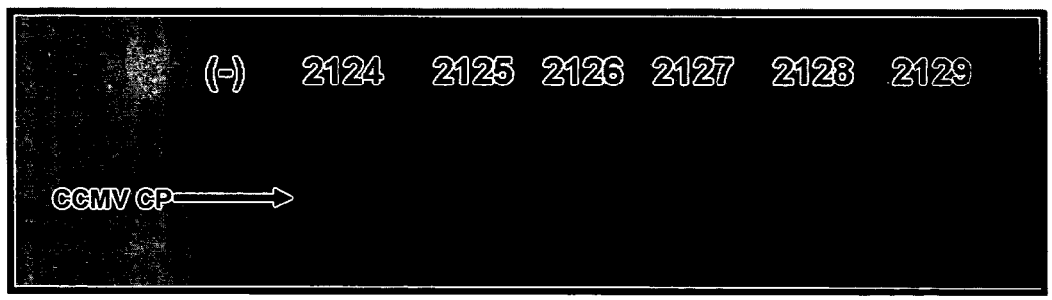
FIG. 2 shows expression of CCMV CP in tobacco NT1 cells transfected with infectious CCMV RNA1, RNA2, and one of the RNA3s transcribed from pDOW2124 (CCMV-RNA3-CP), pDOW2125 (CCMV-RNA3-CP63BamHI), pDOW2126 (CCMV-RNA3-CP102BamHI), pDOW2127 (CCMV-RNA3-CP114BamHI), pDOW2128 (CCMV-RNA3-CP129BamHI), and pDOW2129 (CCMV-RNA3-CP160BamHI). The plant cell extracts were run on SDS-PAGE gel and probed with anti-CCMV polyclonal antibodies. Lane 1 represents Buffer only, Lane 2 represents RNA1 and RNA2 only, Lane 3 represents RNA1 and RNA2+wt RNA3 transcribed from pDOW2124, Lane 4 represents RNA1 and RNA2+RNA3 transcribed from pDOW2125, Lane 5 represents RNA1 and RNA2+RNA3 transcribed from pDOW2126, Lane 6 represents RNA1 and RNA2+RNA3 transcribed from pDOW2127, Lane 7 represents RNA1 and RNA2+RNA3 transcribed from pDOW2128, Lane 8 represents RNA1 and RNA2+RNA3 transcribed from pDOW2129.

FIG. 2 shows the expression of CCMV CP in cells transfected with CCMV RNA1, RNA2, and RNA3 transcribed from pDOW2125 (CCMV63BamHI), pDOW2126 (CCMV102BamHI), pDOW2127 (CCMV114BamHI), pDOW2128 (CCMV129BamHI) and pDOW2129 (CCMV160BamHI). The results demonstrate that CCMV CP is expressed from all RNA3s with engineered BamHI site in different positions in the CP.

Figure 3:
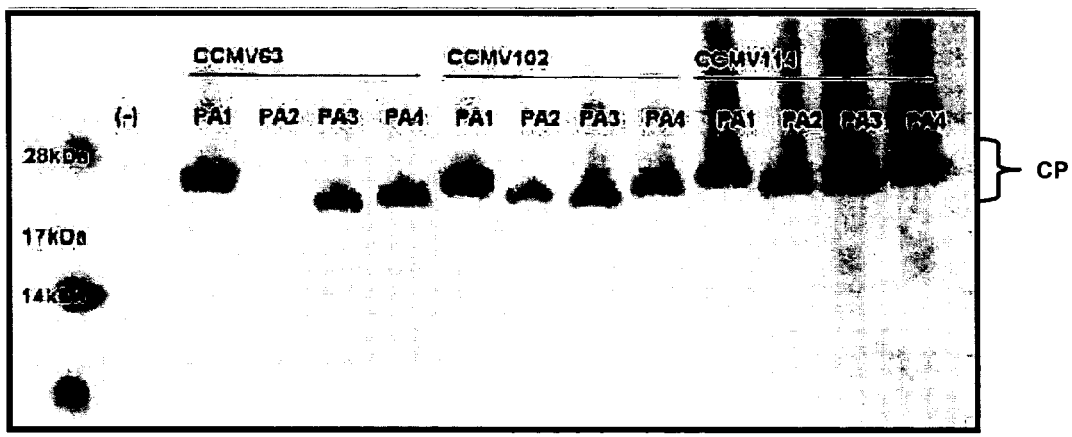
FIG. 3 shows expression of CCMV CP in tobacco NT1 cells transfected with infectious CCMV RNA1, RNA2, and one of the engineered RNA3s containing the CCMV CP fusion with antigenic peptide PA1, PA2, PA3, or PA4 at the position 63, 102, or 114. The plant cell extracts were run on SDS-PAGE gel and probed with anti-CCMV polyclonal antibodies. Lane 1 represents a size marker, Lane 2 represents Buffer only, Lane 3 represents RNA1+RNA2+chimeric RNA3 with PA1 in CP at position 63, Lane 4 represents RNA1+RNA2+chimeric RNA3 with PA2 in CP at position 63, Lane 5 represents RNA1+RNA2+chimeric RNA3 with PA3 in CP at position 63, Lane 6 represents RNA1+RNA2+chimeric RNA3 with PA4 in CP at position 63, Lane 7 represents RNA1+RNA2+chimeric RNA3 with PA1 in CP at position 102, Lane 8 represents RNA1+RNA2+chimeric RNA3 with PA2 in CP at position 102, Lane 9 represents RNA1+RNA2+chimeric RNA3 with PA3 in CP at position 102, Lane 10 represents RNA1+RNA2+chimeric RNA3 with PA4 in CP at position 102, Lane 11 represents RNA1+RNA2+chimeric RNA3 with PA1 in CP at position 114, Lane 12 represents RNA1+RNA2+chimeric RNA3 with PA2 in CP at position 114, Lane 13 represents RNA1+RNA2+chimeric RNA3 with PA3 in CP at position 114, and Lane 14 represents RNA1+RNA2+chimeric RNA3 with PA4 in CP at position 114.
Figure 4:
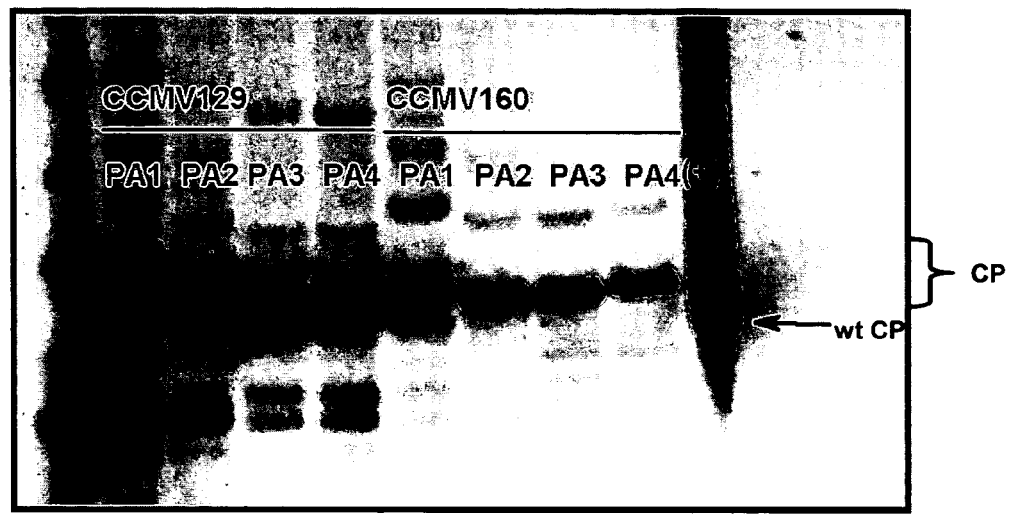
FIG. 4 shows expression of CCMV CP in tobacco NT1 cells transfected with infectious CCMV RNA1, RNA2, and one of the engineered RNA3s containing the CCMV CP fusion with antigenic peptide PA1, PA2, PA3, or PA4 at the position 129 or 160. The plant cell extracts were run on SDS-PAGE gel and probed with anti-CCMV polyclonal antibodies. Lane 1 represents a size marker, Lane 2 represents RNA1+RNA2+chimeric RNA3 with PA1 in CP at position 129, Lane 3 represents RNA1+RNA2+chimeric RNA3 with PA2 in CP at position 129, Lane 4 represents RNA1+RNA2+chimeric RNA3 with PA3 in CP at position 129, Lane 5 represents RNA1+RNA2+chimeric RNA3 with PA4 in CP at position 129, Lane 6 represents RNA1+RNA2+chimeric RNA3 with PA1 in CP at position 160, Lane 7 represents RNA1+RNA2+chimeric RNA3 with PA2 in CP at position 160, Lane 8 represents RNA1+RNA2+chimeric RNA3 with PA3 in CP at position 160, Lane 9 represents RNA1+RNA2+chimeric RNA3 with PA4 in CP at position 160, Lane 10 represents RNA1+RNA2+wt RNA3, and Lane 11 represents Buffer only.
Figure 5:
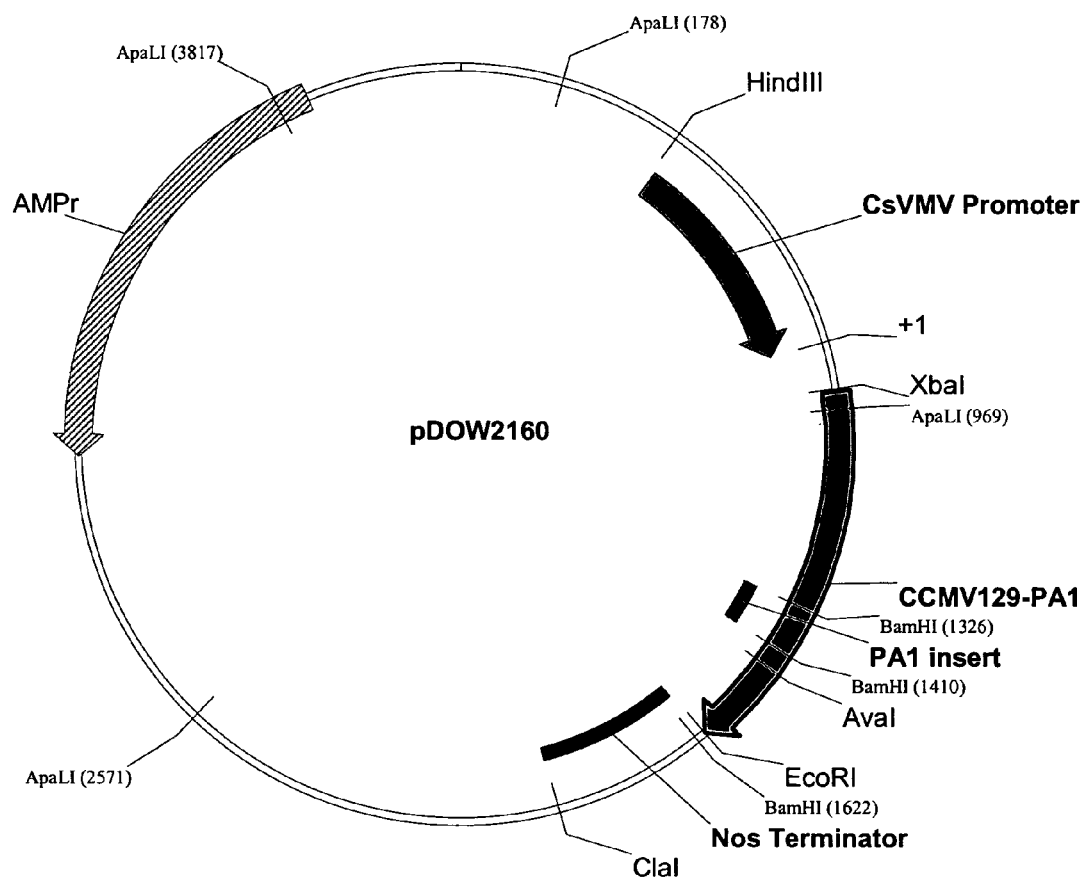
FIG. 5 shows plasmid map of pDOW2160.
Figure 6:
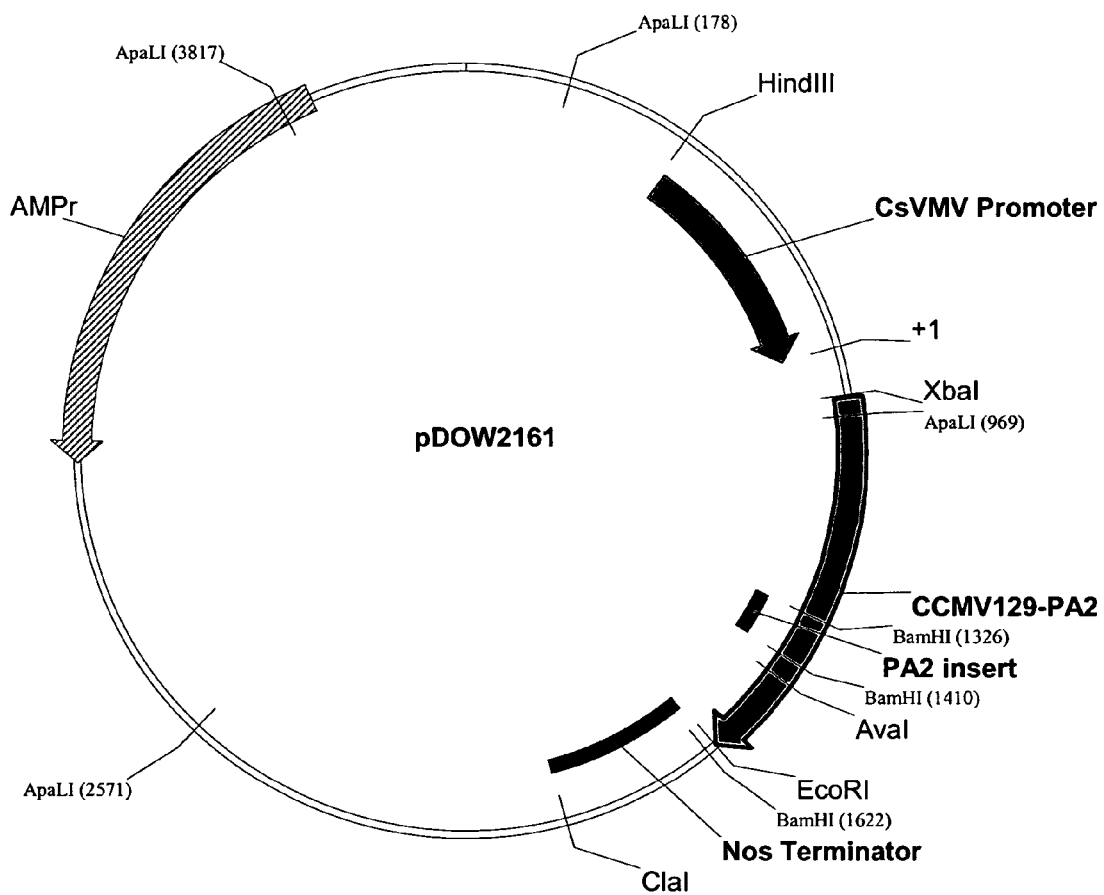
FIG. 6 shows plasmid map of pDOW2161.
Figure 7:
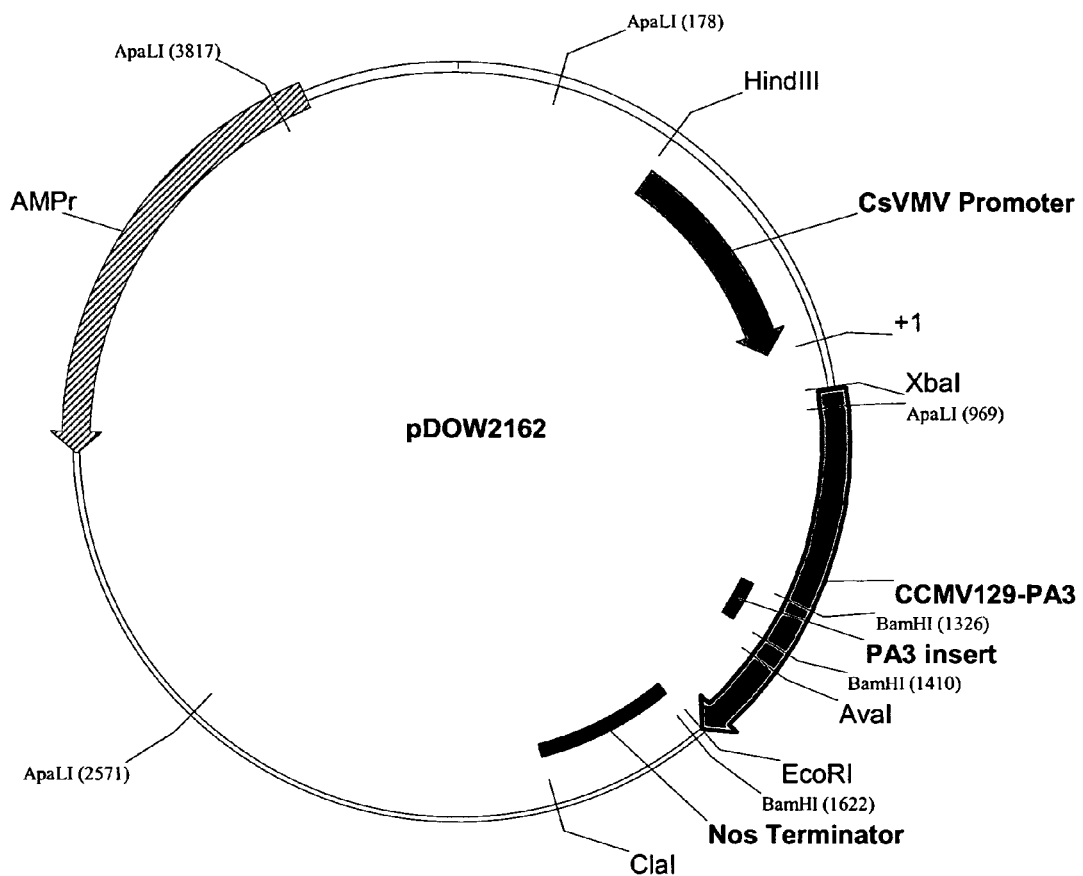
FIG. 7 shows plasmid map of pDOW2162.
Figure 8:
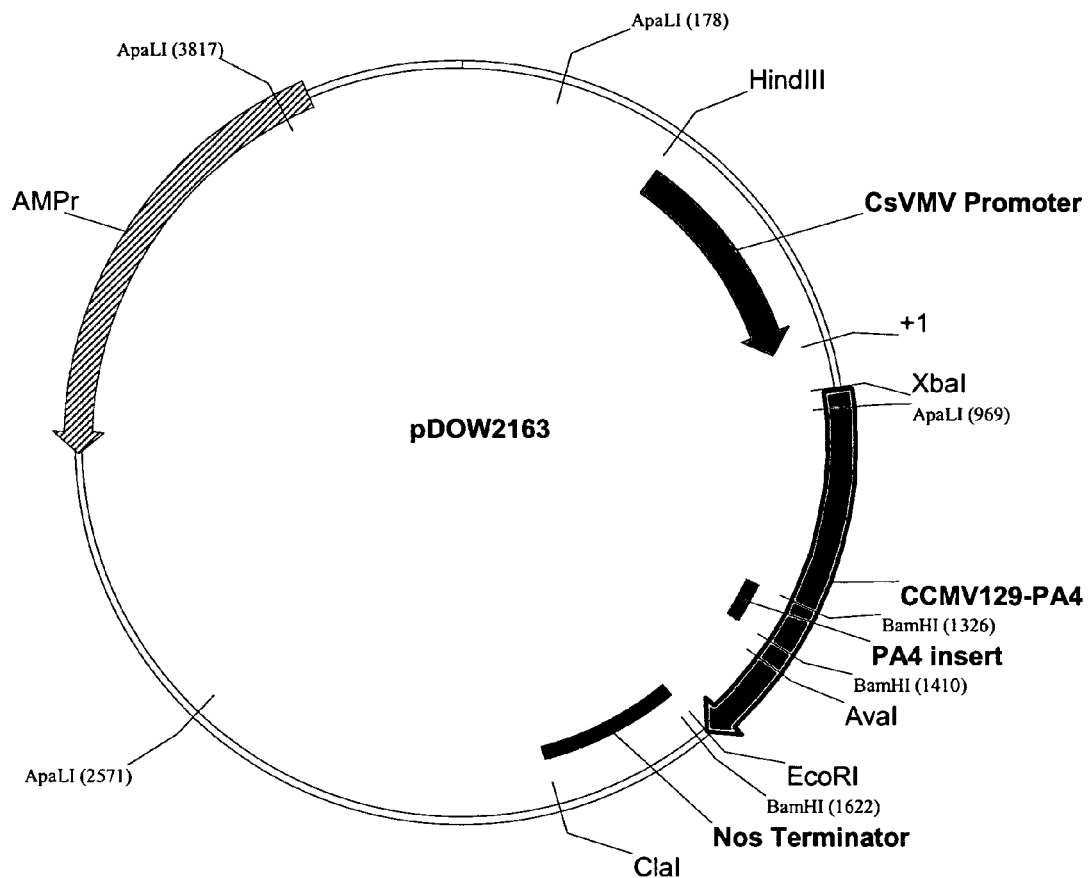
FIG. 8 shows plasmid map of pDOW2163.

All 4 PA peptides (PA1, PA2, PA3, and PA4) fused to CCMV coat protein at the 63, 102, 114, 129, and 160 BamHI site were successfully produced in tobacco cells. FIG. 3 and FIG. 4 show the expression of chimeric CCMV CP in cells transfected with CCMV RNA1, RNA2, and chimeric RNA3 containing CP with the four PA peptide inserts in the position 63, 102, 114, 129, and 160. FIG. 3 demonstrates that the fusion protein of CCMV CP with PA1, PA2, PA3, or PA4 peptide that has been inserted at the position 63, 102, or 114, is expressed in the tobacco plant cells with the exception of PA2 peptide that has been inserted into the CCMP CP at the position 63. FIG. 4 demonstrates that the fusion protein of CCMV CP with PA1, PA2, PA3, or PA4 peptide that has been inserted at the position 129 or 160, is expressed in the tobacco plant cells.

Example 3

Production of 4 Antigenic Peptides in CCMV Virus-Like Particles in Tobacco Suspension Culture Transfected with Plant Expression Plasmids Encoding the Chimeric CCMV CPs 1) Vector Construction:

Plasmid pIL-Tab358 was used as the plant expression vector. Restriction sites chosen for CCMV CP insertion were XbaI and EcoRI. This plasmid contains the Cassava Vein Mosaic Virus promoter upstream of the XbaI site and a Nos terminator downstream of the EcoRI site. The vector was prepared by digestion with XbaI and EcoRI and dephosphorylated before litigation with the inserts.

2) Insert Construction:

CCMV CP-PA fusions were amplified by PCR out of pDOW2147 (PUC-CCMV-RNA3-CP129BamHI-PA1), pDOW2148 (pUC-CCMV-RNA3-CP129BamHI-PA2), pDOW2149 (pUC-CCMV-RNA3-CP 129BamHI-PA3), pDOW2150 (pUC-CCMV-RNA3-CP 129BamHI-PA4) using primers CCMV-CP-XbaI (SEQ ID NO:22) and CCMV-CP-EcoRI (SEQ ID NO: 23) to create pDOW2160 (pIL-Tab-CCMV129BamHI-PA1) (SEQ ID NO: 5), pDOW2161 (pIL-Tab-CCMV129BamHI-PA2) (SEQ ID NO:6), pDOW2162 (pIL-Tab-CCMV129BamHI-PA3) (SEQ ID NO:7), and pDOW2163 (pIL-Tab-CCMV129BamHI-PA4) (SEQ ID NO:8). Plasmid maps for pDOW2160, pDOW 2161, pDOW2162, and pDOW 2163 are shown in FIGS. 5, 6, 7, and 8.

3) Plant Cell Transfection:

Plant cells were transfected with 10 μg of plasmid pDOW2160, pDOW2161, pDOW2162, and pDOW2163. Plant cell transfection was performed as in Example 2.

Results

Figure 9:
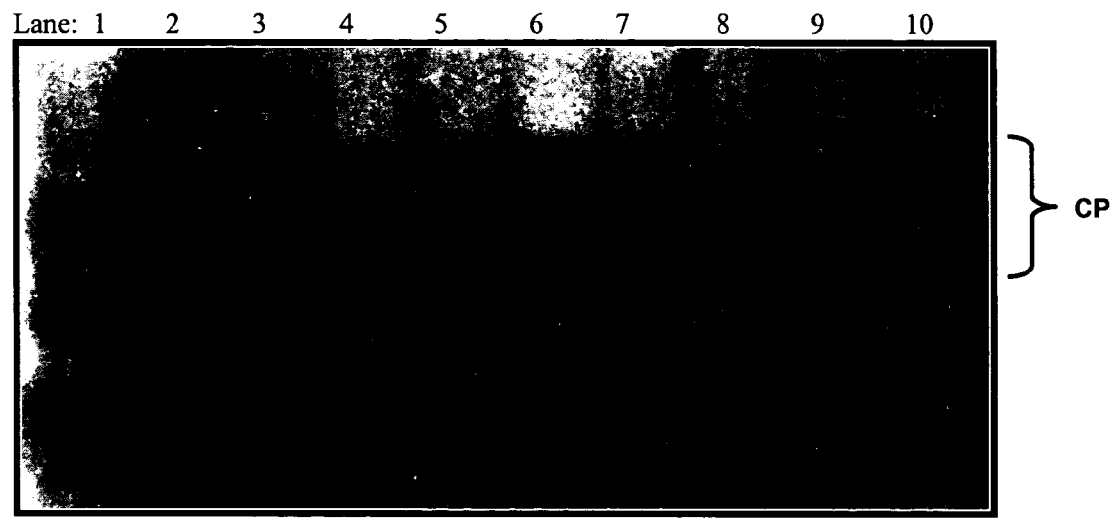
FIG. 9 shows expression of chimeric CCMV CP in tobacco NT1 cells transfected with non-infectious plasmids pDOW2160, pDOW2161, pDOW2162, and pDOW2163. The plant cell extracts were run on SDS-PAGE gel and probed with anti-CCMV polyclonal antibodies. Lane 1 represents Buffer only, Lane 2-6 represent RNA1+RNA2+wt RNA3 (control), Lane 7 represents pDOW2160, Lane 8 represents pDOW2161, Lane 9 represents pDOW2162, and Lane 10 represents pDOW2163.

All four PA peptides-CCMV CP fusions at 129BamHI site were successfully expressed in tobacco cells. FIG. 9 shows the expression of chimeric CCMV CP in cells transfected with pDOW2160, pDOW2161, pDOW2162, and pDOW2163. Compared to the control (CCMV coat protein with no insert), all four chimeric coat proteins showed slower mobility indicative of having PA inserts.

Example 4

Production of 4 Antigenic Peptides as CCMV CP Fusions in Virus-Like Particles in Tobacco Suspension Culture Transfected with Plant Expression Plasmids Encoding the Chimeric CCMV CPs and 3'UTR (CCMVRNA3 3' Untranslated Region)

1) Vector Construction.

Plasmid pIL-Tab358 was used as the plant expression vector. Restriction sites chosen for CCMV CP insertion were XbaI and EcoRI. This plasmid contains the Cassava Vein Mosaic Virus promoter upstream of the XbaI site and a Nos terminator downstream of the EcoRI site. The vector was prepared by digestion with XbaI and EcoRI and depshophorylated before litigation with the inserts.

2) Insert Construction:

CCMV CP-PA fusions containing the 3'UTR of RNA3 were amplified by PCR out of pDOW2147, pDOW2148, pDOW2149, and pDOW2150 using primers CCMV-CP-XbaI and CCMV-CP-EcoRI-3'UTR (SEQ ID NO: 24) to create pDOW2169 (pIL-Tab-CP129BamHI-PA1-3'UTR) (SEQ ID NO: 9), pDOW2170 (pIL-Tab-CP129BamHI-PA2-3'UTR) (SEQ ID NO: 10), pDOW2171 (pIL-Tab-CP129BamHI-PA3-3'UTR) (SEQ ID NO: 11), and pDOW2172 (pIL-Tab-CP 129BamHI-PA4-3'UTR) (SEQ ID NO: 12).

3) Plant Cell Transfection:

Plant cells were transfected with 10 μg of plasmid pDOW2169, pDOW2170, pDOW2171, and pDOW2172. Plant cell transfection was performed as in Example 2.

Results

Figure 10:
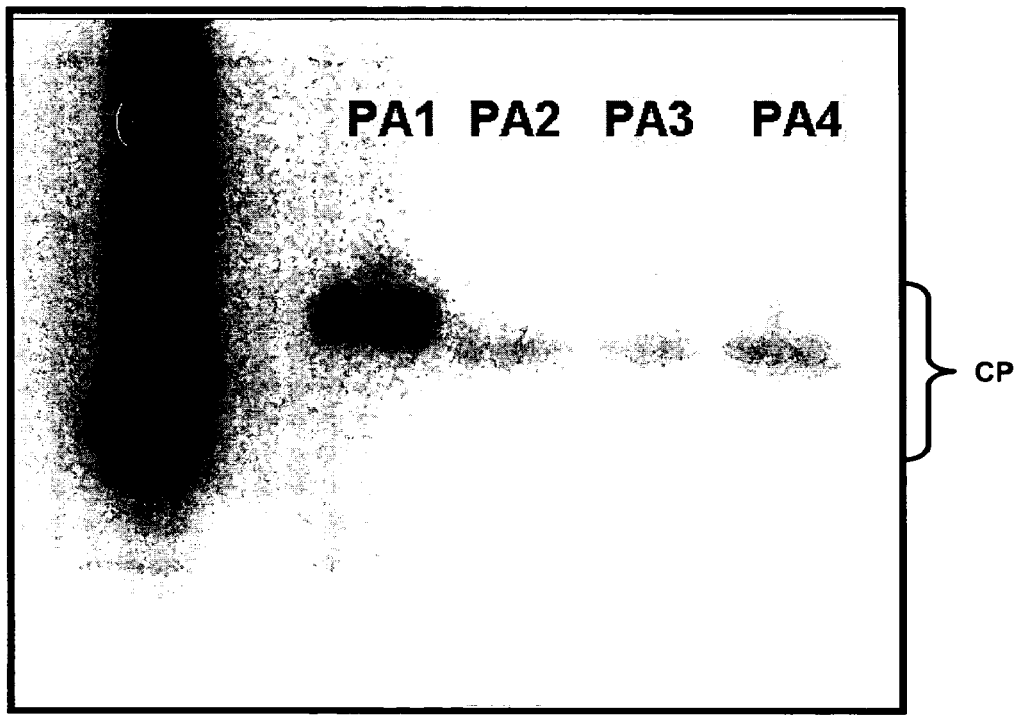
FIG. 10 shows expression of chimeric CCMV CP in tobacco NT1 cells transfected with non-infectious plasmids pDOW2169, pDOW2170, pDOW2171, and pDOW2172. The plant cell extracts were run on SDS-PAGE gel and probed with anti-CCMV polyclonal antibodies. Lane 1 represents RNA1+RNA2+RNA3 (control), Lane 2 represents Buffer, Lane 3 represents pDOW2169, Lane 4 represents pDOW2170, Lane 5 represents pDOW2171, and Lane 6 represents pDOW2172.

All four PA peptides-CCMV CP fusions at 129BamHI site containing the 3'UTR were successfully expressed in tobacco cells. FIG. 10 shows the expression of chimeric CCMV CP in cells transfected with pDOW2169, pDOW2170, pDOW2171, and pDOW2172. Compared to the control (CCMV coat protein with no insert), all four chimeric coat proteins showed slower mobility indicative of having PA inserts.

Example 5

Production of 4 Antigenic Peptides as CCMV CP Fusions in Virus-Like Particles in Transgenic Tobacco Suspension Cell Culture Transformed with Plant Expression Plasmids Encoding the Chimeric CCMV CPs Tobacco cell line NT1 was maintained by subculturing weekly. Cells were grown in NTI media at 24° C. or 28° C. with gentle shaking. Three days before transformation, 5 ml of cell suspension was subcultured into 50 ml of NTI media and incubated at 28° C.

1) Plant Cell Transformation by Particle Bombardment:

Plasmids pDOW2160, pDOW2161, pDOW2162, pDOW2163 and plant expression plasmid pBBV containing plant selectable marker Pat driven by the Cassava Vein Mosaic Virus promoter (pBBV) were used for NT1 tobacco cells transformation by micro-particle bombardment. The plasmid ratio used was 1:6 pBBV:pDOW2160, pBBV:pDOW2161, pBBV:pDOW2162, or pBBV:pDOW2163. Total of 5 ug of plasmid DNAs were sufficient for 6 bombardments. Biorad bombardment protocol as described in Chen, L et al. Plant Cell Reports (1998) 18: 25-31 was used for transformation.

2) Plating

Bombarded cells were transferred on non-selective NT1 media agar plates for 4 hours before transferring to NT1 media agar plate with 25 ug/ml of Glufosinate-ammonium (Sigma cat#45520).

3) Selecting Transgenic Calli.

After 21 days, calli that had white fluffy cell growth were selected for analysis by western blotting to test for the expression of CP fusions and PCR to test for integration of promoter-CP fusion gene-terminator cassette into the plant genome. Transgenic calli expressing chimeric CCMV CPs were transferred to liquid NT1 media. Cells were grown in NT1 media at 24° C. or 28° C. with gentle shaking and subcultured weekly.

Results

Figure 11:
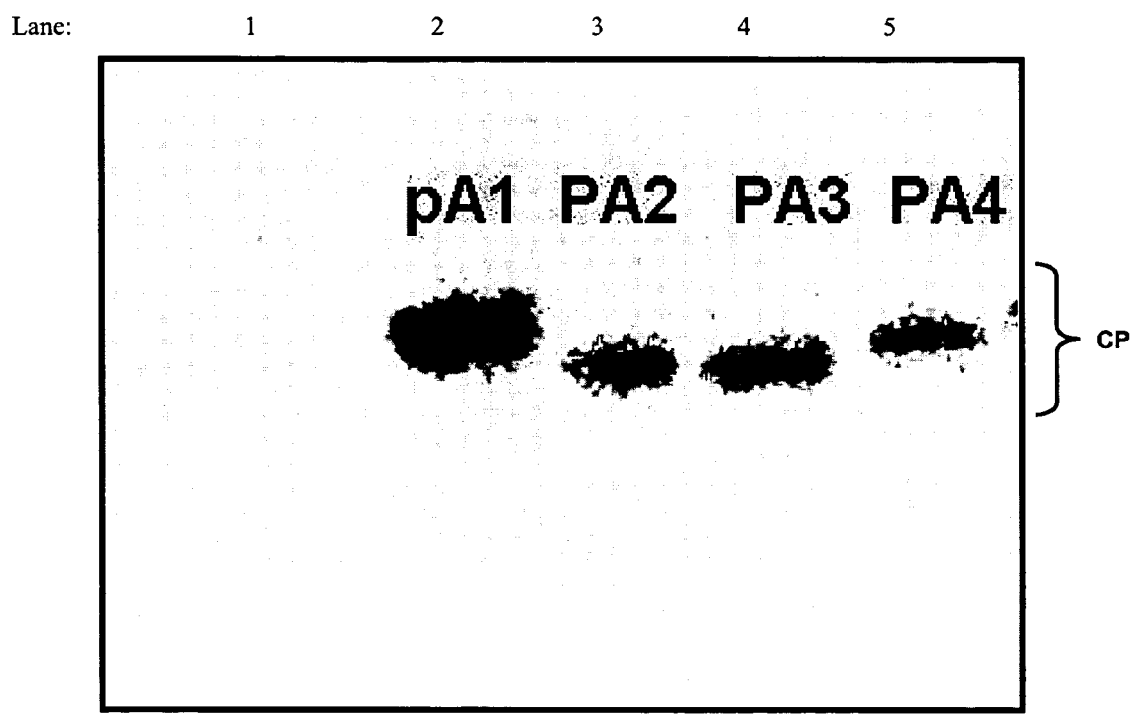
FIG. 11 shows expression of chimeric CCMV CP in tobacco NT1 cells stably transformed with non-infectious plasmids pDOW2160, pDOW2161, pDOW2162, and pDOW2163. After selection for 21 days, calli that had white fluffy cell growth were selected for analysis by western blotting for to test for CP expression. The plant cell extracts were run on SDS-PAGE gel and probed with anti-CCMV polyclonal antibodies. Lane 1 represents Untransformed tobacco cells (negative control), Lane 2 represents Transgenic tobacco cells transformed with pDOW2160, Lane 3 represents Transgenic tobacco cells transformed with pDOW2161, Lane 4 represents Transgenic tobacco cells transformed with pDOW2162, and Lane 5 represents Transgenic tobacco cells transformed with pDOW2163.

FIG. 11 shows the expression of chimeric CCMV CP in cells stably transformed with pDOW2160, pDOW2161, pDOW2162, and pDOW2163. The CP fusion was detected by polyclonal antibodies for CCMV. Expression of all four chimeric coat protein transgenes was detected.

Example 6

Production of 4 Antigenic Peptides as CCMV CP Fusions in CCMV Virus-Like Particles in Transgenic Rice Suspension Culture Transformed with Plant Expression Plasmids Encoding the Chimeric CCMV CPs Rice cell lines were maintained by sub-culturing weekly. Cells were grown in NB media (Li, L et al. Plant Cell Reports. (1993) 12: 250-255) at 28° C. with gentle shaking. Three days before transformation, 5 ml of cell suspension was sub-cultured into 50 ml of NB media and incubated at 28° C.

1) Plant Cell Transformation by Particle Bombardment.

Plasmids pDOW2160, pDOW2161, pDOW2162, and pDOW2163 and plant expression plasmid pBBV containing plant selectable marker Pat driven by the Cassava Vein Mosaic Virus promoter were used for rice cells transformation by microparticle bombardment. The plasmid ratio used was 1:6 pBBV:pDOW2160, pBBV:pDOW2161, pBBV:pDOW2162, or pBBV:pDOW2163. Total of 5 ug of plasmid DNAs were sufficient for 6 bombardments. Biorad bombardment protocol as described in Chen, L et al. Plant Cell Reports (1998) 18: 25-31 was used for transformation.

2) Plating.

Bombarded cells were transferred to NB media agar plates with 25 ug/ml of Glufosinate-ammonium (Sigma cat#45520) for selection.

3) Selecting Transgenic Calli.

After 21 days, calli that had white fluffy cell growth were selected for analysis by western blotting to test for the expression of CP fusions and PCR to test for integration of promoter-CP fusion gene-terminator cassette into the plant genome.

Results

Figure 12:
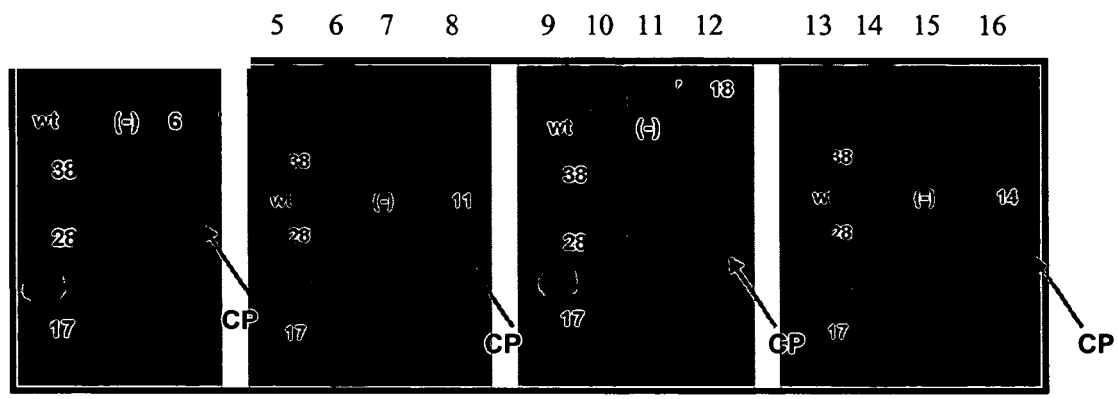
FIG. 12 shows expression of chimeric CCMV CP in rice cells stably transformed with non-infectious plasmids pDOW2160, pDOW2161, pDOW2162, and pDOW2163. After selection for 21 days, calli that had white fluffy cell growth were selected for analysis by western blotting for to test for CP expression. The plant cell extracts were run on SDS-PAGE gel and probed with anti-CCMV polyclonal antibodies. Lane 1 represents wt CCMV CP (positive control), Lane 2 represents Size ladder, Lane 3 represents Non-transgenic rice cells (negative control), Lane 4 represents Transgenic rice cells transformed with pDOW2160, Lane 5 represents wt CCMV CP (positive control), Lane 6 represents Size ladder, Lane 7 represents Non-transgenic rice cells, Lane 8 represents Transgenic rice cells transformed with pDOW2161, Lane 9 represents wt CCMV CP (positive control), Lane 10 represents Size ladder, Lane 11 represents Non-transgenic rice cells (negative control), Lane 12 represents Transgenic rice cells transformed with pDOW2162, Lane 13 represents wt CCMV CP (positive control), Lane 14 represents Size ladder, Lane 15 represents Non-transgenic rice cells (negative control), and Lane 16 represents Transgenic rice cells transformed with pDOW2163.

FIG. 12 shows the expression of chimeric CCMV CP in cells stably transformed with pDOW2160, pDOW2161, pDOW2162, and pDOW2163 as detected by polyclonal antibodies to CCMV. Expression of all four chimeric coat protein transgenes was detected.

The following protocol has been used to extract genomic DNA and test for integration of promoter-CP fusion gene-terminator cassette into the plant genome by PCR. Qiagen DNEASY PLANT MINI™ DNA isolation kit was used to extract genomic DNA following the manufacturer directions.

Approximately 50-100 mg of fresh rice callus was placed into a 1.5 ml tube. The tissue was frozen in liquid $N_2$ for immediate DNA extraction or placed in –80° C. freezer for storage. Prior to DNA extraction the tissue was manually disrupted by grinding with a micropestle. The sample was placed on ice and the genomic DNA was extracted as described in Qiagen DNEASY PLANT MINI™ DNA isolation manual. The ACCESS QUICK MASTER MIX 2X™ PCR buffer (Promega cat#A1720) was used to set up the PCR reaction as follows:

| Master mix | 25 ul |
| CCMV-F (10 mM) primer, SEQ ID NO: 25 | 1 ul |
| Nos-term-R (10 mM) primer, SEQ ID NO: 26 | 1 ul |
| Genomic DNA | 1 ul |
| water | 22 ul |
| Total | 50 ul |

The following PCR cycle has been used to amplify the promoter-CP fusion gene-terminator cassette from the genomic DNA:

| 1 cycle | 95° C. | 2 min |
| 35 cycles of | 95° C. | 30 sec |
| | 55° C. | 30 sec |
| | 70° C. | 2 min |
| 1 cycle | 70° C. | 5 min |
| | 4° C. | hold |

Figure 13:
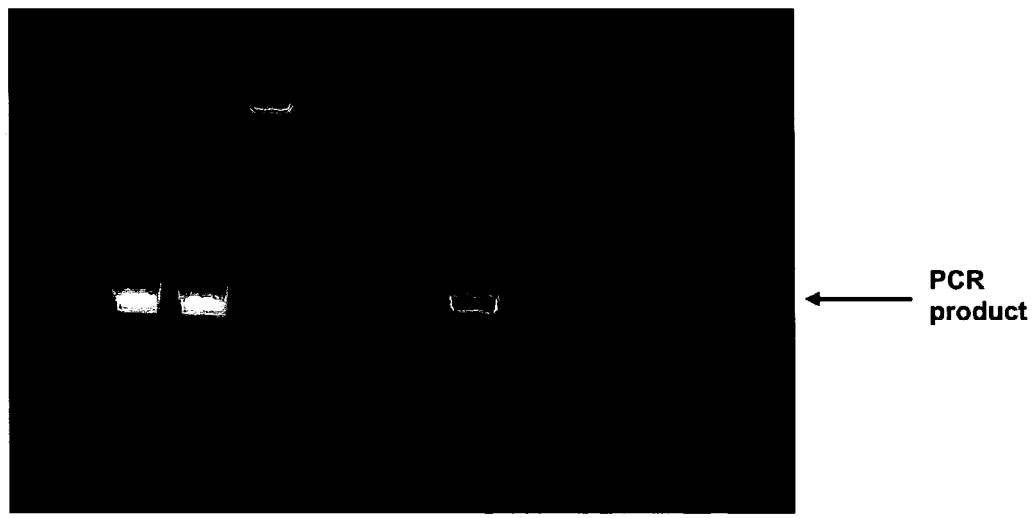
FIG. 13 shows detection of PCR products amplified from selected individual rice calli transformed with non-infectious plasmids pDOW2160, pDOW2161, pDOW2162, and pDOW2163. 1.2% agarose gel stained with EtBr showing PCR products amplified from selected individual rice calli. After selection for 21 days, calli that had white fluffy cell growth were selected for analysis by PCR to test for integration of promoter-CP fusion gene-terminator cassette into the plant genome. Lane 1 represents Rice calli 46-5, Lane 2 represents Rice calli 46-11, Lane 3 represents Rice calli 46-17, Lane 4 represents Size Ladder, Lane 5 represents Rice calli 47-6, Lane 6 represents Rice calli 48-12, Lane 7 represents Rice calli 48-18, Lane 8 represents Rice calli 48-20, Lane 9 represents Rice calli 49-11, Lane 10 represents Rice calli 49-18, and Lane 11 represents Negative control (non-transgenic rice cells).

10 ul of PCR reaction was run on 1.2% agarose gel stained with EtBr. FIG. 13 shows a PCR products amplified from selected individual rice calli. The samples that contained a PCR product of predicted size were scored as positive for stable transformation and integration of the chimeric CP transgene into the plant genome.

Transgenic calli expressing chimeric CCMV CPs were transferred to liquid NB media to create a cell suspension culture suitable for scale up fermentation. Cells were grown in NB media at 28° C. with gentle shaking and subcultured weekly.

VLP Extraction:

Chimeric VLPs were precipitated by lysis of shake-flask culture samples, followed by PEG (polyethylene glycol)-treatment of the resulting cell lysates and ultrafiltration, according to the following protocol:

50 mL aliquots of each shake-flask culture were centrifuged to pellet the cells. Pelleted cells were resuspended in virus buffer (0.2M Sodium Acetate pH 5.2; 10 mM EDTA.0) at a 2 volume buffer to 1 volume pellet ratio. Cells were then disrupted by blending for 60 sec multiple times, with 2 minutes resting on ice in between. The resulting homogenate was squeezed through 3 layers of cheese cloth and was then centrifuged for 15 min at 15,000×G at 4° C. The resulting supernatants were removed and their volumes measured. To each supernatant, PEG8000 was added to a final concentration of 10% and the solution was incubated on ice for 1 hr or overnight at 4° C. Then, the solution was centrifuged at 15,000×G for 10 min at 4° C. Precipitated pellets were then resuspended in ¹⁄₁₀ initial supernatant volume of virus buffer and stored at 4° C. and analyzed by western blotting with polyclonal anti-CCMV antibodies.

Figure 14:
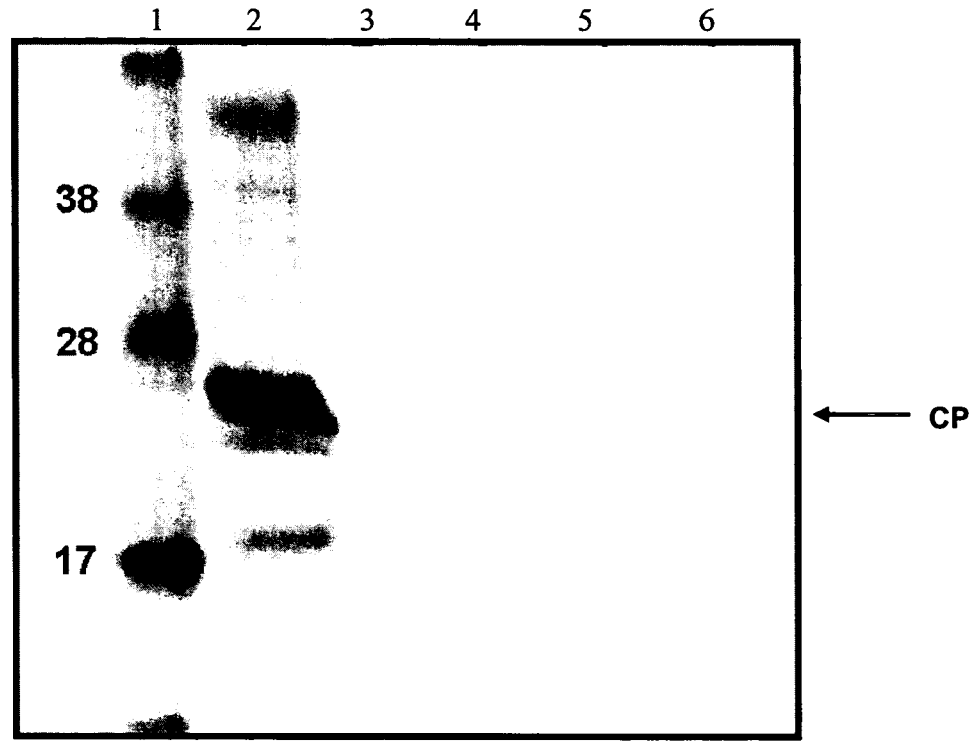
FIG. 14 shows western blot analysis of chimeric CCMV VLPs purified from rice cells stably transformed with non-infectious plasmid pDOW2160 by PEG precipitation and ultra-filtration and detection of chimeric CP-PA1 fusion proteins in the purified VLP samples. The samples were run on SDS-PAGE gel and probed with anti-CCMV polyclonal antibodies. Lane 1 represents Size ladder, Lane 2 represents Total cell lysate from rice suspension cells transgenic for CCMV CP-PA1 fusion, Lane 3 represents First PEG supernatant, Lane 4 represents First PEG pellet, Lane 5 represents Second PEG pellet, and Lane 6 represents Second PEG supernatant.
Figure 15:
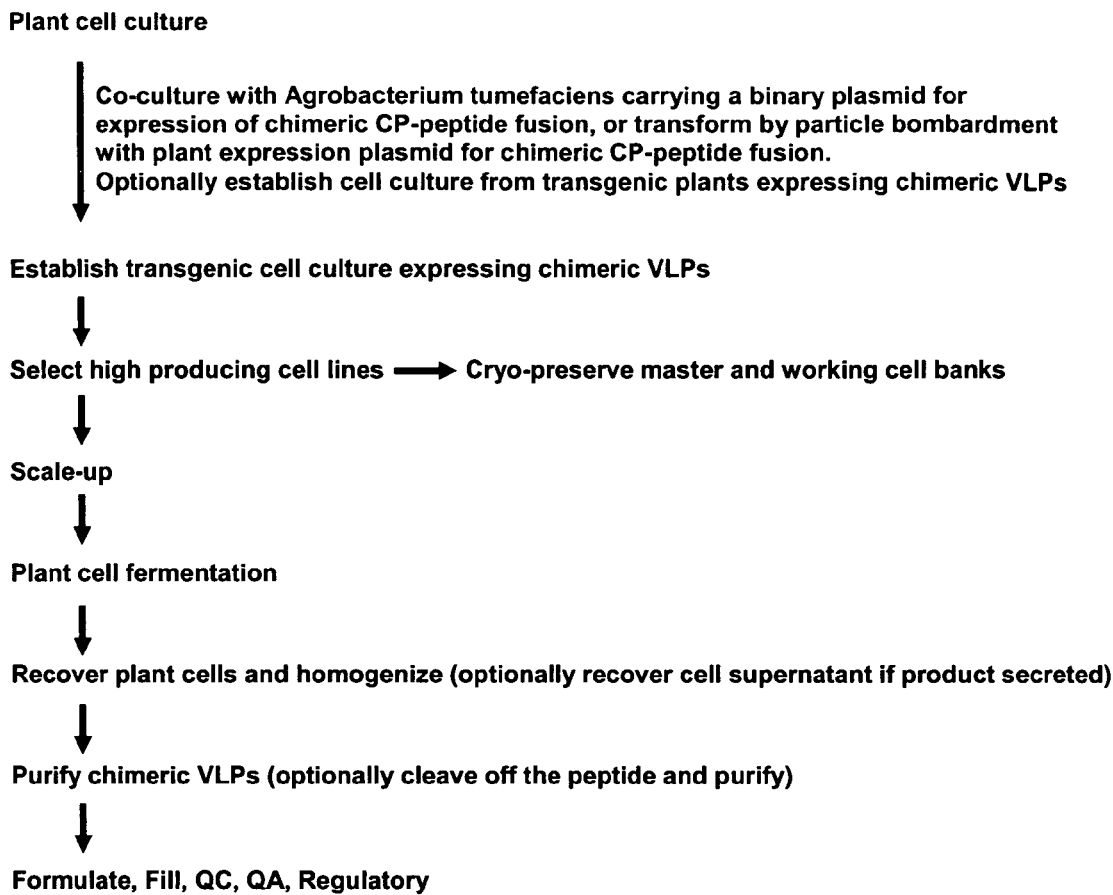
FIG. 15 shows diagram of production process of chimeric VLPs in plant suspension cells by fermentation.

FIG. 14 shows that the chimeric CCMV VLPs were recovered from cells stably transformed with pDOW2160. Chimeric CP-PA1 fusion proteins were detected in the resuspended PEC pellets but not the supernatant indicating the chimeric CP assembled into VLPs.

Alternatively, the resuspended samples were centrifuged for 10 min at 15,000×G at 4° C., the supernatant was recovered and subjected to the second round of PEG precipitation. PEG8000 was added to final concentration of 15% and stirred at 4° C. for 2 hours. The solution was then centrifuged at 15,000×G for 10 mins and the pellet was resuspended in small volume of virus buffer. T The resuspended VLP solution was loaded on to a centrifugal filter unit (CENTRICON PLUS 20™) with 300K molecular weight cut-off and spun at 4,000×G for 5 mins. The concentrated VLP sample was then analyzed by western blotting with polyclonal anti-CCMV antibodies (see FIG. 14). Chimeric CP-PA1 fusion proteins were detected in the resuspended and size-filtered second PEG pellets, but not in the supernatant, indicating the chimeric CP assembled into VLPs.

We claim:

1. An isolated plant cell comprising a non-infectious nucleic acid comprising a nucleic acid sequence encoding a fusion peptide, wherein the fusion peptide is comprised of at least one heterologous peptide of interest and at least one viral capsid protein, wherein the heterologous peptide is inserted into at least one surface loop of the viral capsid protein, and wherein the nucleic acid is integrated into the genome of the plant cell.

2. The plant cell of claim 1, wherein the fusion peptide, when expressed in the plant cell, assembles in vivo into a virus like particle.

3. The plant cell of claim 1, wherein the antigenic peptide is selected from the group consisting of Seq. ID. Nos. 1-4.

4. The plant cell of claim 1, wherein the nucleic acid sequence is Seq. ID. No. 5.

5. The plant cell of claim 1, wherein the plant cell is *Nicotiana tabacum*.

6. The plant cell of claim 1, wherein the plant cell is *Oryza sativa*.

7. The plant cell of claim 1, wherein the nucleic acid further comprises a 3' untranslated region derived from the 3' untranslated region of the genomic nucleic acid sequence encoding the viral capsid protein.

8. The plant cell of claim 7, wherein the 3' untranslated region further comprises an encapsidation signal.

9. The plant cell of claim 1, wherein the viral capsid protein is derived from a virus that displays native trophism for the plant cell host.

10. The plant cell of claim 1, wherein the viral capsid protein is derived from an icosahedral plant virus.

11. The plant cell of claim 10, wherein the icosahedral virus is selected from the group of viruses consisting of Cowpea Mosaic Virus, Cowpea Chlorotic Mottle Virus, and Alfalfa Mosaic Virus.

12. The plant cell of claim 1, wherein the viral capsid protein is derived from a plant virus that is non-trophic to the plant cell.

13. The plant cell of claim 12, wherein the viral capsid protein is derived from an icosahedral plant virus.

14. The plant cell of claim 13, wherein the icosahedral virus is selected from the group of viruses consisting of Cowpea Mosaic Virus, Cowpea Chlorotic Mottle Virus, and Alfalfa Mosaic Virus.

15. The plant cell of claim 1, wherein the plant cell is a cultured cell in a suspension plant cell culture.

16. A process for producing a heterologous peptide comprising:

a) providing the isolated plant cell of claim 1;
b) expressing the fusion peptide in the plant cell, wherein the plant cells are grown in a suspension plant cell culture in a fermentation process;
c) wherein the expression in the plant cell provides for in vivo assembly of the fusion peptide into a virus like particle; and
d) isolating the virus like particle.

17. The process of claim 16, wherein the nucleic acid encoding the fusion peptide is operably linked to a promoter sequence and a terminator sequence.

18. The process of claim 17, wherein the nucleic acid further comprises a viral 3'UTR.

19. The process of claim 18, wherein the 3'UTR comprises an encapsidation signal.

20. The process of claim 17, wherein the nucleic acid further comprises an encapsidation signal.

21. The process of claim 16, wherein the viral capsid protein is derived from a virus that does not display native trophism for the plant cell host.

22. The process of claim 16, wherein the viral capsid protein is derived from a virus that displays native trophism for the plant cell host.

23. The process of claim 16, wherein the viral capsid protein is derived from an icosahedral plant virus.

24. The process of claim 23, wherein the icosahedral virus is selected from the group of viruses consisting of Cowpea Mosaic Virus, Cowpea Chlorotic Mottle Virus, and Alfalfa Mosaic Virus.

25. The process of claim 16, wherein the heterologous peptide is an antigenic peptide.

26. The process of claim 25, wherein the antigenic peptide is a *Bacillus anthracis* peptide.

27. The process of claim 26, wherein the antigenic peptide is selected from the group consisting of Seq. ID. Nos. 1-4.

28. The process of claim 16, wherein the nucleic acid is selected from the group consisting of Seq. ID. Nos. 5-12.

29. The process of claim 16, additionally comprising administering the virus like particle-to an animal as a vaccine.

30. The process of claim 16, wherein the plant cell is a dicot.

31. The process of claim 30, wherein the plant cell is *Nicotiana tabacum*.

32. The process of claim 16, wherein the plant cell is a monocot.

33. The process of claim 32, wherein the plant cell is *Oryza sativa*.

34. The process of claim 16, wherein the nucleic acid does not contain viral sequences encoding viral proteins other than the capsid protein.

* * * * *

SEQUENCE LISTING

<160> NUMBER OF SEQ ID NOS: 28

<210> SEQ ID NO 1
<211> LENGTH: 25
<212> TYPE: PRT
<213> ORGANISM: Bacillus anthracis

<400> SEQUENCE: 1

Ser Asn Ser Arg Lys Lys Arg Ser Thr Ser Ala Gly Pro Thr Val Pro
1               5                   10                  15

Asp Arg Asp Asn Asp Gly Ile Pro Asp
            20                  25

<210> SEQ ID NO 2
<211> LENGTH: 25
<212> TYPE: PRT
<213> ORGANISM: Bacillus anthracis

<400> SEQUENCE: 2

Ser Pro Glu Ala Arg His Pro Leu Val Ala Ala Tyr Pro Ile Val His
1               5                   10                  15

Val Asp Met Glu Asn Ile Ile Leu Ser
            20                  25

<210> SEQ ID NO 3
<211> LENGTH: 25
<212> TYPE: PRT
<213> ORGANISM: Bacillus anthracis

<400> SEQUENCE: 3

Arg Ile Ile Phe Asn Gly Lys Asp Leu Asn Leu Val Glu Arg Arg Ile
1               5                   10                  15

Ala Ala Val Asn Pro Ser Asp Pro Leu
            20                  25

<210> SEQ ID NO 4
<211> LENGTH: 25
<212> TYPE: PRT
<213> ORGANISM: Bacillus anthracis

<400> SEQUENCE: 4

Arg Gln Asp Gly Lys Thr Phe Ile Asp Phe Lys Lys Tyr Asn Asp Lys
1               5                   10                  15

Leu Pro Leu Tyr Ile Ser Asn Pro Asn
            20                  25

<210> SEQ ID NO 5
<211> LENGTH: 4136
<212> TYPE: DNA
<213> ORGANISM: artificial
<220> FEATURE:
<223> OTHER INFORMATION: pDOW2160

<400> SEQUENCE: 5
tcgcgcgttt cggtgatgac ggtgaaaacc tctgacacat gcagctcccg gagacggtca      60
cagcttgtct gtaagcggat gccgggagca gacaagcccg tcagggcgcg tcagcgggtg     120
ttggcgggtg tcggggctgg cttaactatg cggcatcaga gcagattgta ctgagagtgc     180

```
accatatgcg gtgtgaaata ccgcacagat gcgtaaggag aaaataccgc atcaggcgcc    240
attcgccatt caggctgcgc aactgttggg aagggcgatc ggtgcgggcc tcttcgctat    300
tacgccagct ggcgaaaggg ggatgtgctg caaggcgatt aagttgggta acgccagggt    360
tttcccagtc acgacgttgt aaaacgacgg ccagtgccaa gcttccagaa ggtaattatc    420
caagatgtag catcaagaat ccaatgttta cgggaaaaac tatggaagta ttatgtgagc    480
tcagcaagaa gcagatcaat atgcggcaca tatgcaacct atgttcaaaa atgaagaatg    540
tacagataca agatcctata ctgccagaat acgaagaaga atacgtagaa attgaaaaag    600
aagaaccagg cgaagaaaag aatcttgaag acgtaagcac tgacgacaac aatgaaaaga    660
agaagataag gtcggtgatt gtgaaagaga catagaggac acatgtaagg tggaaaatgt    720
aagggcggaa agtaacctta tcacaaagga atcttatccc ccactactta tcctttata     780 tttttccgtg tcattttgc ccttgagttt tcctatataa ggaaccaagt tcggcatttg     840
tgaaaacaag aaaaaatttg gtgtaagcta ttttctttga agtactgagg atacaacttc    900
agagaaattt gtaagtttgt agatctcgat tctagaatgt ctacagtcgg aacagggaag    960
ttaactcgtg cacaacgaag ggctgcggcc cgtaagaaca agcggaacac tcgtgtggtc   1020
caacctgtta ttgtagaacc catcgcttca ggccaaggca aggctattaa agcatggacc   1080
ggttacagcg tatcgaagtg gaccgcctct tgtgcggctg ccgaagctaa agtaacctcg   1140
gctataacta tctctctccc taatgagcta tcgtccgaaa ggaacaagca gctcaaggta   1200
ggtagagttt tattatggct tgggttgctt cccagtgtta gtggcacagt gaaatcctgt   1260
gttacagaga cgcagactac tgctgctgcc tcctttcagg tggcattagc tgtggccgac   1320
aacgggatcc ttagtaattc tcgtaagaaa cgttctacct ctgctggccc taccgtgcct   1380
gatcgtgata atgatggcat tcctgatggg atcctgtcga agatgttgt cgctgctatg    1440 taccccgagg cgtttaaggg tataacccctt gaacaactca ccgcggattt aacgatctac   1500
ttgtacagca gtgcggctct cactgagggc gacgtcatcg tgcatttgga ggttgagcat   1560
gtcagaccta cgtttgacga ctctttcact ccgtattagt aagaattcga gctcggtacc   1620
ggatccaatt cccgatcgtt caaacatttg gcaataaagt ttcttaagat tgaatcctgt   1680
tgccggtctt gcgatgatta tcatataatt tctgttgaat tacgttaagc atgtaataat   1740
taacatgtaa tgcatgacgt tatttatgag atgggttttt atgattagag tcccgcaatt   1800
atacatttaa tacgcgatag aaaacaaaat atagcgcgca aactaggata aattatcgcg   1860
cgcggtgtca tctatgttac tagatcgggg atcgatcccc aattcgtaat catggtcata   1920
gctgtttcct gtgtgaaatt gttatccgct cacaattcca cacaacatac gagccggaag   1980
cataaagtgt aaagcctggg gtgcctaatg cgtgagctaa ctcacattaa ttgcgttgcg   2040
ctcactgccc gctttccagt cgggaaacct gtcgtgccag ctgcattaat gaatcggcca   2100
acgcgcgggg agaggcggtt tgcgtattgg gcgctcttcc gcttcctcgc tcactgactc   2160
gctgcgctcg tcgttcggc tgcggcgagc ggtatcagct cactcaaagg cggtaatacg   2220
gttatccaca gaatcagggg ataacgcagg aaagaacatg tgagcaaaag gccagcaaaa   2280
ggccaggaac cgtaaaaagg ccgcgttgct ggcgtttttc cataggctcc gcccccctga   2340
cgagcatcac aaaaatcgac gctcaagtca gaggtggcga aacccgacag gactataaag   2400
ataccaggcg tttccccctg gaagctccct cgtgcgctct cctgttccga cctgccgct    2460 taccggatac ctgtccgcct ttctcccttc gggaagcgtg cgctttctc aatgctcacg    2520 ctgtaggtat ctcagttcgg tgtaggtcgt tcgctccaag ctgggtgtg tgcacgaacc    2580
```

```
cccgttcag cccgaccgct gcgccttatc cggtaactat cgtcttgagt ccaacccggt    2640
aagacacgac ttatcgccac tggcagcagc cactggtaac aggattagca gagcgaggta    2700
tgtaggcggt gctacagagt tcttgaagtg gtggcctaac tacggctaca ctagaaggac    2760
agtatttggt atctgcgctc tgctgaagcc agttaccttc ggaaaaagag ttggtagctc    2820
ttgatccggc aaacaaacca ccgctggtag cggtggtttt tttgtttgca agcagcagat    2880
tacgcgcaga aaaaaggat ctcaagaaga tcctttgatc ttttctacgg ggtctgacgc    2940
tcagtggaac gaaaactcac gttaagggat tttggtcatg agattatcaa aaaggatctt    3000
cacctagatc cttttaaatt aaaaatgaag ttttaaatca atctaaagta tatatgagta    3060
aacttggtct gacagttacc aatgcttaat cagtgaggca cctatctcag cgatctgtct    3120
atttcgttca tccatagttg cctgactccc cgtcgtgtag ataactacga tacgggaggg    3180
cttaccatct ggccccagtg ctgcaatgat accgcgagac ccacgctcac cggctccaga    3240
tttatcagca ataaaccagc cagccggaag ggccgagcgc agaagtggtc ctgcaacttt    3300
atccgcctcc atccagtcta ttaattgttg ccgggaagct agagtaagta gttcgccagt    3360
taatagtttg cgcaacgttg ttgccattgc tacaggcatc gtggtgtcac gctcgtcgtt    3420
tggtatggct tcattcagct ccggttccca acgatcaagg cgagttacat gatccccat    3480 gttgtgcaaa aaagcggtta gctccttcgg tcctccgatc gttgtcagaa gtaagttggc    3540
cgcagtgtta tcactcatgg ttatggcagc actgcataat tctcttactg tcatgccatc    3600
cgtaagatgc ttttctgtga ctggtgagta ctcaaccaag tcattctgag aatagtgtat    3660
gcggcgaccg agttgctctt gcccggcgtc aatacgggat aataccgcgc cacatagcag    3720
aactttaaaa gtgctcatca ttggaaaacg ttcttcgggg cgaaaactct caaggatctt    3780
aggcgtgttg agatccagtt cgatgtaacc cactcgtgca cccaactgat cttcagcatc    3840
ttttactttc accagcgttt ctgggtgagc aaaaacagga aggcaaaatg ccgcaaaaaa    3900
gggaataagg gcgacacgga aatgttgaat actcatactc ttcctttttc aatattattg    3960
aagcatttat cagggttatt gtctcatgag cggatacata tttgaatgta tttagaaaaa    4020
taaacaaata ggggttccgc gcacatttcc ccgaaaagtg ccacctgacg tctaagaaac    4080
cattattatc atgacattaa cctataaaaa taggcgtatc acgaggccct ttcgtc         4136
```

<210> SEQ ID NO 6
<211> LENGTH: 4136
<212> TYPE: DNA
<213> ORGANISM: artificial
<220> FEATURE:
<223> OTHER INFORMATION: pDOW2161

<400> SEQUENCE: 6

```
tcgcgcgttt cggtgatgac ggtgaaaacc tctgacacat gcagctcccg gagacggtca      60
cagcttgtct gtaagcggat gccgggagca gacaagcccg tcagggcgcg tcagcgggtg     120
ttggcgggtg tcggggctgg cttaactatg cggcatcaga gcagattgta ctgagagtgc     180
accatatgcg gtgtgaaata ccgcacagat gcgtaaggag aaaataccgc atcaggcgcc     240
attcgccatt caggctgcgc aactgttggg aagggcgatc ggtgcgggcc tcttcgctat     300
tacgccagct ggcgaaaggg ggatgtgctg caaggcgatt aagttgggta acgccagggt     360
tttcccagtc acgacgttgt aaaacgacgg ccagtgccaa gcttccagaa ggtaattatc     420
caagatgtag catcaagaat ccaatgttta cgggaaaaac tatggaagta ttatgtgagc     480
tcagcaagaa gcagatcaat atgcggcaca tatgcaacct atgttcaaaa atgaagaatg     540
```

```
tacagataca agatcctata ctgccagaat acgaagaaga atacgtagaa attgaaaaag    600
aagaaccagg cgaagaaaag aatcttgaag acgtaagcac tgacgacaac aatgaaaaga    660
agaagataag gtcggtgatt gtgaaagaga catagaggac acatgtaagg tggaaaatgt    720
aagggcggaa agtaacctta tcacaaagga atcttatccc ccactactta ccttttata    780 tttttccgtg tcattttttgc ccttgagttt tcctatataa ggaaccaagt tcggcatttg    840
tgaaaacaag aaaaaatttg gtgtaagcta ttttctttga agtactgagg atacaacttc    900
agagaaattt gtaagtttgt agatctcgat tctagaatgt ctacagtcgg aacagggaag    960
ttaactcgtg cacaacgaag ggctgcggcc cgtaagaaca agcggaacac tcgtgtggtc   1020
caacctgtta ttgtagaacc catcgcttca ggccaaggca aggctattaa agcatggacc   1080
ggttacagcg tatcgaagtg gaccgcctct tgtgcggctg ccgaagctaa ggtaacctcg   1140
gctataacta tctctctccc taatgagcta tcgtccgaaa ggaacaagca gctcaaggta   1200
ggtagagttt tattatggct tgggttgctt cccagtgtta gtggcacagt gaaatcctgt   1260
gttacagaga cgcagactac tgctgctgcc tcctttcagg tggcattagc tgtggccgac   1320
aacgggatcc ttagtcctga agctcgtcat cctctcgtgg ctgcgtatcc tattgtgcat   1380
gttgatatgg aaaatattat cctctctggg atcctgtcga agatgttgt cgctgctatg   1440 tacccccgagg cgtttaaggg tataacccctt gaacaactca ccgcggattt aacgatctac   1500
ttgtacagca gtgcggctct cactgagggc gacgtcatcg tgcatttgga ggttgagcat   1560
gtcagaccta cgtttgacga ctctttcact ccgtattagt aagaattcga gctcggtacc   1620
ggatccaatt cccgatcgtt caaacatttg gcaataaagt ttcttaagat tgaatcctgt   1680
tgccggtctt gcgatgatta tcatataatt tctgttgaat tacgttaagc atgtaataat   1740
taacatgtaa tgcatgacgt tatttatgag atgggttttt atgattagag tcccgcaatt   1800
atacatttaa tacgcgatag aaaacaaaat atagcgcgca aactaggata aattatcgcg   1860
cgcggtgtca tctatgttac tagatcgggg atcgatcccc aattcgtaat catggtcata   1920
gctgtttcct gtgtgaaatt gttatccgct cacaattcca cacaacatac gagccggaag   1980
cataaagtgt aaagcctggg gtgcctaatg cgtgagctaa ctcacattaa ttgcgttgcg   2040
ctcactgccc gctttccagt cgggaaacct gtcgtgccag ctgcattaat gaatcggcca   2100
acgcgcgggg agaggcggtt tgcgtattgg gcgctcttcc gcttcctcgc tcactgactc   2160
gctgcgctcg tcgttcggc tgcggcgagc ggtatcagct cactcaaagg cggtaatacg   2220
gttatccaca gaatcagggg ataacgcagg aaagaacatg tgagcaaaag gccagcaaaa   2280
ggccaggaac cgtaaaaagg ccgcgttgct ggcgtttttc cataggctcc gcccccctga   2340
cgagcatcac aaaaatcgac gctcaagtca gaggtggcga aacccgacag gactataaag   2400
ataccaggcg tttccccctg gaagctccct cgtgcgctct cctgttccga ccctgccgct   2460
taccggatac ctgtccgcct ttctcccttc gggaagcgtg gcgctttctc aatgctcacg   2520
ctgtaggtat ctcagttcgg tgtaggtcgt tcgctccaag ctgggtgtg tgcacgaacc   2580 ccccgttcag cccgaccgct gcgccttatc cggtaactat cgtcttgagt ccaacccggt   2640
aagacacgac ttatcgccac tggcagcagc cactggtaac aggattagca gagcgaggta   2700
tgtaggcggt gctacagagt tcttgaagtg gtggcctaac tacggctaca ctagaaggac   2760
agtatttggt atctgcgctc tgctgaagcc agttaccttc ggaaaaagag ttggtagctc   2820
ttgatccggc aaacaaacca ccgctggtag cggtggtttt tttgtttgca agcagcagat   2880
tacgcgcaga aaaaaaggat ctcaagaaga tccctttgatc ttttctacgg ggtctgacgc   2940
```

```
tcagtggaac gaaaactcac gttaagggat tttggtcatg agattatcaa aaaggatctt     3000
cacctagatc cttttaaatt aaaaatgaag ttttaaatca atctaaagta tatatgagta     3060
aacttggtct gacagttacc aatgcttaat cagtgaggca cctatctcag cgatctgtct     3120
atttcgttca tccatagttg cctgactccc cgtcgtgtag ataactacga tacgggaggg     3180
cttaccatct ggccccagtg ctgcaatgat accgcgagac ccacgctcac cggctccaga     3240
tttatcagca ataaaccagc cagccggaag ggccgagcgc agaagtggtc ctgcaacttt     3300
atccgcctcc atccagtcta ttaattgttg ccgggaagct agagtaagta gttcgccagt     3360
taatagtttg cgcaacgttg ttgccattgc tacaggcatc gtggtgtcac gctcgtcgtt     3420
tggtatggct tcattcagct ccggttccca acgatcaagg cgagttacat gatcccccat     3480
gttgtgcaaa aaagcggtta gctccttcgg tcctccgatc gttgtcagaa gtaagttggc     3540
cgcagtgtta tcactcatgg ttatggcagc actgcataat tctcttactg tcatgccatc     3600
cgtaagatgc ttttctgtga ctggtgagta ctcaaccaag tcattctgag aatagtgtat     3660
gcggcgaccg agttgctctt gcccggcgtc aatacgggat aataccgcgc cacatagcag     3720
aactttaaaa gtgctcatca ttggaaaacg ttcttcgggg cgaaaactct caaggatctt     3780
aggcgtgttg agatccagtt cgatgtaacc cactcgtgca cccaactgat cttcagcatc     3840
ttttactttc accagcgttt ctgggtgagc aaaaacagga aggcaaaatg ccgcaaaaaa     3900
gggaataagg gcgacacgga aatgttgaat actcatactc ttcctttttc aatattattg     3960
aagcatttat cagggttatt gtctcatgag cggatacata tttgaatgta tttagaaaaa     4020
taaacaaata ggggttccgc gcacatttcc ccgaaaagtg ccacctgacg tctaagaaac     4080
cattattatc atgacattaa cctataaaaa taggcgtatc acgaggccct ttcgtc         4136

<210> SEQ ID NO 7
<211> LENGTH: 4133
<212> TYPE: DNA
<213> ORGANISM: artificial
<220> FEATURE:
<223> OTHER INFORMATION: pDOW2162

<400> SEQUENCE: 7
tcgcgcgttt cggtgatgac ggtgaaaacc tctgacacat gcagctcccg gagacggtca       60
cagcttgtct gtaagcggat gccgggagca gacaagcccg tcagggcgcg tcagcgggtg      120
ttggcgggtg tcggggctgg cttaactatg cggcatcaga gcagattgta ctgagagtgc      180
accatatgcg gtgtgaaata ccgcacagat gcgtaaggag aaaataccgc atcaggcgcc      240
attcgccatt caggctgcgc aactgttggg aagggcgatc ggtgcgggcc tcttcgctat      300
tacgccagct ggcgaaaggg ggatgtgctg caaggcgatt aagttgggta acgccagggt      360
tttcccagtc acgacgttgt aaaacgacgg ccagtgccaa gcttccagaa ggtaattatc      420
caagatgtag catcaagaat ccaatgttta cgggaaaaac tatggaagta ttatgtgagc      480
tcagcaagaa gcagatcaat atgcggcaca tatgcaacct atgttcaaaa atgaagaatg      540
tacagataca agatcctata ctgccagaat acgaagaaga atacgtagaa attgaaaaag      600
aagaaccagg cgaagaaaag aatcttgaag acgtaagcac tgacgacaac aatgaaaaga      660
agaagataag gtcggtgatt gtgaaagaga catagaggac acatgtaagg tggaaaatgt      720
aagggcggaa agtaacctta tcacaaagga atcttatccc ccactactta tcctttttata      780 tttttccgtg tcattttgtc ccttgagttt tcctatataa ggaaccaagt tcggcatttg      840
tgaaaacaag aaaaaatttg gtgtaagcta ttttctttga agtactgagg atacaacttc      900
```

```
agagaaattt gtaagtttgt agatctcgat tctagaatgt ctacagtcgg aacagggaag    960
ttaactcgtg cacaacgaag ggctgcggcc cgtaagaaca agcggaacac tcgtgtggtc   1020
caacctgtta ttgtagaacc catcgcttca ggccaaggca aggctattaa agcatggacc   1080
ggttacagcg tatcgaagtg gaccgcctct tgtgcggctg ccgaagctaa agtaacctcg   1140
gctataacta tctctctccc taatgagcta tcgtccgaaa ggaacaagca gctcaaggta   1200
ggtagagttt tattatggct tgggttgctt cccagtgtta gtggcacagt gaaatcctgt   1260
gttacagaga cgcagactac tgctgctgcc tcctttcagg tggcattagc tgtggccgac   1320
aacgggatcc gtattatttt caatggcaaa gatctcaatc tcgtggaacg tcgtattgct   1380
gctgtgaatc cttctgatcc tctcgggatc ctgtcgaaag atgttgtcgc tgctatgtac   1440
cccgaggcgt ttaagggtat aacccttgaa caactcaccg cggatttaac gatctacttg   1500
tacagcagtg cggctctcac tgagggcgac gtcatcgtgc atttggaggt tgagcatgtc   1560
agacctacgt ttgacgactc tttcactccg tattagtaag aattcgagct cggtaccgga   1620
tccaattccc gatcgttcaa acatttggca ataaagtttc ttaagattga atcctgttgc   1680
cggtcttgcg atgattatca tataatttct gttgaattac gttaagcatg taataattaa   1740
catgtaatgc atgacgttat ttatgagatg gttttttatg attagagtcc cgcaattata   1800
catttaatac gcgatagaaa acaaaatata gcgcgcaaac taggataaat tatcgcgcgc   1860
ggtgtcatct atgttactag atcggggatc gatccccaat tcgtaatcat ggtcatagct   1920
gtttcctgtg tgaaattgtt atccgctcac aattccacac aacatacgag ccggaagcat   1980
aaagtgtaaa gcctggggtg cctaatgcgt gagctaactc acattaattg cgttgcgctc   2040
actgcccgct ttccagtcgg gaaacctgtc gtgccagctg cattaatgaa tcggccaacg   2100
cgcggggaga ggcggtttgc gtattgggcg ctcttccgct tcctcgctca ctgactcgct   2160
gcgctcggtc gttcggctgc ggcgagcggt atcagctcac tcaaaggcgg taatacggtt   2220
atccacagaa tcaggggata acgcaggaaa gaacatgtga gcaaaaggcc agcaaaaggc   2280
caggaaccgt aaaaaggccg cgttgctggc gtttttccat aggctccgcc ccctgacga   2340 gcatcacaaa aatcgacgct caagtcagag gtggcgaaac ccgacaggac tataaagata   2400
ccaggcgttt ccccctggaa gctccctcgt gcgctctcct gttccgaccc tgccgcttac   2460
cggatacctg tccgcctttc tcccttcggg aagcgtggcg ctttctcaat gctcacgctg   2520
taggtatctc agttcggtgt aggtcgttcg ctccaagctg ggctgtgtgc acgaaccccc   2580
cgttcagccc gaccgctgcg ccttatccgg taactatcgt cttgagtcca acccggtaag   2640
acacgactta tcgccactgg cagcagccac tggtaacagg attagcagag cgaggtatgt   2700
aggcggtgct acagagttct tgaagtggtg gcctaactac ggctacacta aggacagt   2760 atttggtatc tgcgctctgc tgaagccagt taccttcgga aaaagagttg gtagctcttg   2820
atccggcaaa caaaccaccg ctggtagcgg tggtttttt gtttgcaagc agcagattac   2880
gcgcagaaaa aaaggatctc aagaagatcc tttgatcttt tctacggggt ctgacgctca   2940
gtggaacgaa aactcacgtt aagggatttt ggtcatgaga ttatcaaaaa ggatcttcac   3000
ctagatcctt ttaaattaaa aatgaagttt taaatcaatc taaagtatat atgagtaaac   3060
ttggtctgac agttaccaat gcttaatcag tgaggcacct atctcagcga tctgtctatt   3120
tcgttcatcc atagttgcct gactccccgt cgtgtagata actacgatac gggagggctt   3180
accatctggc cccagtgctg caatgatacc gcgagaccca cgctcaccgg ctccagattt   3240
atcagcaata aaccagccag ccggaagggc cgagcgcaga agtggtcctg caactttatc   3300
```

| | |
|---|---|
| cgcctccatc cagtctatta attgttgccg ggaagctaga gtaagtagtt cgccagttaa | 3360 |
| tagtttgcgc aacgttgttg ccattgctac aggcatcgtg gtgtcacgct cgtcgtttgg | 3420 |
| tatggcttca ttcagctccg gttcccaacg atcaaggcga gttacatgat cccccatgtt | 3480 |
| gtgcaaaaaa gcggttagct ccttcggtcc tccgatcgtt gtcagaagta agttggccgc | 3540 |
| agtgttatca ctcatggtta tggcagcact gcataattct cttactgtca tgccatccgt | 3600 |
| aagatgcttt tctgtgactg gtgagtactc aaccaagtca ttctgagaat agtgtatgcg | 3660 |
| gcgaccgagt tgctcttgcc cggcgtcaat acgggataat accgcgccac atagcagaac | 3720 |
| tttaaaagtg ctcatcattg gaaaacgttc ttcggggcga aaactctcaa ggatcttagg | 3780 |
| cgtgttgaga tccagttcga tgtaacccac tcgtgcaccc aactgatctt cagcatcttt | 3840 |
| tactttcacc agcgtttctg ggtgagcaaa aacaggaagg caaaatgccg caaaaaaggg | 3900 |
| aataagggcg acacggaaat gttgaatact catactcttc cttttcaat attattgaag | 3960 |
| catttatcag ggttattgtc tcatgagcgg atacatattt gaatgtattt agaaaaataa | 4020 |
| acaaataggg gttccgcgca catttccccg aaaagtgcca cctgacgtct aagaaaccat | 4080 |
| tattatcatg acattaacct ataaaaatag gcgtatcacg aggcccttc gtc | 4133 |

<210> SEQ ID NO 8
<211> LENGTH: 4133
<212> TYPE: DNA
<213> ORGANISM: artificial
<220> FEATURE:
<223> OTHER INFORMATION: pDOW2163

<400> SEQUENCE: 8

| | |
|---|---|
| tcgcgcgttt cggtgatgac ggtgaaaacc tctgacacat gcagctcccg gagacggtca | 60 |
| cagcttgtct gtaagcggat gccgggagca gacaagcccg tcagggcgcg tcagcgggtg | 120 |
| ttggcgggtg tcgggctgg cttaactatg cggcatcaga gcagattgta ctgagagtgc | 180 |
| accatatgcg gtgtgaaata ccgcacagat gcgtaaggag aaaataccgc atcaggcgcc | 240 |
| attcgccatt caggctgcgc aactgttggg aagggcgatc ggtgcgggcc tcttcgctat | 300 |
| tacgccagct ggcgaaaggg ggatgtgctg caaggcgatt aagttgggta acgccagggt | 360 |
| tttcccagtc acgacgttgt aaaacgacgg ccagtgccaa gcttccagaa ggtaattatc | 420 |
| caagatgtag catcaagaat ccaatgttta cgggaaaaac tatggaagta ttatgtgagc | 480 |
| tcagcaagaa gcagatcaat atgcggcaca tatgcaacct atgttcaaaa atgaagaatg | 540 |
| tacagataca agatcctata ctgccagaat acgaagaaga atacgtagaa attgaaaaag | 600 |
| aagaaccagg cgaagaaaag aatcttgaag acgtaagcac tgacgacaac aatgaaaaga | 660 |
| agaagataag gtcggtgatt gtgaaagaga catagaggac acatgtaagg tggaaaatgt | 720 |
| aagggcggaa agtaacctta tcacaaagga atcttatccc ccactactta tcctttata | 780 |
| tttttccgtg tcattttgc ccttgagttt tcctataaa ggaaccaagt tcggcatttg | 840 |
| tgaaaacaag aaaaaatttg gtgtaagcta ttttctttga agtactgagg atacaacttc | 900 |
| agagaaattt gtaagtttgt agatctcgat tctagaatgt ctacagtcgg aacagggaag | 960 |
| ttaactcgtg cacaacgaag ggctgcggcc cgtaagaaca agcggaacac tcgtgtggtc | 1020 |
| caacctgtta ttgtagaacc catcgcttca ggccaaggca aggctattaa agcatggacc | 1080 |
| ggttacagcg tatcgaagtg gaccgcctct tgtgcggctg ccgaagctaa agtaacctcg | 1140 |
| gctataacta tctctctccc taatgagcta tcgtccgaaa ggaacaagca gctcaaggta | 1200 |
| ggtagagttt tattatggct tgggttgctt cccagtgtta gtggcacagt gaaatcctgt | 1260 |

```
gttacagaga cgcagactac tgctgctgcc tcctttcagg tggcattagc tgtggccgac    1320
aacgggatcc gtattatttt caatggcaaa gatctcaatc tcgtggaacg tcgtattgct    1380
gctgtgaatc cttctgatcc tctcgggatc ctgtcgaaag atgttgtcgc tgctatgtac    1440
cccgaggcgt ttaagggtat aacccttgaa caactcaccg cggatttaac gatctacttg    1500
tacagcagtg cggctctcac tgagggcgac gtcatcgtgc atttggaggt tgagcatgtc    1560
agacctacgt ttgacgactc tttcactccg tattagtaag aattcgagct cggtaccgga    1620
tccaattccc gatcgttcaa acatttggca ataaagtttc ttaagattga atcctgttgc    1680
cggtcttgcg atgattatca tataatttct gttgaattac gttaagcatg taataattaa    1740
catgtaatgc atgacgttat ttatgagatg ggttttatg attagagtcc cgcaattata    1800
catttaatac gcgatagaaa acaaaatata gcgcgcaaac taggataaat tatcgcgcgc    1860
ggtgtcatct atgttactag atcgggatc gatccccaat tcgtaatcat ggtcatagct    1920
gtttcctgtg tgaaattgtt atccgctcac aattccacac aacatacgag ccggaagcat    1980
aaagtgtaaa gcctggggtg cctaatgcgt gagctaactc acattaattg cgttgcgctc    2040
actgcccgct ttccagtcgg gaaacctgtc gtgccagctg cattaatgaa tcggccaacg    2100
cgcggggaga ggcggtttgc gtattgggcg ctcttccgct tcctcgctca ctgactcgct    2160
gcgctcggtc gttcggctgc ggcgagcggt atcagctcac tcaaaggcgg taatacggtt    2220
atccacagaa tcaggggata acgcaggaaa gaacatgtga gcaaaaggcc agcaaaaggc    2280
caggaaccgt aaaaaggccg cgttgctggc gtttttccat aggctccgcc ccctgacga    2340 gcatcacaaa aatcgacgct caagtcagag gtggcgaaac ccgacaggac tataaagata    2400
ccaggcgttt cccctggaa gctccctcgt gcgctctcct gttccgaccc tgccgcttac    2460
cggatacctg tccgcctttc tcccttcggg aagcgtggcg ctttctcaat gctcacgctg    2520
taggtatctc agttcggtgt aggtcgttcg ctccaagctg ggtgtgtgc acgaaccccc    2580 cgttcagccc gaccgctgcg ccttatccgg taactatcgt cttgagtcca acccggtaag    2640
acacgactta tcgccactgg cagcagccac tggtaacagg attagcagag cgaggtatgt    2700
aggcggtgct acagagttct tgaagtggtg gcctaactac ggctacacta aaggacagt    2760 atttggtatc tgcgctctgc tgaagccagt taccttcgga aaaagagttg gtagctcttg    2820
atccggcaaa caaaccaccg ctggtagcgg tggttttttt gtttgcaagc agcagattac    2880
gcgcagaaaa aaaggatctc aagaagatcc tttgatcttt tctacggggt ctgacgctca    2940
gtggaacgaa aactcacgtt aagggatttt ggtcatgaga ttatcaaaaa ggatcttcac    3000
ctagatcctt ttaaattaaa aatgaagttt taaatcaatc taaagtatat atgagtaaac    3060
ttggtctgac agttaccaat gcttaatcag tgaggcacct atctcagcga tctgtctatt    3120
tcgttcatcc atagttgcct gactccccgt cgtgtagata actacgatac gggagggctt    3180
accatctggc cccagtgctg caatgatacc gcgagaccca cgctcaccgg ctccagattt    3240
atcagcaata aaccagccag ccggaagggc cgagcgcaga agtggtcctg caactttatc    3300
cgcctccatc cagtctatta attgttgccg ggaagctaga gtaagtagtt cgccagttaa    3360
tagtttcgcc aacgttgttg ccattgctac aggcatcgtg gtgtcacgct cgtcgtttgg    3420
tatggcttca ttcagctccg gttcccaacg atcaaggcga gttacatgat cccccatgtt    3480
gtgcaaaaaa gcggttagct ccttcggtcc tccgatcgtt gtcagaagta agttggccgc    3540
agtgttatca ctcatggtta tggcagcact gcataattct cttactgtca tgccatccgt    3600
aagatgcttt tctgtgactg gtgagtactc aaccaagtca ttctgagaat agtgtatgcg    3660
```

-continued

```
gcgaccgagt tgctcttgcc cggcgtcaat acgggataat accgcgccac atagcagaac    3720
tttaaaagtg ctcatcattg gaaaacgttc ttcggggcga aaactctcaa ggatcttagg    3780
cgtgttgaga tccagttcga tgtaacccac tcgtgcaccc aactgatctt cagcatcttt    3840
tactttcacc agcgtttctg ggtgagcaaa acaggaagg caaaatgccg caaaaaggg      3900 aataagggcg acacggaaat gttgaatact catactcttc cttttcaat attattgaag     3960 catttatcag ggttattgtc tcatgagcgg atacatattt gaatgtattt agaaaaataa    4020
acaaataggg gttccgcgca catttccccg aaaagtgcca cctgacgtct aagaaaccat    4080
tattatcatg acattaacct ataaaaatag gcgtatcacg aggccctttc gtc           4133
```

<210> SEQ ID NO 9
<211> LENGTH: 4290
<212> TYPE: DNA
<213> ORGANISM: artificial
<220> FEATURE:
<223> OTHER INFORMATION: pDOW2169

<400> SEQUENCE: 9

```
tcgcgcgttt cggtgatgac ggtgaaaacc tctgacacat gcagctcccg gagacggtca     60
cagcttgtct gtaagcggat gccgggagca gacaagcccg tcaggcgcg tcagcgggtg     120 ttggcgggtg tcgggctgg cttaactatg cggcatcaga gcagattgta ctgagagtgc     180
accatatgcg gtgtgaaata ccgcacagat gcgtaaggag aaaataccgc atcaggcgcc     240
attcgccatt caggctgcgc aactgttggg aagggcgatc ggtgcgggcc tcttcgctat     300
tacgccagct ggcgaaaggg ggatgtgctg caaggcgatt aagttgggta acgccagggt     360
tttcccagtc acgacgttgt aaaacgacgg ccagtgccaa gcttccagaa ggtaattatc     420
caagatgtag catcaagaat ccaatgttta cgggaaaaac tatggaagta ttatgtgagc     480
tcagcaagaa gcagatcaat atgcggcaca tatgcaacct atgttcaaaa atgaagaatg     540
tacagataca agatcctata ctgccagaat acgaagaaga atacgtagaa attgaaaaag     600
aagaaccagg cgaagaaaag aatcttgaag acgtaagcac tgacgacaac aatgaaaaga     660
agaagataag gtcggtgatt gtgaaagaga catagaggac acatgtaagg tggaaaatgt     720
aagggcggaa agtaacccta tcacaaagga atcttatccc ccactactta tccttttata     780
tttttccgtg tcatttttgc ccttgagttt tcctatataa ggaaccaagt tcggcatttg     840
tgaaaacaag aaaaaatttg gtgtaagcta ttttctttga agtactgagg atacaacttc     900
agagaaattt gtaagtttgt agatctcgat tctagaatgt ctacagtcgg aacagggaag     960
ttaactcgtg cacaacgaag ggctgcggcc cgtaagaaca gcggaacac tcgtgtggtc    1020 caacctgtta ttgtagaacc catcgcttca ggccaaggca aggctattaa agcatggacc    1080
ggttacagcg tatcgaagtg gaccgcctct tgtgcggctg ccgaagctaa agtaacctcg    1140
gctataacta tctctctccc taatgagcta tcgtccgaaa ggaacaagca gctcaaggta    1200
ggtagagttt tattatggct tgggttgctt cccagtgtta gtggcacagt gaaatcctgt    1260
gttacagaga cgcagactac tgctgctgcc tcctttcagg tggcattagc tgtggccgac    1320
aacgggatcc ttagtaattc tcgtaagaaa cgttctacct ctgctggccc taccgtgcct    1380
gatcgtaata atgatggcat tcctgatggg atcctgtcga aagatgttgt cgctgctatg    1440
taccccgagg cgtttaaggg tataacccct gaacaactca ccgcggattt aacgatctac    1500
ttgtacagca gtgcggctct cactgagggc gacgtcatcg tgcatttgga ggttgagcat    1560
gtcagaccta cgtttgacga ctcttttcact ccggtgtatt agtgcccgct gaagagcgtt    1620
```

```
acactagtgt ggcctacttg aaggctagtt ataaccgttt ctttaaacgg taatcgttgt    1680
tgaaacgtct tccttttaca agaggattga gctgcccttg ggttttactc cttgaaccct    1740
tcggaagaac tctttggaat tcgagctcgg taccggatcc aattcccgat cgttcaaaca    1800
tttggcaata aagtttctta agattgaatc ctgttgccgg tcttgcgatg attatcatat    1860
aatttctgtt gaattacgtt aagcatgtaa taattaacat gtaatgcatg acgttattta    1920
tgagatgggt ttttatgatt agagtcccgc aattatacat ttaatacgcg atagaaaaca    1980
aaatatagcg cgcaaactag gataaattat cgcgcgcggt gtcatctatg ttactagatc    2040
ggggatcgat ccccaattcg taatcatggt catagctgtt tcctgtgtga aattgttatc    2100
cgctcacaat tccacacaac atacgagccg aagcataaa gtgtaaagcc tggggtgcct    2160
aatgcgtgag ctaactcaca ttaattgcgt tgcgctcact gcccgctttc cagtcgggaa    2220
acctgtcgtg ccagctgcat taatgaatcg gccaacgcgc ggggagaggc ggtttgcgta    2280
ttgggcgctc ttccgcttcc tcgctcactg actcgctgcg ctcggtcgtt cggctgcggc    2340
gagcggtatc agctcactca aaggcggtaa tacggttatc cacagaatca ggggataacg    2400
caggaaagaa catgtgagca aaaggccagc aaaaggccag gaaccgtaaa aaggccgcgt    2460
tgctggcgtt tttccatagg ctccgccccc ctgacgagca tcacaaaaat cgacgctcaa    2520
gtcagaggtg gcgaaacccg acaggactat aaagatacca ggcgtttccc cctggaagct    2580
ccctcgtgcg ctctcctgtt ccgaccctgc cgcttaccgg atacctgtcc gcctttctcc    2640
cttcgggaag cgtggcgctt tctcaatgct cacgctgtag gtatctcagt tcggtgtagg    2700
tcgttcgctc caagctgggg tgtgtgcacg aaccccccgt tcagcccgac cgctgcgcct    2760
tatccggtaa ctatcgtctt gagtccaacc cggtaagaca cgacttatcg ccactggcag    2820
cagccactgg taacaggatt agcagagcga ggtatgtagg cggtgctaca gagttcttga    2880
agtggtggcc taactacggc tacactagaa ggacagtatt tggtatctgc gctctgctga    2940
agccagttac cttcggaaaa agagttggta gctcttgatc cggcaaacaa accaccgctg    3000
gtagcggtgg tttttttgtt tgcaagcagc agattacgcg cagaaaaaaa ggatctcaag    3060
aagatccttt gatcttttct acggggtctg acgctcagtg gaacgaaaac tcacgttaag    3120
ggattttggt catgagatta tcaaaaagga tcttcaccta gatccttta aattaaaaat    3180 gaagttttaa atcaatctaa agtatatatg agtaaacttg gtctgacagt taccaatgct    3240
taatcagtga ggcacctatc tcagcgatct gtctatttcg ttcatccata gttgcctgac    3300
tccccgtcgt gtagataact acgatacggg agggcttacc atctggcccc agtgctgcaa    3360
tgataccgcg agacccacgc tcaccggctc cagatttatc agcaataaac cagccagccg    3420
gaagggccga gcgcagaagt ggtcctgcaa ctttatccgc ctccatccag tctattaatt    3480
gttgccggga agctagagta agtagttcgc cagttaatag tttgcgcaac gttgttgcca    3540
ttgctacagg catcgtggtg tcacgctcgt cgtttggtat ggcttcattc agctccggtt    3600
cccaacgatc aaggcgagtt acatgatccc ccatgttgtg caaaaaagcg gttagctcct    3660
tcggtcctcc gatcgttgtc agaagtaagt tggccgcagt gttatcactc atggttatgg    3720
cagcactgca taattctctt actgtcatgc catccgtaag atgcttttct gtgactggtg    3780
agtactcaac caagtcattc tgagaatagt gtatgcggcg accgagttgc tcttgcccgg    3840
cgtcaatacg ggataatacc gcgccacata gcagaacttt aaaagtgctc atcattggaa    3900
aacgttcttc ggggcgaaaa ctctcaagga tcttaggcgt gttgagatcc agttcgatgt    3960
aacccactcg tgcacccaac tgatcttcag catcttttac tttcaccagc gtttctgggt    4020
```

```
gagcaaaaac aggaaggcaa aatgccgcaa aaagggaat aagggcgaca cggaaatgtt    4080
gaatactcat actcttcctt tttcaatatt attgaagcat ttatcagggt tattgtctca    4140
tgagcggata catatttgaa tgtatttaga aaaataaaca aatagggggtt ccgcgcacat    4200 ttccccgaaa agtgccacct gacgtctaag aaaccattat tatcatgaca ttaacctata    4260
aaaataggcg tatcacgagg ccctttcgtc                                     4290

<210> SEQ ID NO 10
<211> LENGTH: 4290
<212> TYPE: DNA
<213> ORGANISM: artificial
<220> FEATURE:
<223> OTHER INFORMATION: pDOW2170

<400> SEQUENCE: 10
tcgcgcgttt cggtgatgac ggtgaaaacc tctgacacat gcagctcccg gagacggtca      60
cagcttgtct gtaagcggat gccgggagca gacaagcccg tcaggcgcg tcagcggtg      120 ttggcgggtg tcggggctgg cttaactatg cggcatcaga gcagattgta ctgagagtgc     180
accatatgcg gtgtgaaata ccgcacagat gcgtaaggag aaaataccgc atcaggcgcc     240
attcgccatt caggctgcgc aactgttggg aagggcgatc ggtgcgggcc tcttcgctat     300
tacgccagct ggcgaaaggg ggatgtgctg caaggcgatt aagttgggta acgccagggt     360
tttcccagtc acgacgttgt aaaacgacgg ccagtgccaa gcttccagaa ggtaattatc     420
caagatgtag catcaagaat ccaatgttta cgggaaaaac tatggaagta ttatgtgagc     480
tcagcaagaa gcagatcaat atgcggcaca tatgcaacct atgttcaaaa atgaagaatg     540
tacagataca agatcctata ctgccagaat acgaagaaga atacgtagaa attgaaaaag     600
aagaaccagg cgaagaaaag aatcttgaag acgtaagcac tgacgacaac aatgaaaaga     660
agaagataag gtcggtgatt gtgaaagaga catagaggac acatgtaagg tggaaaatgt     720
aagggcggaa agtaaccttca tcacaaagga atcttatccc ccactactta tcctttttata     780 ttttccgtg tcatttttgc ccttgagttt tcctatataa ggaaccaagt tcggcatttg     840
tgaaaacaag aaaaaatttg gtgtaagcta ttttctttga agtactgagg atacaacttc     900
agagaaattt gtaagtttgt agatctcgat tctagaatgt ctacagtcgg aacagggaag     960
ttaactcgtg cacaacgaag ggctgcggcc cgtaagaaca agcggaacac tcgtgtggtc    1020
caacctgtta ttgtagaacc catcgcttca ggccaaggca aggctattaa agcatggacc    1080
ggttacagcg tatcgaagtg gaccgcctct tgtgcggctg ccgaagctaa agtaacctcg    1140
gctataacta tctctctccc taatgagcta tcgtccgaaa ggaacaagca gctcaaggta    1200
ggtagagttt tattatggct tgggttgctt cccagtgtta gtggcacagt gaaatcctgt    1260
gttacagaga cgcagactac tgctgctgcc tccttttcagg tggcattagc tgtggccgac    1320
aacgggatcc ttagtcctga agctcgtcat cctctcgtgg ctgcgtatcc tattgtgcat    1380
gttgatatgg aaaatattat cctctctggg atcctgtcga agatgttgt cgctgctatg    1440 taccccgagg cgtttaaggg tataacccctt gaacaactca ccgcggattt aacgatctac    1500
ttgtacagca gtgcggctct cactgagggc gacgtcatcg tgcatttgga ggttgagcat    1560
gtcagaccta cgtttgacga ctctttcact ccggtgtatt agtgcccgct gaagagcgtt    1620
acactagtgt ggcctacttg aaggctagtt ataaccgttt cttttaaacgg taatcgttgt    1680 tgaaacgtct tccttttaca agaggattga gctgcccttg ggtttttactc cttgaaccct    1740 tcggaagaac tctttggaat tcgagctcgg taccggatcc aattcccgat cgttcaaaca    1800
```

```
tttggcaata aagtttctta agattgaatc ctgttgccgg tcttgcgatg attatcatat    1860
aatttctgtt gaattacgtt aagcatgtaa taattaacat gtaatgcatg acgttattta    1920
tgagatgggt ttttatgatt agagtcccgc aattatacat ttaatacgcg atagaaaaca    1980
aaatatagcg cgcaaactag gataaattat cgcgcgcggt gtcatctatg ttactagatc    2040
ggggatcgat ccccaattcg taatcatggt catagctgtt tcctgtgtga aattgttatc    2100
cgctcacaat tccacacaac atacgagccg gaagcataaa gtgtaaagcc tggggtgcct    2160
aatgcgtgag ctaactcaca ttaattgcgt tgcgctcact gcccgctttc cagtcgggaa    2220
acctgtcgtg ccagctgcat taatgaatcg gccaacgcgc ggggagaggc ggtttgcgta    2280
ttgggcgctc ttccgcttcc tcgctcactg actcgctgcg ctcggtcgtt cggctgcggc    2340
gagcggtatc agctcactca aaggcggtaa tacggttatc cacagaatca ggggataacg    2400
caggaaagaa catgtgagca aaaggccagc aaaaggccag gaaccgtaaa aaggccgcgt    2460
tgctggcgtt tttccatagg ctccgccccc ctgacgagca tcacaaaaat cgacgctcaa    2520
gtcagaggtg gcgaaacccg acaggactat aaagatacca ggcgtttccc cctggaagct    2580
ccctcgtgcg ctctcctgtt ccgaccctgc cgcttaccgg atacctgtcc gcctttctcc    2640
cttcgggaag cgtggcgctt tctcaatgct cacgctgtag gtatctcagt tcggtgtagg    2700
tcgttcgctc caagctgggg tgtgtgcacg aaccccccgt tcagcccgac cgctgcgcct    2760
tatccggtaa ctatcgtctt gagtccaacc cggtaagaca cgacttatcg ccactggcag    2820
cagccactgg taacaggatt agcagagcga ggtatgtagg cggtgctaca gagttcttga    2880
agtggtggcc taactacggc tacactagaa ggacagtatt tggtatctgc gctctgctga    2940
agccagttac cttcggaaaa agagttggta gctcttgatc cggcaaacaa accaccgctg    3000
gtagcggtgg tttttttgtt tgcaagcagc agattacgcg cagaaaaaaa ggatctcaag    3060
aagatccttt gatcttttct acggggtctg acgctcagtg gaacgaaaac tcacgttaag    3120
ggattttggt catgagatta tcaaaaagga tcttcaccta gatcctttta aattaaaaat    3180
gaagttttaa atcaatctaa agtatatatg agtaaacttg gtctgacagt taccaatgct    3240
taatcagtga ggcacctatc tcagcgatct gtctatttcg ttcatccata gttgcctgac    3300
tccccgtcgt gtagataact acgatacggg agggcttacc atctggcccc agtgctgcaa    3360
tgataccgcg agacccacgc tcaccggctc cagatttatc agcaataaac cagccagccg    3420
gaagggccga gcgcagaagt ggtcctgcaa ctttatccgc ctccatccag tctattaatt    3480
gttgccggga agctagagta agtagttcgc cagttaatag tttgcgcaac gttgttgcca    3540
ttgctacagg catcgtggtg tcacgctcgt cgtttggtat ggcttcattc agctccggtt    3600
cccaacgatc aaggcgagtt acatgatccc ccatgttgtg caaaaaagcg gttagctcct    3660
tcggtcctcc gatcgttgtc agaagtaagt tggccgcagt gttatcactc atggttatgg    3720
cagcactgca taattctctt actgtcatgc catccgtaag atgcttttct gtgactggtg    3780
agtactcaac caagtcattc tgagaatagt gtatgcggcg accgagttgc tcttgcccgg    3840
cgtcaatacg ggataatacc gcgccacata gcagaacttt aaaagtgctc atcattggaa    3900
aacgttcttc ggggcgaaaa ctctcaagga tcttaggcgt gttgagatcc agttcgatgt    3960
aacccactcg tgcacccaac tgatcttcag catcttttac tttcaccagc gtttctgggt    4020
gagcaaaaac aggaaggcaa aatgccgcaa aaaagggaat aagggcgaca cggaaatgtt    4080
gaatactcat actcttcctt tttcaatatt attgaagcat ttatcagggt tattgtctca    4140
tgagcggata catatttgaa tgtatttaga aaaataaaca aataggggtt ccgcgcacat    4200
```

<210> SEQ ID NO 11
<211> LENGTH: 4287
<212> TYPE: DNA
<213> ORGANISM: artificial
<220> FEATURE:
<223> OTHER INFORMATION: pDOW2171

<400> SEQUENCE: 11

```
tcgcgcgttt cggtgatgac ggtgaaaacc tctgacacat gcagctcccg gagacggtca    60
cagcttgtct gtaagcggat gccgggagca gacaagcccg tcaggcgcgc tcagcgggtg   120
ttggcgggtg tcgggctgg cttaactatg cggcatcaga gcagattgta ctgagagtgc    180
accatatgcg gtgtgaaata ccgcacagat gcgtaaggag aaaataccgc atcaggcgcc   240
attcgccatt caggctgcgc aactgttggg aagggcgatc ggtgcgggcc tcttcgctat   300
tacgccagct ggcgaaaggg ggatgtgctg caaggcgatt aagttgggta acgccagggt   360
tttcccagtc acgacgttgt aaaacgacgg ccagtgccaa gcttccagaa ggtaattatc   420
caagatgtag catcaagaat ccaatgttta cgggaaaaac tatggaagta ttatgtgagc   480
tcagcaagaa gcagatcaat atgcggcaca tatgcaacct atgttcaaaa atgaagaatg   540
tacagataca agatcctata ctgccagaat acgaagaaga atacgtagaa attgaaaaag   600
aagaaccagg cgaagaaaag aatcttgaag acgtaagcac tgacgacaac aatgaaaaga   660
agaagataag gtcggtgatt gtgaaagaga catagaggac acatgtaagg tggaaaatgt   720
aagggcggaa agtaacctta tcacaaagga atcttatccc ccactactta tcctttata   780
ttttccgtg tcatttttgc ccttgagttt tcctatataa ggaaccaagt tcggcatttg    840
tgaaaacaag aaaaaatttg gtgtaagcta ttttctttga agtactgagg atacaacttc   900
agagaaattt gtaagtttgt agatctcgat tctagaatgt ctacagtcgg aacagggaag   960
ttaactcgtg cacaacgaag ggctgcggcc cgtaagaaca gcggaacac tcgtgtggtc    1020
caacctgtta ttgtagaacc catcgcttca ggccaaggca aggctattaa agcatggacc   1080
ggttacagcg tatcgaagtg gaccgcctct tgtgcggctg ccgaagctaa agtaacctcg   1140
gctataacta tctctctccc taatgagcta tcgtccgaaa ggaacaagca gctcaaggta   1200
ggtagagttt tattatggct tgggttgctt cccagtgtta gtggcacagt gaaatcctgt   1260
gttacagaga cgcagactac tgctgctgcc tcctttcagg tggcattagc tgtggccgac   1320
aacgggatcc gtattatttt caatggcaaa gatctcaatc tcgtggaacg tcgtattgct   1380
gctgtgaatc cttctgatcc tctcgggatc ctgtcgaaag atgttgtcgc tgctatgtac   1440
cccgaggcgt ttaagggtat aacccttgaa caactcaccg cggatttaac gatctacttg   1500
tacagcagtg cggctctcac tgagggcgac gtcatcgtgc atttggaggt tgagcatgtc   1560
agacctacgt ttgacgactc tttcactccg gtgtattagt gcccgctgaa gagcgttaca   1620
ctagtgtggc ctacttgaag gctagttata accgttcttt taaacggtaa tcgttgttga   1680
aacgtcttcc ttttacaaga ggattgagct gcccttgggt tttactcctt gaacccttcg   1740
gaagaactct ttggaattcg agctcggtac cggatccaat tcccgatcgt tcaaacattt   1800
ggcaataaag tttcttaaga ttgaatcctg ttgccggtct tgcgatgatt atcatataat   1860
ttctgttgaa ttcgttaag catgtaataa ttaacatgta atgcatgacg ttatttatga   1920
gatgggtttt tatgattaga gtcccgcaat tatacattta atacgcgata gaaaacaaaa   1980
```

```
tatagcgcgc aaactaggat aaattatcgc gcgcggtgtc atctatgtta ctagatcggg    2040
gatcgatccc caattcgtaa tcatggtcat agctgtttcc tgtgtgaaat tgttatccgc    2100
tcacaattcc acacaacata cgagccggaa gcataaagtg taaagcctgg ggtgcctaat    2160
gcgtgagcta actcacatta attgcgttgc gctcactgcc cgctttccag tcgggaaacc    2220
tgtcgtgcca gctgcattaa tgaatcggcc aacgcgcggg gagaggcggt ttgcgtattg    2280
ggcgctcttc cgcttcctcg ctcactgact cgctgcgctc ggtcgttcgg ctgcggcgag    2340
cggtatcagc tcactcaaag gcggtaatac ggttatccac agaatcaggg gataacgcag    2400
gaaagaacat gtgagcaaaa ggccagcaaa aggccaggaa ccgtaaaaag gccgcgttgc    2460
tggcgttttt ccataggctc cgcccccctg acgagcatca caaaaatcga cgctcaagtc    2520
agaggtggcg aaacccgaca ggactataaa gataccaggc gtttccccct ggaagctccc    2580
tcgtgcgctc tcctgttccg accctgccgc ttaccggata cctgtccgcc tttctccctt    2640
cgggaagcgt ggcgctttct caatgctcac gctgtaggta tctcagttcg gtgtaggtcg    2700
ttcgctccaa gctgggtgt gtgcacgaac cccccgttca gcccgaccgc tgcgccttat    2760
ccggtaacta tcgtcttgag tccaacccgg taagacacga cttatcgcca ctggcagcag    2820
ccactggtaa caggattagc agagcgaggt atgtaggcgg tgctacagag ttcttgaagt    2880
ggtggcctaa ctacggctac actagaagga cagtatttgg tatctgcgct ctgctgaagc    2940
cagttacctt cggaaaaaga gttggtagct cttgatccgg caaacaaacc accgctggta    3000
gcggtggttt ttttgtttgc aagcagcaga ttacgcgcag aaaaaaagga tctcaagaag    3060
atcctttgat cttttctacg gggtctgacg ctcagtggaa cgaaaactca cgttaaggga    3120
ttttggtcat gagattatca aaaggatct tcacctagat ccttttaaat taaaaatgaa    3180
gttttaaatc aatctaaagt atatatgagt aaacttggtc tgacagttac caatgcttaa    3240
tcagtgaggc acctatctca gcgatctgtc tatttcgttc atccatagtt gcctgactcc    3300
ccgtcgtgta gataactacg atacgggagg gcttaccatc tggccccagt gctgcaatga    3360
taccgcgaga cccacgctca ccggctccag atttatcagc aataaaccag ccagccggaa    3420
gggccgagcg cagaagtggt cctgcaactt tatccgcctc catccagtct attaattgtt    3480
gccgggaagc tagagtaagt agttcgccag ttaatagttt gcgcaacgtt gttgccattg    3540
ctacaggcat cgtggtgtca cgctcgtcgt ttggtatggc ttcattcagc tccggttccc    3600
aacgatcaag gcgagttaca tgatccccca tgttgtgcaa aaaagcggtt agctccttcg    3660
gtcctccgat cgttgtcaga agtaagttgg ccgcagtgtt atcactcatg gttatggcag    3720
cactgcataa ttctcttact gtcatgccat ccgtaagatg cttttctgtg actggtgagt    3780
actcaaccaa gtcattctga gaatagtgta tgcggcgacc gagttgctct tgcccggcgt    3840
caatacggga taataccgcg ccacatagca gaactttaaa agtgctcatc attggaaaac    3900
gttcttcggg gcgaaaactc tcaaggatct taggcgtgtt gagatccagt tcgatgtaac    3960
ccactcgtgc acccaactga tcttcagcat cttttacttt caccagcgtt tctgggtgag    4020
caaaaacagg aaggcaaaat gccgcaaaaa agggaataag ggcgacacgg aaatgttgaa    4080
tactcatact cttccttttt caatattatt gaagcattta tcagggttat tgtctcatga    4140
gcggatacat atttgaatgt atttagaaaa ataaacaaat aggggttccg cgcacatttc    4200
cccgaaaagt gccacctgac gtctaagaaa ccattattat catgacatta acctataaaa    4260
ataggcgtat cacgaggccc tttcgtc                                        4287
```

<210> SEQ ID NO 12
<211> LENGTH: 4287
<212> TYPE: DNA
<213> ORGANISM: artificial
<220> FEATURE:
<223> OTHER INFORMATION: pDOW2172

<400> SEQUENCE: 12

```
tcgcgcgttt cggtgatgac ggtgaaaacc tctgacacat gcagctcccg gagacggtca      60
cagcttgtct gtaagcggat gccgggagca gacaagcccg tcagggcgcg tcagcgggtg     120
ttggcgggtg tcggggctgg cttaactatg cggcatcaga gcagattgta ctgagagtgc     180
accatatgcg gtgtgaaata ccgcacagat gcgtaaggag aaaataccgc atcaggcgcc     240
attcgccatt caggctgcgc aactgttggg aagggcgatc ggtgcgggcc tcttcgctat     300
tacgccagct ggcgaaaggg ggatgtgctg caaggcgatt aagttgggta acgccagggt     360
tttcccagtc acgacgttgt aaaacgacgg ccagtgccaa gcttccagaa ggtaattatc     420
caagatgtag catcaagaat ccaatgttta cgggaaaaac tatggaagta ttatgtgagc     480
tcagcaagaa gcagatcaat atgcggcaca tatgcaacct atgttcaaaa atgaagaatg     540
tacagataca agatcctata ctgccagaat acgaagaaga atacgtagaa attgaaaaag     600
aagaaccagg cgaagaaaag aatcttgaag acgtaagcac tgacgacaac aatgaaaaga     660
agaagataag gtcggtgatt gtgaaagaga catagaggac acatgtaagg tggaaaatgt     720
aagggcggaa agtaacctta tcacaaagga atcttatccc ccactactta tccttttata     780
tttttccgtg tcattttgc ccttgagttt tcctatataa ggaaccaagt tcggcatttg     840
tgaaaacaag aaaaaatttg gtgtaagcta ttttctttga agtactgagg atacaacttc     900
agagaaattt gtaagtttgt agatctcgat tctagaatgt ctacagtcgg aacagggaag     960
ttaactcgtg cacaacgaag ggctgcggcc cgtaagaaca agcggaacac tcgtgtggtc    1020
caacctgtta ttgtagaacc catcgcttca ggccaaggca aggctattaa agcatggacc    1080
ggttacagcg tatcgaagtg gaccgcctct tgtgcggctg ccgaagctaa agtaacctcg    1140
gctataacta tctctctccc taatgagcta tcgtccgaaa ggaacaagca gctcaaggta    1200
ggtagagttt tattatggct tgggttgctt cccagtgtta gtggcacagt gaaatcctgt    1260
gttacagaga cgcagactac tgctgctgcc tcctttcagg tggcattagc tgtgccgac     1320
aacgggatcc gtattatttt caatggcaaa gatctcaatc tcgtggaacg tcgtattgct    1380
gctgtgaatc cttctgatcc tctcgggatc ctgtcgaaag atgttgtcgc tgctatgtac    1440
cccgaggcgt ttaagggtat aacccttgaa caactcaccg cggatttaac gatctacttg    1500
tacagcagtg cggctctcac tgagggcgac gtcatcgtgc atttggaggt tgagcatgtc    1560
agacctacgt ttgacgactc tttcactccg gtgtattagt gcccgctgaa gagcgttaca    1620
ctagtgtggc ctacttgaag gctagttata accgtttctt taaacggtaa tcgttgttga    1680
aacgtcttcc ttttacaaga ggattgagct gcccttgggt tttactcctt gaaccctcg    1740
gaagaactct ttggaattcg agctcggtac cggatccaat tcccgatcgt tcaaacattt    1800
ggcaataaag tttcttaaga ttgaatcctg ttgccggtct tgcgatgatt atcatataat    1860
ttctgttgaa ttacgttaag catgtaataa ttaacatgta atgcatgacg ttatttatga    1920
gatgggtttt tatgattaga gtcccgcaat tatacattta atacgcgata gaaaacaaaa    1980
tatagcgcgc aaactaggat aaattatcgc gcgcggtgtc atctatgtta ctagatcggg    2040
gatcgatccc caattcgtaa tcatggtcat agctgtttcc tgtgtgaaat tgttatccgc    2100
tcacaattcc acacaacata cgagccggaa gcataaagtg taaagcctgg ggtgcctaat    2160
```

```
gcgtgagcta actcacatta attgcgttgc gctcactgcc cgctttccag tcgggaaacc    2220
tgtcgtgcca gctgcattaa tgaatcggcc aacgcgcggg gagaggcggt ttgcgtattg    2280
ggcgctcttc cgcttcctcg ctcactgact cgctgcgctc ggtcgttcgg ctgcggcgag    2340
cggtatcagc tcactcaaag gcggtaatac ggttatccac agaatcaggg gataacgcag    2400
gaaagaacat gtgagcaaaa ggccagcaaa aggccaggaa ccgtaaaaag gccgcgttgc    2460
tggcgttttt ccataggctc cgcccccctg acgagcatca caaaaatcga cgctcaagtc    2520
agaggtggcg aaacccgaca ggactataaa gataccaggc gtttccccct ggaagctccc    2580
tcgtgcgctc tcctgttccg accctgccgc ttaccggata cctgtccgcc tttctccctt    2640
cgggaagcgt ggcgctttct caatgctcac gctgtaggta tctcagttcg gtgtaggtcg    2700
ttcgctccaa gctgggctgt gtgcacgaac ccccctgttca gcccgaccgc tgcgccttat    2760
ccggtaacta tcgtcttgag tccaacccgg taagacacga cttatcgcca ctggcagcag    2820
ccactggtaa caggattagc agagcgaggt atgtaggcgg tgctacagag ttcttgaagt    2880
ggtggcctaa ctacggctac actagaagga cagtatttgg tatctgcgct ctgctgaagc    2940
cagttacctt cggaaaaaga gttggtagct cttgatccgg caaacaaacc accgctggta    3000
gcggtggttt ttttgtttgc aagcagcaga ttacgcgcag aaaaaaagga tctcaagaag    3060
atcctttgat cttttctacg gggtctgacg ctcagtggaa cgaaaactca cgttaaggga    3120
ttttggtcat gagattatca aaaaggatct tcacctagat ccttttaaat taaaaatgaa    3180
gttttaaatc aatctaaagt atatatgagt aaacttggtc tgacagttac caatgcttaa    3240
tcagtgaggc acctatctca gcgatctgtc tatttcgttc atccatagtt gcctgactcc    3300
ccgtcgtgta gataactacg atacgggagg gcttaccatc tggccccagt gctgcaatga    3360
taccgcgaga cccacgctca ccggctccag atttatcagc aataaaccag ccagccggaa    3420
gggccgagcg cagaagtggt cctgcaactt tatccgcctc catccagtct attaattgtt    3480
gccgggaagc tagagtaagt agttcgccag ttaatagttt gcgcaacgtt gttgccattg    3540
ctacaggcat cgtggtgtca cgctcgtcgt ttggtatggc ttcattcagc tccggttccc    3600
aacgatcaag gcgagttaca tgatcccca tgttgtgcaa aaaagcggtt agctccttcg    3660
gtcctccgat cgttgtcaga agtaagttgg ccgcagtgtt atcactcatg gttatggcag    3720
cactgcataa ttctcttact gtcatgccat ccgtaagatg cttttctgtg actggtgagt    3780
actcaaccaa gtcattctga gaatagtgta tgcggcgacc gagttgctct tgcccggcgt    3840
caatacggga taataccgcg ccacatagca gaactttaaa agtgctcatc attggaaaac    3900
gttcttcggg gcgaaaactc tcaaggatct taggcgtgtt gagatccagt tcgatgtaac    3960
ccactcgtgc acccaactga tcttcagcat cttttacttt caccagcgtt tctgggtgag    4020
caaaaacagg aaggcaaaat gccgcaaaaa agggaataag ggcgacacgg aaatgttgaa    4080
tactcatact cttccttttt caatattatt gaagcattta tcagggttat tgtctcatga    4140
gcggatacat atttgaatgt atttagaaaa ataaacaaat aggggttccg cgcacatttc    4200
cccgaaaagt gccacctgac gtctaagaaa ccattattat catgacatta acctataaaa    4260
ataggcgtat cacgaggccc tttcgtc                                      4287
```

<210> SEQ ID NO 13
<211> LENGTH: 190
<212> TYPE: PRT
<213> ORGANISM: Cowpea Chlorotic Mottle Virus

<400> SEQUENCE: 13

```
Met Ser Thr Val Gly Thr Gly Lys Leu Thr Arg Ala Gln Arg Ala
1               5                   10                  15

Ala Ala Arg Lys Asn Lys Arg Lys Thr Arg Val Val Gln Pro Val Ile
            20                  25                  30

Val Glu Pro Ile Ala Ser Gly Gln Gly Lys Ala Ile Lys Ala Trp Thr
            35                  40                  45

Gly Tyr Ser Val Ser Lys Trp Thr Ala Ser Cys Ala Ala Glu Ala
50                  55                      60

Lys Val Thr Ser Ala Ile Thr Ile Ser Leu Pro Asn Glu Leu Ser Ser
65                  70                  75                  80

Glu Arg Asn Lys Gln Leu Lys Val Gly Arg Val Leu Leu Trp Leu Gly
                85                  90                  95

Leu Leu Pro Ser Val Ser Gly Thr Val Lys Ser Cys Val Thr Glu Thr
            100                 105                 110

Gln Thr Thr Ala Ala Ala Ser Phe Gln Val Ala Leu Ala Val Ala Asp
            115                 120                 125

Asn Ser Lys Asp Val Val Ala Ala Met Tyr Pro Glu Ala Phe Lys Gly
130                 135                 140

Ile Thr Leu Glu Gln Leu Thr Ala Asp Leu Thr Ile Tyr Leu Tyr Ser
145                 150                 155                 160

Ser Ala Ala Leu Thr Glu Gly Asp Val Ile Val His Leu Glu Val Glu
                165                 170                 175

His Val Arg Pro Thr Phe Asp Asp Ser Phe Thr Pro Val Tyr
                180                 185                 190

<210> SEQ ID NO 14
<211> LENGTH: 573
<212> TYPE: DNA
<213> ORGANISM: Cowpea Chlorotic Mottle Virus

<400> SEQUENCE: 14
atgtctacag tcggaacagg gaagttaact cgtgcacaac gaagggctgc ggcccgtaag      60
aacaagcgga agactcgtgt ggtccaacct gttattgtag aacccatcgc ttcaggccaa     120
ggcaaggcta ttaaagcatg gaccggttac agcgtatcga agtggaccgc ctcttgtgcg     180
gctgccgaag ctaaagtaac ctcggctata actatctctc tccctaatga gctatcgtcc     240
gaaaggaaca agcagctcaa ggtaggtaga gttttattat ggcttgggtt gcttcccagt     300
gttagtggca cagtgaaatc ctgtgttaca gagacgcaga ctactgctgc tgcctccttt     360
caggtggcat tagctgtggc cgacaactcg aaagatgttg tcgctgctat gtaccccgag     420
gcgtttaagg gtataaccct tgaacaactc accgcggatt taacgatcta cttgtacagc     480
agtgcggctc tcactgaggg cgacgtcatc gtgcatttgg aggttgagca tgtcagacct     540
acgtttgacg actctttcac tccggtgtat tag                                  573

<210> SEQ ID NO 15
<211> LENGTH: 75
<212> TYPE: DNA
<213> ORGANISM: Bacillus anthracis

<400> SEQUENCE: 15
agtaattctc gtaagaaacg ttctacctct gctggcccta ccgtgcctga tcgtgataat      60
gatggcattc ctgat                                                       75

<210> SEQ ID NO 16
<211> LENGTH: 75
```

```
<212> TYPE: DNA
<213> ORGANISM: Bacillus anthracis

<400> SEQUENCE: 16
agtcctgaag ctcgtcatcc tctcgtggct gcgtatccta ttgtgcatgt tgatatggaa    60
aatattatcc tctct                                                    75

<210> SEQ ID NO 17
<211> LENGTH: 75
<212> TYPE: DNA
<213> ORGANISM: Bacillus anthracis

<400> SEQUENCE: 17
cgtattattt tcaatggcaa agatctcaat ctcgtggaac gtcgtattgc tgctgtgaat    60
ccttctgatc ctctc                                                    75

<210> SEQ ID NO 18
<211> LENGTH: 75
<212> TYPE: DNA
<213> ORGANISM: bacillus anthracis

<400> SEQUENCE: 18
cgtcaagatg gcaaaacctt cattgatttc aaaaagtata atgataaact ccctctctat    60
atttctaatc ctaat                                                    75

<210> SEQ ID NO 19
<211> LENGTH: 26
<212> TYPE: DNA
<213> ORGANISM: artificial
<220> FEATURE:
<223> OTHER INFORMATION: CCMVRNA4.primer

<400> SEQUENCE: 19
ctcgagctaa tacaccggag tgaaag                                        26

<210> SEQ ID NO 20
<211> LENGTH: 26
<212> TYPE: DNA
<213> ORGANISM: artificial
<220> FEATURE:
<223> OTHER INFORMATION: CCMVRNA4.F primer

<400> SEQUENCE: 20
ctgcagatgt ctacagtcgg aacagg                                        26

<210> SEQ ID NO 21
<211> LENGTH: 20
<212> TYPE: DNA
<213> ORGANISM: artificial
<220> FEATURE:
<223> OTHER INFORMATION: CCMV-CP-F1 primer

<400> SEQUENCE: 21
aacccatcgc ttcaggccaa                                               20

<210> SEQ ID NO 22
<211> LENGTH: 29
<212> TYPE: DNA
<213> ORGANISM: artificial
<220> FEATURE:
<223> OTHER INFORMATION: CCMV-CP-XbaI primer

<400> SEQUENCE: 22
gctctagaat gtctacagtc ggaacaggg                                     29
```

<210> SEQ ID NO 23
<211> LENGTH: 30
<212> TYPE: DNA
<213> ORGANISM: artificial
<220> FEATURE:
<223> OTHER INFORMATION: CCMV-CP-EcoRI primer

<400> SEQUENCE: 23
cggaattctt actaatacgg agtgaaagag                              30

<210> SEQ ID NO 24
<211> LENGTH: 28
<212> TYPE: DNA
<213> ORGANISM: artificial
<220> FEATURE:
<223> OTHER INFORMATION: CCMV-CP-EcoRI-3'UTR

<400> SEQUENCE: 24
cggaatcctg gtctccttag agatcacc                                28

<210> SEQ ID NO 25
<211> LENGTH: 26
<212> TYPE: DNA
<213> ORGANISM: artificial
<220> FEATURE:
<223> OTHER INFORMATION: CCMV.F primer

<400> SEQUENCE: 25
ccagaaggta attatccaag atgtag                                  26

<210> SEQ ID NO 26
<211> LENGTH: 25
<212> TYPE: DNA
<213> ORGANISM: artificial
<220> FEATURE:
<223> OTHER INFORMATION: NOS TERM R primer

<400> SEQUENCE: 26
cgatccccga tctagtaaca tagat                                   25

<210> SEQ ID NO 27
<211> LENGTH: 18
<212> TYPE: DNA
<213> ORGANISM: artificial
<220> FEATURE:
<223> OTHER INFORMATION: CCMV-RNA3 Insert

<400> SEQUENCE: 27
cgtatttctg atcctctc                                           18

<210> SEQ ID NO 28
<211> LENGTH: 6
<212> TYPE: PRT
<213> ORGANISM: artificial
<220> FEATURE:
<223> OTHER INFORMATION: CCMV-RNA3 Insert

<400> SEQUENCE: 28

Arg Ile Ser Asp Pro Leu
1               5